(12) United States Patent
Aronin et al.

(10) Patent No.: US 9,434,943 B2
(45) Date of Patent: Sep. 6, 2016

(54) RNA INTERFERENCE FOR THE TREATMENT OF GAIN-OF-FUNCTION DISORDERS

(71) Applicant: UNIVERSITY OF MASSACHUSETTS, Boston, MA (US)

(72) Inventors: Neil Aronin, Newtonville, MA (US); Phillip D. Zamore, Northboro, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/161,266

(22) Filed: Jan. 22, 2014

(65) Prior Publication Data

US 2014/0370597 A1    Dec. 18, 2014

Related U.S. Application Data

(63) Continuation of application No. 12/966,525, filed on Dec. 13, 2010, now Pat. No. 8,680,063, which is a continuation-in-part of application No. 12/348,794, filed on Jan. 5, 2009, now abandoned, and a continuation-in-part of application No. 10/571,705, filed as application No. PCT/US2004/029968 on Sep. 13, 2004, now Pat. No. 7,947,658, said application No. 12/348,794 is a continuation of application No. PCT/US2007/015638, filed on Jul. 9, 2007.

(60) Provisional application No. 60/819,704, filed on Jul. 7, 2006, provisional application No. 60/502,678, filed on Sep. 12, 2003.

(51) Int. Cl.
C12N 15/113    (2010.01)
C12N 15/11     (2006.01)

(52) U.S. Cl.
CPC .......... *C12N 15/113* (2013.01); *C12N 15/111* (2013.01); *C12N 2310/14* (2013.01); *C12N 2310/3515* (2013.01); *C12N 2310/531* (2013.01); *C12N 2320/30* (2013.01); *C12N 2320/34* (2013.01)

(58) Field of Classification Search
USPC ....... 435/6.1, 91.1, 9, 1.31, 455, 91.31, 325, 435/320.1, 458, 366; 514/44; 536/23.1, 536/24.5
See application file for complete search history.

(56) References Cited

U.S. PATENT DOCUMENTS

| | | |
|---|---|---|
| 4,842,996 A | 6/1989 | Huynh-Dinh et al. |
| 5,328,470 A | 7/1994 | Nabel et al. |
| 5,814,014 A | 9/1998 | Elsberry et al. |
| 5,872,242 A | 2/1999 | Monia et al. |
| 5,965,722 A | 10/1999 | Ecker et al. |
| 6,093,180 A | 7/2000 | Elsberry |
| 6,107,094 A | 8/2000 | Crooke |
| 6,245,427 B1 | 6/2001 | Duzgunes et al. |
| 6,358,932 B1 | 3/2002 | Monia |
| 6,361,940 B1 | 3/2002 | Van Ness et al. |
| 6,506,559 B1 | 1/2003 | Driver et al. |
| 7,241,618 B2 | 7/2007 | Agami et al. |
| 7,320,965 B2 | 1/2008 | Sah et al. |
| 7,459,547 B2 | 12/2008 | Zamore et al. |
| 2002/0012968 A1 | 1/2002 | Carroll et al. |
| 2002/0086356 A1 | 7/2002 | Tuschl et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0069195 A1 | 4/2003 | Farrar et al. |
| 2003/0108923 A1 | 6/2003 | Tuschl et al. |
| 2003/0144232 A1 | 7/2003 | Agami et al. |
| 2003/0144239 A1 | 7/2003 | Agami et al. |
| 2003/0162734 A1 | 8/2003 | Miller et al. |
| 2003/0180756 A1 | 9/2003 | Shi et al. |
| 2003/0190635 A1 | 10/2003 | McSwiggen |
| 2004/0023390 A1 | 2/2004 | Davidson et al. |
| 2004/0096843 A1 | 5/2004 | Rossi et al. |
| 2004/0162255 A1 | 8/2004 | Kaemmerer |
| 2004/0171030 A1 | 9/2004 | Baker et al. |
| 2004/0175703 A1 | 9/2004 | Kreutzer et al. |
| 2004/0180351 A1 | 9/2004 | Giese et al. |
| 2004/0192629 A1 | 9/2004 | Xu et al. |
| 2004/0203145 A1 | 10/2004 | Zamore et al. |
| 2004/0214198 A1 | 10/2004 | Rana |
| 2004/0219671 A1 | 11/2004 | McSwiggen et al. |
| 2004/0220132 A1 | 11/2004 | Kaemmerer |
| 2004/0229266 A1 | 11/2004 | Tuschl et al. |

(Continued)

FOREIGN PATENT DOCUMENTS

| | | |
|---|---|---|
| CA | 2432341 A1 | 7/2002 |
| CA | 2432350 A1 | 7/2002 |
| DE | 10160151 A1 | 6/2003 |
| DE | 10302421 A1 | 7/2004 |
| EP | 1389637 A1 | 2/2004 |

(Continued)

OTHER PUBLICATIONS

Holen et al, Nucleic Acids Res., vol. 30, No. 8, 1757-1766 (2002).*
Doench et al Genes & Development, vol. 18, No. 5, pp. 504-511 (2004).*
Abdelgany, Amr et al., "Allele-specific silencing of a pathogenic mutant acetylcholine receptor subunit by RNA interference," Human Molecular Genetics, vol. 12(20):2637-2644 (2003).

(Continued)

*Primary Examiner* — Jane Zara
(74) *Attorney, Agent, or Firm* — Lathrop & Gage, LLP.; James H. Velema, Esq.

(57) ABSTRACT

The present invention relates to the discovery of an effective treatment for a variety of gain-of-function diseases, in particular, Huntington's disease (HD). The present invention utilizes RNA Interference technology (RNAi) against polymorphic regions in the genes encoding various gain-of-function mutant proteins resulting in an effective treatment for the gain-of-function disease.

12 Claims, 26 Drawing Sheets

(56) References Cited

U.S. PATENT DOCUMENTS

| | | |
|---|---|---|
| 2004/0241854 A1 | 12/2004 | Davidson et al. |
| 2004/0248299 A1 | 12/2004 | Jayasena et al. |
| 2004/0259247 A1 | 12/2004 | Tuschl et al. |
| 2004/0259248 A1 | 12/2004 | Tuschl et al. |
| 2005/0020521 A1 | 1/2005 | Rana |
| 2005/0026278 A1 | 2/2005 | Tuschl et al. |
| 2005/0037988 A1 | 2/2005 | Zamore et al. |
| 2005/0042646 A1 | 2/2005 | Davidson et al. |
| 2005/0059005 A1 | 3/2005 | Tuschl et al. |
| 2005/0074757 A1 | 4/2005 | Kreutzer et al. |
| 2005/0096284 A1 | 5/2005 | McSwiggen |
| 2005/0106731 A1 | 5/2005 | Davidson et al. |
| 2005/0130184 A1 | 6/2005 | Xu et al. |
| 2005/0130919 A1 | 6/2005 | Xu et al. |
| 2005/0137155 A1 | 6/2005 | McSwiggen et al. |
| 2005/0176045 A1 | 8/2005 | Fedorov et al. |
| 2005/0181382 A1 | 8/2005 | Zamore et al. |
| 2005/0182005 A1 | 8/2005 | Tuschl et al. |
| 2005/0186586 A1 | 8/2005 | Zamore et al. |
| 2005/0186591 A1 | 8/2005 | Bumcrot et al. |
| 2005/0191638 A1 | 9/2005 | McSwiggen |
| 2005/0227256 A1 | 10/2005 | Hutvagner et al. |
| 2005/0227940 A1 | 10/2005 | Rossi et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0246794 A1 | 11/2005 | Khvorova et al. |
| 2005/0255086 A1 | 11/2005 | Davidson et al. |
| 2005/0256072 A1 | 11/2005 | Aronin et al. |
| 2005/0273868 A1 | 12/2005 | Rana |
| 2005/0277133 A1 | 12/2005 | McSwiggen |
| 2005/0277610 A1 | 12/2005 | Rossi et al. |
| 2006/0009402 A1 | 1/2006 | Zamore et al. |
| 2006/0009408 A1 | 1/2006 | Davidson et al. |
| 2006/0069050 A1 | 3/2006 | Rana |
| 2006/0128650 A1 | 6/2006 | Xu |
| 2006/0134787 A1 | 6/2006 | Zamore et al. |
| 2006/0166910 A1 | 7/2006 | Tuschl et al. |
| 2006/0178328 A1 | 8/2006 | Kaemmerer |
| 2006/0178334 A1 | 8/2006 | Rossi et al. |
| 2006/0212950 A1 | 9/2006 | Tuschl et al. |
| 2006/0257912 A1 | 11/2006 | Kaemmerer et al. |
| 2006/0270623 A1* | 11/2006 | McSwiggen .................. 514/44 |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0104688 A1 | 5/2007 | Rossi et al. |
| 2007/0105803 A1 | 5/2007 | Manoharan et al. |
| 2007/0111228 A1 | 5/2007 | Jayasena et al. |
| 2007/0161590 A1 | 7/2007 | Van Bilsen et al. |
| 2007/0161591 A1 | 7/2007 | Aronin et al. |
| 2007/0161595 A1 | 7/2007 | Bumcrot et al. |
| 2007/0207974 A1 | 9/2007 | Khvorova et al. |
| 2007/0259827 A1 | 11/2007 | Aronin et al. |
| 2007/0261126 A1 | 11/2007 | Kaemmerer et al. |
| 2007/0265220 A1 | 11/2007 | Rossi et al. |
| 2008/0020058 A1 | 1/2008 | Chen et al. |
| 2008/0039415 A1 | 2/2008 | Stewart et al. |
| 2009/0004668 A1* | 1/2009 | Chen et al. .................. 435/6 |
| 2011/0213010 A1* | 9/2011 | Hayden et al. ............. 514/44 A |

FOREIGN PATENT DOCUMENTS

| | | |
|---|---|---|
| EP | 1527176 B1 | 5/2005 |
| EP | 1857547 A2 | 11/2007 |
| WO | WO 94/19493 A1 | 9/1994 |
| WO | WO 98/48009 A2 | 10/1998 |
| WO | WO 01/75164 A2 | 10/2001 |
| WO | WO 02/44321 * | 6/2002 |
| WO | WO 02/055692 A2 | 7/2002 |
| WO | WO 02/055693 A2 | 7/2002 |
| WO | WO 03/006477 A1 | 1/2003 |
| WO | WO 03/013437 A2 | 2/2003 |
| WO | WO 03/020931 A2 | 3/2003 |
| WO | WO 03/035869 A1 | 5/2003 |
| WO | WO 03/050306 A1 | 6/2003 |
| WO | WO 03/056012 A1 | 7/2003 |
| WO | WO 03/068797 A1 | 8/2003 |
| WO | WO 03/070895 A2 | 8/2003 |
| WO | WO 03/080807 A2 | 10/2003 |
| WO | WO 03/001335 A2 | 12/2003 |
| WO | WO 2004/013280 A2 | 2/2004 |
| WO | WO 2004/013310 A2 | 2/2004 |
| WO | WO 2004/013355 A1 | 2/2004 |
| WO | WO 2004/014933 A1 | 2/2004 |
| WO | WO 2004/015107 A2 | 2/2004 |
| WO | WO 2004/029212 A2 | 4/2004 |
| WO | WO 2004/042027 A2 | 5/2004 |
| WO | WO 2004/045543 A2 | 6/2004 |
| WO | WO 2004/046324 A2 | 6/2004 |
| WO | WO 2004/047872 A2 | 6/2004 |
| WO | WO 2004/058940 A2 | 7/2004 |
| WO | WO 2004/065601 A2 | 8/2004 |
| WO | WO 2004/080406 A2 | 9/2004 |
| WO | WO 2004/111072 A2 | 12/2004 |
| WO | WO 2004/111191 A2 | 12/2004 |
| WO | WO 2005/001043 A2 | 1/2005 |
| WO | WO 2005/003350 A2 | 1/2005 |
| WO | WO 2005/007875 A2 | 1/2005 |
| WO | WO 2005/007877 A2 | 1/2005 |
| WO | WO 2005/019453 A2 | 3/2005 |
| WO | WO 2005/023991 A2 | 3/2005 |
| WO | WO 2005/027980 A1 | 3/2005 |
| WO | WO 2005/045034 A2 | 7/2005 |
| WO | WO 2005/062937 A2 | 7/2005 |
| WO | WO 2005/069987 A2 | 8/2005 |
| WO | WO 2005/078096 A2 | 8/2005 |
| WO | WO 2005/079532 A2 | 9/2005 |
| WO | WO 2005/079533 A2 | 9/2005 |
| WO | WO 2005/089287 A2 | 9/2005 |
| WO | WO 2005/105995 A2 | 11/2005 |
| WO | WO 2005/116212 A2 | 12/2005 |
| WO | WO 2006/015389 A2 | 2/2006 |
| WO | WO 2006/121960 A2 | 11/2006 |
| WO | WO 2007/002904 A2 | 1/2007 |
| WO | WO 2007/022470 A2 | 2/2007 |
| WO | WO 2007/022506 A2 | 2/2007 |
| WO | WO 2007/047692 A2 | 4/2007 |
| WO | WO 2007/087451 A2 | 8/2007 |
| WO | WO 2008/005562 A2 | 1/2008 |
| WO | WO 2008/021136 A2 | 2/2008 |
| WO | WO 2008/021157 A1 | 2/2008 |
| WO | WO 2008/143774 A2 | 11/2008 |
| WO | WO 2008/147887 A1 | 12/2008 |

OTHER PUBLICATIONS

Agrawal et al., Molecular Med. Today, vol. 6, pp. 72-81 (2000).

Akhtar, Saghir et al., "Nonviral delivery okf synthetic siRNAs in vivo," The Journal of Clinical Investigation, vol. 117 (12):3623-3632 (2007).

Amarguioui, Mohammed et al., "Rational design and in vitro and in vivo delivery of Dicer substrate si RNA," Nature Protocols, vol. 1(2):508-517 (2006).

Amarzguioui, Mohammed et al., "Tolerance for mutations and chemical modifications in a siRNA," Nucleic Acids Research, vol. 31(2):589-595 (2003).

Ambros, Victor et al., "MicroRNAs and Other Tiny Endogenous RNAs in C. elegans," Current Biology, vol. 13:807-818 (2003).

Aoki, Yuji et al., "Potential tumor-targeting peptide vector of histidylated oligolysine conjugated to a tumor-homing RGD motif," Cancer Gene Therapy, vol. 8:783-787 (2001).

Aravin, Alexei a. et al., "The Small RNA Profile during Drosophila melanogaster Development," Developmental Cell, vol. 5:337-350 (2003).

Aronin, Neil et al., "Are there multiple pathways in the pathogenesis of Huntington's disease?" Phil. Trans. R. Soc. Lond. B, vol. 354:995-1003 (1999).

(56) References Cited

OTHER PUBLICATIONS

Aronin, Neil et al., "CAG Expansion Affects the Expression of Mutant Huntingtin in the Huntington's Disease Brain," Neuron, vol. 15:1193-1201 (1995).
Bagella, Luigi et al., "Cloning of Murine CDK9/PITALRE and Its Tissue-Specific Expression in Development," Journal of Cellular Physiology, vol. 177:206-213 (1998).
Bailly, Christian et al., "The use of diaminopurine to investigate structural properties of nucleic acids and molecular recognition between ligands and DNA," Nucleic Acids Research, vol. 26(19):4309-4314 (1998).
Bartel, David P., "MicroRNAs: genomics, biogenesis, mechanism, and function," Cell, vol. 116(2):281-297 (2004).
Bass, Brenda L., "The short answer," Nature, vol. 411:428-429 (2001).
Behding, Anders et al., "In vitro photochemical cataract in mice lacking copper-zinc superoxide dismutase," Free Radical Biology & Medicine, vol. 31(6):738-744 (2001).
Bernstein, Emily et al., "Role for a bidentate ribonuclease in the initiation step of RNA interference," Nature, vol. 409:363-366 (2001).
Bijsterbosch, Martin K. et al., "Modulation of plasma protein binding and in vivo liver cell uptake of phosphorothioate oligodeoxynucleotides by cholesterol conjugation," Nucleic Acids Research, vol. 28(14):2717-2725 (2000).
Boden, Daniel et al., "Efficient Gene Transfer of HIV-1-Specific Short Hairpin RNA into Human Lymphocytic Cells Using Recombinant Adeno-associated Virus Vectos," Molecular Therapy, vol. 9(3):396-402 (2004).
Boden, Daniel et al., "Enhanced gene silencing of HIV-1 specific siRNA using microRNA designed hairpins," Nucleic Acids Research, vol. 32(3):1154-1158 (2004).
Bohnsack, Markus T. et al., "Exportin 5 is a RanGTP-dependent dsRNA-binding protein that mediates nuclear export of pre-miRNAs," RNA, vol. 10:185-191 (2004).
Bonnet, Eric et al., "Evidence that microRNA precursors, unlike other non-coding RNAs, have lower folding free energies than random sequences," Bioinformatics, vol. 20(17):2911-2917 (2004).
Boudreau, Ryan L. et al., "Nonallele-specific Silencing of Mutant and Wild-type Huntingtin Demonstrates Therapeutic Efficacy in Huntington's Disease Mice," Molecular Therapy, doi:10.1038/mt.2009.17 (2009).
Boutla, Alexandra et al, "Developmental defects by antisense-mediated inactivation of micro-RNAs 2 and 13 in Drosophila and the identification of putative target genes," Nucleic Acids Research, vol. 31(17):4973-4980 (2003).
Boutla, Alexandra et al, "Short 5'-phosphorylated double-stranded RNAs induce Rna interference in Drosophila," Current Biology, vol. 11:1776-1780 (2001).
Bracht, John et al., "Trans-splicing and polyadenylation of let-7 microRNA primary transcripts," RNA, vol. 10:1586-1594 (2004).
Brennecke, Julius et al., "Bantam Encodes a Developmentally Regulated microRNA that Controls Cell Proliferation and Regulates the Proapoptotic Gene hid in Drosophila," Cell, vol. 113:25-36 (2003).
Brennecke, Julius et al., "Principles of MicroRNA-Target Recognition," PLoS Biology, vol. 3(3):0404-0418 (2005).
Brennecke, Julius et al., "Towards a complete description of the microRNA complement of animal genomes," Genome Biology, vol. 4:228.1-228.3 (2003).
Brown, Kirk M. et al., "Target accessibility dictates the potency of human RISC," Nature Structural & Molecular Biology, vol. 12(5):469-470 (2005).
Brummelkamp, Thijn R. et al., "A System for Stable Expression of Short Interfering RNAs in Mammalian Cells," Science, vol. 296:550-553 (2002).
Brummelkamp, Thijn R. et al., "Stable suppression of tumorigenicity by virus-mediated RNA interference," Cancer Cell, vol. 2:243-247 (2002).

Bumcrot, David et al., "RNAi therapeutics: a potential new class of pharmaceutical drugs," Nature Chemical Biology, vol. 2(12):711-719 (2006).
Burgess, Kevin et al., "Photolytic Mass Laddering for Fast Characterization of Oligomers on Single Resin Beads," J. Org. Chem., vol. 62:5662-5663 (1997).
Caccone, Adalgisa et al., "Calibration of the Change in Thermal Stability of DNA Duplexes and Degree of Base Pair Mismatch," J. Mol. Evol., vol. 27:212-216 (1988).
Cai, Xuezhong et al., "Human microRNA are processed from capped, polyadenylated transcripts that can also function as mRNAs," RNA, vol. 10:1957-1966 (2004).
Calegari, Federico et al., "Tissue-specific RNA interference in postimplantation mouse embryos with endoribonuclease-prepared short interfering RNA," PNAS, vol. 99(22):14236-14240 (2002).
Caplen, Natasha J. et al., "dsRNA-mediated gene silencing in cultured Drosophila cells: a tissue culture model for the analysis of RNA interference," Gene, vol. 252:95-105 (2000).
Caplen, Natasha J. et al., "Rescue of polyglutamine-mediated cytotoxicity by double-stranded RNA-mediated RNA interference," Human Molecular Genetics, vol. 11(2):175-184 (2002).
Caplen, Natasha J. et al., "Specific inhibition of gene expression by small double-stranded RNAs in invertebrate and vertebrate systems," PNAS, vol. 98(17):9742-9747 (2001).
Caplen, Natasha J., "RNAi as a gene therapy approach," Expert Opin. Biol. Ther., vol. 3(4):575-586 (2003).
Carthew, Richard W., "Gene silencing by double-stranded RNA," Current Opinion in Cell Biology, vol. 13:244248 (2001).
Catalanotto, Caterina et al., "Gene silencing in worms and fungi," Nature, vol. 404:245 (2000).
Catalanotto, Caterina et al., "Involvement of small RNAs and role of the qde genes in the gene silencing pathway in Neurospora," Genes & Development, vol. 16:790-795 (2002).
Caudy, Amy A. et al., "Fragile X-related protein and VIG associate with the RNA interference machinery," Genes & Development, vol. 16:2491-2496 (2002).
Chalk, A.M. et al., "siRNAdb: a database of siRNA sequences," Nucleic Acids Research, vol. 33:D131-D134 (2005).
Chaloin, L. et al., "Design of Carrier Peptide-Oligonucleotide Conjugates with Rapid Membrane Translocation and Nuclear Localization Properties," Biochemical and Biophysical Research Communications, vol. 243:601-608 (1998).
Charles River Laboratories, Inc., "R6/2 Mouse," retrieved online at: http://www.criver.com/en-US/ProdServ/ByType/Discovery/CNS/Huntingtons/Pag- es/R62.sub.--Mouse.sub.--aspx, 1 page (2013).
Check, Erika, "RNA to the rescue?" Nature, vol. 425:10-12 (2003).
Chen, Shu-Hsia et al., "Gene therapy for brain tumors: Regression of experimental gliomas by adenovirus-mediated gene transfer in vivo," Proc. Natl. Acad. Sci. USA, vol. 91:3054-3057 (1994).
Chen, Zongyu J. et al., "Sleeping Beauty-mediated down-regulation of huntingtin expression by RNA interference," Biochemical and Biophysical Research Communication, vol. 329:646-652 (2005).
Chi, Jen-Tsan et al., "Genomewide view of gene silencing by small interfering RNAs," PNAS, vol. 100(11):63436346 (2003).
Chirila et al., Biomaterials, vol. 23, pp. 321-342 (2002).
Chiu, Ya-Lin et al, "RNAi in Human Cells: Basic Structural and Functional Features of Small Interfering RNA," Molecular Cell, vol. 10:549-561 (2002).
Cleveland, Don W. et al., "From Charcot to Lou Gehrig: Deciphering Selective Motor Neuron Death in ALS," Nature, vol. 2:806-819 (2001).
Chiu, Ya-lin et al, "siRNA function in RNAi: A chemical modification analysis," RNA, vol. 9:1034-1048 (2003).
Cogoni, Carlo et al., "Gene silencing in Neurospora crassa requires a protein homologous to RNA-dependent RNA polymerase," Nature, vol. 399:166-168 (1999).
Cogoni, Carlo et al., "Isolation of quelling-defective (qde) mutants impaired in posttranscriptional transgene-induced gene silencing in Neurospora crassa," Proc. Natl. Acad. Sci. USA, vol. 94:10233-10238 (1997).
Cogoni, Carlo et al., "Posttranscriptional Gene Silencing in Neurospora by a RecQ DNA Helicase," Science, vol. 286:2342-2344 (1999).

(56) References Cited

OTHER PUBLICATIONS

Conte, Darryl Jr. et al., "RNA Interference in Caenorhabditis elegans," Current Protocols in Molecular Biology, F.M. Asubel et al., eds., John Wiley & Sons, pp. 26.3.1-26.3.20 (2003).

Corey, David R., "Chemical modification: the key to clinical application of RNA interference?" The Journal of Clinical Investigation, vol. 117(12):3615-3622 (2007).

Crooke, S., Ann. Rev. Medicine, vol. 55, pp. 61-95 (2004).

Cullen, Bryan R., "Enhancing and confirming the specificity of RNAi experiments," Nature Methods, vol. 3 (9):677-681 (2006).

Czauderna, Frank et al., "Structural variations and stabilising modifications of synthetic siRNAs in mammalian cells," Nucleic Acids Research, vol. 31(11):2705-2716 (2003).

Dalmay, Tamas et al., "An Rna-Dependent RNA Polymerase Gene in Arabidopsis Is Required for Posttranscriptional Gene Silencing Mediated by a Transgene but Not by a Virus," Cell, vol. 101:543-553 (2000).

Dalmay, Tamas et al., "SDE3 encodes an RNA helicase required for posttranscriptional gene silencing in Arabidopsis," The EMBO Journal, vol. 20(8):2069-2077 (2001).

Davidson, Beverly L. et al., "Molecular medicine for the brain: silencing of disease genes with RNA interference," The Lancet, vol. 3:145-149 (2004).

Denli, Ahmet M. et al., "Processing of primary microRNAs by the Microprocessor complex," Nature, vol. 432:231-235 (2004).

Derossi, Daniele et al., "The Third Helix of the Antennapedia Homeodomain Translocates through Biological Membranes," The Journal of Biological Chemistry, vol. 269(14):10444-10450 (1994).

Devroe, Eric et al., "Retrovirus-delivered siRNA," BMC Biotechnology, vol. 2:15-19 (2002).

Dharmacon RNA Technologies. On-Target siRNA. Company Brochure (2003).

Dharmacon RNA Technologies. Products for RNA Interference. Company brochure (2003).

Difiglia, M. et al., "Therapeutic silencing of mutant huntingtin with siRNA attenuates striatal and cortical neuropathology and behavioral deficits," PNAS, vol. 104(43):17204-17209 (2007).

Difiglia, Marian et al., "Aggregation of Huntingtin Neuronal Intranuclear Inclusions and Dystrophic Neurites in Brain," Science, vol. 277:1990-1993 (1997).

Difiglia, Marian et al., "Huntingtin Is a Cytoplasmic Protein Associated with Vesicles in Human and Rat Brain Neurons," Neuron, vol. 14:1075-1081 (1995).

Ding, Hongliu et al., "Selective silencing by RNAi of a dominant allele that causes amyotrophic lateral sclerosis," Aging Cell, vol. 2:209-217 (2003).

Doench, John G. et al., "siRNAs can function as miRNAs," Genes & Development, vol. 17:438-442 (2003).

Doench, John G. et al., "Specificity of microRNA target selection in translational repression," Genes & Development, 2004:504-511(2004).

Dostie, Josee et al, "Numerous microRNPs in neuronal cells containing novel microRNAs," RNA, vol. 9:180-186 (2003).

Du, Quan et al., "A systematic analysis of the silencing effects of an active siRNA at all single-nucleotide mismatched target sites," Nucleic Acids Research, vol. 33(5):1671-1677 (2005).

Duprez, Laurence, et al., "Pathology of the TSH Receptor," Journal of Pediatric Endocrinology & Metabolism, vol. 12:295-302 (1999).

Dykxhoorn, Derek M. et al., "Determinants of specific RNA interference-mediated silencing of human b-globin alleles differing by a single nucleotide polymorphism," PNAS, vol. 103(15):5953-5958 (2006).

Elbashir, S.M., et al., "Duplexes of 21-nucleotide RNAs mediate RNA interferences in cultured mammalian cells," Nature, vol. 411:494-498 (2001).

Elbashir, S.M., et al., "Functional anatomy of siRNAs for mediateing efficient RNAi in Drosophila melanogaster embryo lysate," Embo. J., vol. 20:6877-6888 (2001).

Elbashir, Sayda M. et al., "RNA interference is mediated by 21- and 22-nucleotide RNAs," Genes & Development, vol. 15:188-200 (2001).

Elmquist, Anna et al., "VE-Cadherin-Derived Cell-Penetrating Peptide, pVEC, with Carrier Functions," Experimental Cell Research, vol. 269:237-244 (2001).

Enright, Anton J. et al., "MicroRNA targets in *Drosophila*," Genome Biology, vol. 5:R1.1-R1.14 (2003).

Epa, W. Ruwan et al., "Enhanced Downregulation of the p75 Nerve Growth Factor Receptor by Cholesteryl and Bis-Cholesteryl Antisense Oligonucleotides," Antisenxe & Nucleic Acid Drug Development, vol. 8:489-498 (1998).

European Office Action for Application No. 047783980, 4 pages, dated Sep. 29, 2009.

Fagard, Mathilde et al., "AGO1, QDE-2, and RDE-1 are related proteins required for post-transcriptional gene silencing in plants, quelling in fungi, and RNA interference in animals," PNAS, vol. 97(21):11650-11654 (2000).

Fire, Andrew et al., "Potent and specific genetic interference by double-stranded RNA in Caenorhabditis elegans," Nature, vol. 391:806-811 (1998).

Flood, Dorothy G. et al., "Hindlimb Motor Neurons Require Cu/Zn Superoxide Dismutase for Maintenance of Neuromuscular Junctions," American Journal of Pathology, vol. 155(2):663-672 (1999).

Fluiter, K. et al., "Killing cancer by targeting genes that cancer cells have lost: Allele-specific inhibition, a novel approach to the treatment of genetic disorders," CMLS, Cell. Mol. Life Sci., vol. 60:834-843 (2003).

Fluiter, Kees et al., "Tumor Genotype-specific Growth Inhibition in Vivo by Antisense Oligonucleotides against a Polymorphic Site of the Large Subunit of Human RNA Polymerase II," Cancer Research, vol. 62:2024-2028 (2002).

Forstemann, K. et al., "Normal microRNA maturation and germline stem cell maintenance requires loquacious, a double-stranded RNA-binding domain protein," PLOS Biology, vol. 3(7):1-15 (2005).

Francis, Ross et al., "aph-1 and pen-2 Are Required for Notch Pathway Signaling, g-Secretase Cleavage of bAPP, and Presenilin Protein Accumulation," Development Cell, vol. 3:85-97 (2002).

Fressinaud, Edith et al., "Molecular Genetics of Type 2 von Willebrand Disease," International Journal of Hematology, vol. 75:9-18 (2002).

Gante, Joachim, "Azapeptides," Synthesis, vol. 6:405-406 (1989).

Gaudette, Mara et al., "Current status of SOD1 mutations in familial amyotrophic lateral sclerosis," Amyotrophic Lateral Sclerosis, vol. 1(2):83-89 (2000).

GenBank Accession No. NM.sub.--002111, Rangone, H. et al., "PHosphorylation of arfaptin 2 at Ser260 by Akt Inhibits PolyQ-huntingtin-induced toxicity by rescuing proteasome impairment," J. Biol. Chem., vol. 280(23):22021-22028 (2005) Aug. 8, 2005.

German Application, File No. 101 55 280.7, dated Oct. 26, 2001.
German Application, File No. 101 58 411.3, dated Nov. 29, 2001.
German Application, File No. 101 60 151.4, dated Dec. 7, 2001.
German Application, File No. 102 35 620.3, dated Aug. 2, 2002.

Gewirtz, Alan M. et al., "On future's doorstep: RNA interference and the pharmacopeia of tomorrow," The Journal of Clinical Investigation, vol. 117(12):3612-3614 (2007).

Ghildiyal, Megha et al., "Small silencing RNAs: an expanding universe," Nature Review Genetics, vol. 10:94-108 (2009).

Goto, J. et al., "Suppression of Huntingtin Gene Expression by siRNA: A Possible Therapeutic Tool for Huntington's Disease," Neurology, vol. 60(5 Suppl. 1):A286 (2003).

Griffiths-Jones, Sam, "The microRNA Registry," Nucleic Acids Research, vol. 32:D109-D111 (2004).

Grimm, Dirk et al., "Therapeutic application of RNAi: is mRNA tergeting finally ready for prime time?" the Journal of Clinical Investigation, vol. 117(12):3633-3641 (2007).

Grishok, a. et al., "Genes and Mechanisms related to RNA interference regulate expression of the small temporal RNAs that control C. elegans development timing," Cell, vol. 106:23-34 (2001).

Grishok, Alla et al., "Genetic Requirements for Inheritance of RNAi in C. elegans," Science, vol. 287:2494-2497 (2000).

(56) References Cited

OTHER PUBLICATIONS

Grishok, Alla et al., "RNAi (Nematodes Caenorhabditis elegans)," Advances in Genetics, vol. 46:339-360 (2002).

Grzelinski, Marius et al, "RNA Interference-Mediated Gene Silencing of Pleiotrophin Through Polyethylenimine-Complexed Small Interfering RNAs in Vivo Exerts Antitumoral Effects in Glioblastoma Xenografts," Human Gene Therapy, 17:751-766 (2006).

Gualberto, Antonio, et al., "An oncogenic form of p53 confers a dominant, gain-of-function phenotype that disrupts spindle checkpoint control," Proc. Natl. Acad. Sci. USA, vol. 95:5166-5171 (1998).

Ha, Ilho et al., "A bulged lin-4/lin-14 RNA duplex is sufficient for Caenorhabditis elegans lin-14 temporal gradient formation," Genes & Development, vol. 10:3041-3050 (1996).

Haley, B. et al., "Kinetic analysis of the RNAi enzyme complex," Nature Structural & Molecular Biology, vol. 11 (7):599-606 (2004).

Haley, Benjamin et al., "In vitro analysis of Rna interference in Drosophila melanogaster," Methods, vol. 30:330-336 (2003).

Halldorsson, Bjarni V. et al., "Optimal Selection of SNP Markers for Disease Association Studies," Hum. Hered., vol. 58:190-202 (2004).

Hamilton, Andrew J. et al., "A Species of Small Antisense RNA in Posttranscriptional Gene Silencing in Plants," Science, vol. 286:950-952 (1999).

Hammond, Scott M. et al., "An RNA-directed nuclease mediates post-transcriptional gene silencing in *Drosophila* cells," Nature, vol. 404:293-296 (2000).

Hammond, Scott M. et al., "Argonaute2, a Link Between Genetic and Biochemical Analyses of RNAi," Science, vol. 293:1146-1150 (2001).

Hammond, Scott M. et al., "Post-Transcriptional Gene Silencing by Double-Stranded RNA," Nature, vol. 2:110119 (2001).

Hannon, Gregory J. et al., "Unlocking the potential of the human genome with RNA interference," Nature, vol. 431:371-378 (2004).

Hannon, Gregory J., "RNA interference," Nature, vol. 418:244-251 (2002).

Harborth, Jens et al., "Identification of essential genes in cultured mammlian cells using small interfering RNAs," Journal of Cell Science, vol. 114:4557-4565 (2001).

Harper, Scott Q. et al., "RNA interference improves motor and neuropathological abnormalities in a Huntington's disease mouse model," PNAS, vol. 102(16):5820-5825 (2005).

Haubner, Roland et al., "Glycosylated RGD-Containing Peptides: Tracer for Tumor Targeting and Angiogenesis Imaging with Improved Biokinetics," The Journal of Nuclear Medicine, vol. 42(2):326-336 (2001).

Neale, Bret S.E. et al., "siRNA target site secondary structure predictions using local stable substructures," Nucleic Acids Research, vol. 33(3):1-10 (2005).

Hirota, Seiichi et al., "Gain-of-function mutation at the extracellular domain of KIT in gastrointestinal stromal tumours," Journal of Pathology, vol. 193:505-510 (2001).

Hirota, Seiichi, et al., "Gain-of-Function Mutations of c-kit in Human Gastrointestinal Stromal Tumors," Science, vol. 279:577-580 (1998).

Nixon, M.L., et al., "Gain of function properties of mutant p53 proteins at the mitotic spindle cell cycle checkpoint," Histology and Histopathology, vol. 15:551-556 (2000).

Ho, L.W., et al., "The molecular biology of Huntington's disease," Psychological Medicine, vol. 31:3-14 (2001).

Hoehn, Margaret M. et al., "Parkinsonism: onset, progression, and mortality," Neurology, vol. 17(5):427-442 (1967).

Hohjoh, Hirohiko, "Enhancement of RNAi activity by improved siRNA duplexes," FEBS Letters, vol. 557:193-198 (2004).

Hojo, S. et al., "Heterogeneous point mutations of the p53 gene in pulmonary fibrosis," Eur. Respir. J., vol. 12:1404-1408 (1998).

Holen et al., Nucleic Acids Res., vol. 30, No. 8, pp. 1757-1766 (2002).

Holen, Torgeir et al., "Positional effects of short interfering RNAs targeting the human coagulation trigger Tissue Factor," Nucleic Acids Research, vol. 30(8):1757-1766 (2002).

Holen, Torgeir et al., "Similar behaviour of single-strand and double-strand siRNAs suggests they act through a common RNAi pathway," Nucleic Acids Research, vol. 31(9):2401-2407 (2003).

Holmes, Christopher P., et al., "Strategies for Combinatorial Organic Synthesis: Solution and Polymer-Supported Synthesis of 4-Thiazolidinones and 4-Metathiazanones Derived from Amino Acids," J. Org. Chem., vol. 60:7328-7333.

Hsieh, Andrew C. et al., "A library of siRNA duplexes targeting the phosphoinositide 3-kinase pathway: determinants of gene silencing for use in cell-based screens," Nucleic Acids Research, vol. 32(3):893-901 (2004).

Hu-Lieskovan, Siwen et al., "Sequence-Specific Knockdown of EWS-FLI1 by Targeted, Nonviral Delivery of Small Interfering RNA Inhibits Tumor Growth in a Murine Model of Metastatic Ewing's Sarcoma," Cancer Res., vol. 65 (19):8984-8992 (2005).

Hutvagner, G. et al., "A cellular function for the RNA-interference enzyme dicer in the maturation of the let-7 small temporal RNA," Science, vol. 293:834-838 (2001).

Hutvagner, Gyorgy et al., "A microRNA in a Multiple-Turnover RNAi Enzyme Complex," Science, vol. 297:20562060 (2002).

Hutvagner, Gyorgy et al., "RNAi: nature abhors a double-strand," Curr. Opin. Genet. Dev., vol. 12:225-232 (2002).

International Preliminary Report on Patentability and Written Opinion for Application No. PCT/US2006/038704, 8 pages, dated Apr. 2, 2008.

International Preliminary Report on Patentability and Written Opinion for Application No. PCT/US2007/015638, 5 pages, dated Jan. 13, 2009.

International Search Report for Application No. PCT/US07/02324, 3 pages, dated Nov. 20, 2008.

International Search Report for Application No. PCT/US07/15638, 1 page, dated Sep. 8, 2008.

International Search Report for Application No. PCT/US2005/029011, 4 pages, dated Apr. 13, 2006.

Invitation to Pay Additional Fees for Application No. PCT/US2005/029011, 5 pages, dated Feb. 20, 2006.

Jackson, Aimee L. et al., "Expression profiling reveals off-target gene regulation by RNAi," Nature Biotechnology, vol. 21(6):635-637 (2003).

Jackson, Aimee L. et al., "Position-specific chemical modification of siRNAs reduces 'off-target' transcript silencing," RNA, vol. 12:1197-1205 (2006).

Jackson, Aimee L. et al., "Widespread siRNA 'off-target' transcript silencing mediated by seed region sequence complementarity," RNA, vol. 12:1179-1187 (2006).

Jacque, Jean-Marc et al., "Modulation of HIV-1 replication by RNA interference," Nature, vol. 418:435-438 (2002).

Kato, Shinsuke et al., "New consensus research on neuropathological aspects of familial amyotrophic lateral sclerosis with superoxide dismutase 1 (SOD1) gene mutations: Inclusions containing SOD1 in neurons and astrocytes," ALS, vol. 1:163-184 (2000).

Kawase, Makoto et al., "Exacerbation of Delayed Cell Injury After Transient Global Ischemia in Mutant Mice With CuZn Superoxide Dismutase Deficiency," Stroke, vol. 30:1962-1968 (1999).

Ketting, Rene F. et a., "mut-7 of C. elegans, Required for Transposon Silencing and RNA Interference, Is a Homolog of Werner Syndrome Helicase and RNaseD," Cell, vol. 99:133-141 (1999).

Ketting, Rene F. et al., "A genetic link between co-suppression and RNA interference in C. elegans," Nature, vol. 404:296-298 (2000).

Ketting, Rene F. et al., "Dicer functions in RNA interference and in synthesis of small RNA involved in developmental timing in C. elegans," Genes & Development, vol. 15:2654-2659 (2001).

Khan, Alim et al., "Sustained Polymeric Delivery of Gene Silencing Antisense ODNs, siRNA, DNAzymes and Ribozymes: In Vitro and in Vivo Studies," Journal of Drug Targeting, vol. 12(6):393-404 (2004).

Khvorova, A. et al., "Functional siRNAs and miRNAs exhibit strand bias," Cell, vol. 115:209-216 (2003).

(56) References Cited

OTHER PUBLICATIONS

Kierzek, Ryszard et al., "Thermodynamics of Single Mismatches in RNA Duplexes," Biochemistry, vol. 38:14214-14223 (1999).
Kim, David H. et al., "Strategies for silencing human disease using RNA interference," Nature Reviews Genetics, vol. 8:173-184 (2007).
Kim, Dong-Ho et al., "Synthetic dsRNA Dicer substrates enhances RNAi potency and efficacy," Nature Biotechnology, vol. 23(2):222-226 (2005).
Kim, V.N. et al., "MicroRNA Biogenesis: Coordinated cropping and dicing," Nature Reviews, vol. 6:376-385 (2005).
Kiriakidou, Marianthi et al., "A combined computational-experimental approach predicts human microRNA targets," Genes & Development, vol. 18:1165-1178 (2004).
Klug, N. et al., "A selective antisense oligonucleotide against the G93A mutant of the Cu/Zn-SOD1 mRNA, applied to the mouse brain," European Journal of Physiology, vol. 441(Suppl. 6):R205, No. P20-7, 1 page, (2001).
Knight, Scott W. et al., "A Role for the RNase III Enzyme DCR-1 in RNA Interference and Germ Line Development in Caenorhabditis elegans," Science, vol. 293:2269-2271 (2001).
Kondo, Takeo et al., "Reduction of CuZn-Superoxide Dismutase Activity Exacerbates Neuronal Cell Injury and Edema Formation after Transient focal Cerebral Ischemia," The Journal of Neuroscience, vol. 17(11):4180-4189 (1997).
Kopp, P., "Human Genome and Diseases: Review, The TSH receptor and its role in thyroid disease," CMLS, Cell. Mol. Life Sci., vol. 58:1301-1322 (2001).
Kosaki, Kenjiro et al., "PTPN11 (Protein-Tyrosine Phosphatase, Nonreceptor-Type II) Mutations in Seven Japanese Patients with Noonan Syndrome," The Journal of Clinical Endocrinology & Metabolism, vol. 87(8):3529-3533 (2002).
Kremer, Berry et al., "A Worldwide Study of the Huntington's Disease Mutation: The Sensitivity and Specificity of Measuring Cag Repeats," The New England Journal of Medicine, vol. 330(20):1401-1406 (1994).
Krol, Jacek et al., "Structural Features of MicroRNA (miRNA) Precursors and Their Relevance to miRNA Biogenesis and Small Interfering RNA/Short Hairpin RNA Design," The Journal of Biological Chemistry, vol. 279(40):42230-42239 (2004).
Kunst, Catherine B. et al., "Mutations in SOD1 associated with amyotrophic lateral sclerosis cause novel protein interactions," Nature Genetics, vol. 15:91-94 (1997).
Kwong, J.Q. et al., "RNAi-mediated inhibition of mutated htt in Huntington's disease models," Society for Neuroscience, Abstract, Presentation No. 208.18, 1 page, (2003).
Laforet, Genevieve A. et al., "Changes in Cortical and Striatal Neurons Predict Behavioral and Electrophysiological Abnormalities in a Transgenic Murine Model of Huntington's Disease," The Journal of Neuroscience, vol. 21 (23):9112-9123 (2001).
Lagos-Quintana, Mariana et al., "Identification of Novel Genes Coding for Small Expressed RNAs," Science, vol. 294:853-858 (2001).
Lagos-Quintana, Mariana et al., "Identification of Tissue-Specific MicroRNAs from Mouse," Current Biology, vol. 12:735-739 (2002).
Lagos-Quintana, Mariana et al., "New MicroRNAs from mouse and human," RNA, vol. 9:175-179 (2003).
Lai, Eric C., "Micro RNAs are complementary to 3' UTR sequence motifs that mediate negative post-transcriptional regulation," Nature Genetics, vol. 30:363-364 (2002).
Lam, Kit S. et al., "A new type of synthetic peptide library for identifying ligand-binding activity," Nature, vol. 354:82-84 (1991).
Lania, Andrea, et al., "G protein mutations in endocrine diseases," European Journal of Endocrinology, vol. 145:543-559 (2001).
Lau, Nelson C. et al., "An Abundant Class of Tiny RNAs with Probable Regulatory Roles in Caenorhabditis elegans," Science, vol. 294:858-862 (2001).

Lee, Nan Sook et al., "Expression of small interfering RNAs targeted against HIV-1 rev transcripts in human cells," Nature Biotechnology, vol. 19:500-505 (2002).
Lee, Rosalind C. et al., "An Extensive Class of Small RNAs in Caenorhabditis elegans," Science, vol. 294:862-864 (2001).
Lee, Rosalind C. et al., "The C. elegans Heterochronic Gene lin-4 Encodes Small RNAs with Antisense Complementarity to lin-14," Cell, vol. 75:843-854 (1993).
Lee, Sang-Kyung et al., "Lentiviral delivery of short hairpin RNAs protects CD4 T cells from multiple clades and primary isolates of HIV," Blood, vol. 106(3):818-826 (2005).
Lee, Yoontae et al., "MicroRNA genes are transcribed by RNA polymerase II," The EMBO Journal, vol. 23:40514060 (2004).
Lee, Yoontae et al., "MicroRNA maturation: stepwise processing and subcellular localization," The EMBO Journal, vol. 21(17):4663-4670 (2002).
Lee, Yoontae et al., "The nuclear RNase III Drosha initiates microRNA processing," Nature, vol. 425:415-419 (2003).
Lewis, Benjamin P. et al., "Conserved Seed Pairings, Often Flanked by Adenosines, Indicates that Thousands of Human Genes are MicroRNA Targets," Cell, vol. 120:15-20 (2005).
Lewis, Benjamin P. et al., "Prediction of Mammalian MicroRNA Targets," Cell, vol. 115:787-798 (2003).
Lewis, David L. et al., "Efficient delivery of siRNA for inhibition of gene expression in postnatal mice," Nature Genetics, vol. 32:107-108 (2002).
Li, Bao-jian et al., "Using siRNA in prophylactic and therapeutic regimens against SARS coronavirus in Rhesus macaque," Nature Medicine, vol. 11(9):944-951 (2005).
Li, Zhaoyang et al., "Specific inhibition of Hiv-1 replication by short hairpin RNAs targeting human cyclin T1 without inducing apoptosis," FEBS Letters, vol. 579:3100-3106 (2005).
Liang, Xue-hai et al., "Small nucleolar RNA interference induced by antisense or double-Stranded Rna in trypanosomatids," PNAS, vol. 100(13):7521-7526 (2003).
Lieberman, Judy et al., "Interfering with disease: opportunities and roadblocks to harnessing RNA interference," Trends in Molecular Medicine, vol. 9(9):397-403 (2003).
Lim, Lee P. et al., "Microarray analysis shows that some microRNAs downregulate large Nos. Of target mRNAs," Nature, vol. 433:769-773 (2005).
Lim, Lee P. et al., "The microRNAs of Caenorhabditis elegans," Genes & Development, vol. 17:991-1008 (2003).
Lim, Lee P. et al., "Vertebrate MicroRNA Genes," Science, vol. 299:1540 (2003).
Limbach, Patrick A. et al., "Summary; the modified nucleosides of RNA," Nucleic Acids Research, vol. 22 (12):2183-2196 (1994).
Lipardi, Concetta et al., "RNAi as Random Degradative PCR: siRNA Primers Convert mRNA into dsRNAs that Are Degraded to Generate New siRNAs," Cell, vol. 107:297-307 (2001).
Liu, Qinghua et al., "R2D2, a Bridge Between the Initiation and Effector Steps of the Drosophila RNAi Pathway," Science, vol. 301:1921-1925 (2003).
Liu, Wanzhao et al., "Linking SNPs to CAG repeat length in Huntington's disease patients," Nature Methods, vol. 5 (11):951-953 (2008).
Liu, Wanzhao et al., "Specific inhibition of Huntington's disease gene expression by siRNAs in cultured cells," Proc. Japan Acad., vol. 79(B):293-298 (2003).
Lorenz, Christina et al., "Steroid and lipid conjugates of siRNAs to enhance cellular uptake and gene silencing in liver cells," Bioorganic & Medicinal Chemistry Letters, vol. 14:4975-4977 (2004).
Lund, Elsebet et al., "Nuclear Export of MicroRNA Precursors," Science, vol. 303:95-98 (2004).
Luyten, Ingrid et al., "Hybridization properties of base-modified oligonucleotides within the double and triple helix motif," Eur. J. Med. Chem., vol. 33:515-576 (1998).
MacDonald, Marcy E. et al., "A Novel Gene Containing a Trinucleotide Repeat That Is Expanded and Unstable on Huntington's Disease Chromosomes," Cell, vol. 72:971-983 (1993).

(56) References Cited

OTHER PUBLICATIONS

Mahato, Ram I. et al., "Modulation of gene expression by antisense and antigene okligodeoxynucleotides and small interfering RNA," Expert Opin. Drug Delivery, vol. 2(1):3-28 (2005).
Mallory, A.C., "MicroRNA control of PHABULOSA in leaf development: importance of pairing to the microRNA 5' region," EMBO J., vol. 23(16)3356-3364 (2004).
Manoharan, Muthiah et al., "Oligonucleotide Conjugates: Alteration of the Pharmacokinetic Properties of Antisense Agents," Nucleoside & Nucleotides, vol. 14(3-5):969-973 (1995).
Martinez, Javier et al., "Single-Stranded Antisense siRNAs Guide Target RNA Cleavage in RNAi," Cell, vol. 110:563-574 (2002).
Martinez, Luis Alfonso et al., "Synthetic small inhibiting RNAs: Efficient tools to inactivate oncogenic mutations and restore p53 pathways," PNAS, vol. 99(23):14849-14854 (2002).
Mas-Monteys, Alex et al., "Allele-Specific Silencing of Mutant Huntingtin for Huntington's Disease Therapy," Molecular Therapy, vol. 13(Suppl. 1):S274-S275, Abstract 733, (2006).
Matz, Paul G. et al., "Cell Death After Exposure to Subarachnoid Hemolysate Correlates Inversely With Expression of CuZn-Superoxide Dismutase," Stroke, vol. 31:2450-2458 (2000).
Matzuk, Martin M. et al., "Ovarian Function in Superoxide Dismutase 1 and 2 Knockout Mice," Endocrinology, vol. 139(9):4008-4011 (1998).
Maxwell, Michele M. et al., "RNA interference-mediated silencing of mutant superoxide dismutase rescues cyclosporin A-induced death in cultured neuroblastoma cells," PNAS, vol. 101(9):3178-3183 (2004).
McCaffrey, Anton P. et al., "A story of mice and men," Gene Therapy, vol. 9:1563 (2002).
McCaffrey, Anton P. et al., "RNA interference in adult mice," Nature, vol. 418:38-39 (2002).
McFadden, Sandra L. et al., "Anatomical, Metabolic and Genetic Aspects of Age-related Hearing Loss in Mice," Audiology, vol. 40:313-321 (2001).
McManus, Michael T. et al., "Gene Silencing in Mammals by Small Interfering RNAs," Nature Reviews Genetics, vol. 3:737-747 (2002).
McManus, Michael T. et al., "Gene silencing using micro-RNA designed hairpins," RNA, vol. 8:842-850 (2002).
Meister, Gunter et al., "Sequence-specific inhibition of microRNA- and siRNA-induced RNA silencing," RNA, vol. 10:544-550 (2004).
Merriam-Webster online, "engineer," retrieved online at http://www.merriam-webster.com/dictonary (2008).
Merriam-Webster online, "pharmaceutical," retrieved online at http://www.merriam-webster.com/dictonary (2009).
Mi, Zhibao et al., "Characterization of a Class of Cationic Peptides Able to Facilitate Efficient Protein Transduction in Vitro and in Vivo," Molecular Therapy, vol. 2(4):339-347 (2000).
Miller, Victor M. et al., "Allele-specific silencing of dominant disease genes," PNAS, vol. 100(12):7195-7200 (2003).
Miller, Victor M. et al., "Targeting Alzheimer's disease genes with RNA interference: an efficient strategy for silencing mutant alleles," Nucleic Acids Research, vol. 32(2):661-668 (2004).
Mitchell, D.J. et al., "Polyarginine enters cells more efficiently than other polycationic homopolymers," J. Peptide Res., vol. 56:318-325 (2000).
Miyagishi, Makoto et al., "U6 promoter-driven siRNAs with four uridine 3' overhangs efficiently suppress target gene expression in mammalian cells," Nature Biotechnology, vol. 19:497-500 (2002).
Molecular Biology of the Cell, Fourth Edition, "DNA Replication Mechanisms," retrieved online at http://www.ncbi.nlm.nih.gov/books/bv.fcgi?highlight=Dna&rid=mboc4.section-.754 (2008).
Moss, Eric G. et al., "The Cold Shock Domain Protein LIN-28 Controls Developmental Timing in C. elegans and Is Regulated by the lin-4 RNA," Cell, vol. 88:637-646 (1997).
Moss, Eric G., "Silencing unhealthy alleles naturally," Trends in Biotechnology, vol. 21(5):185-187 (2003).
Mourelatos, Zissimos et al., "miRNPs: a novel class of ribonucleoproteins containing numerous microRNAs," Genes & Development, vol. 16:720-728 (2002).
Mourrain, Philippe et al., "Arabidopsis SGS2 and SGS3 Genes Are Required for Posttranscriptional Gene Silencing and Natural Virus Resistance," Cell, vol. 101:533-542 (2000).
Muller, Jorn et al., "Severe testotoxicosis phentype associated with ASP578.Rtm. Tyr mutation of the lutrophin/choriogonadotrophin receptor gene," J. Med. Genet., vol. 35:340-341 (1998).
Murchison, Elizabeth P. et al., "miRNAs on the move: miRNA biogenesis and the RNAi machinery," Current Opinion in Cell Biology, vol. 16:223-229 (2004).
Nellemann, Christine et al., "Inhibition of Huntingtin Synthesis by Antisense Oligodeoxynucleotides," Molecular and Cellular Neuroscience, vol. 16:313-323 (2000).
Nykanen, Antti et al., "ATP Requirements and Small Interfering RNA Structure in the RNA Interference Pathway," Cell, vol. 107:309-321 (2001).
Oldridge, Michael et al., "Dominant mutations in ROR2, encoding an orphan receptor tyrosine kinase, cause brachydactyly type B," Nature Genetics, vol. 24:275-278 (2000).
Olsen, Philip H. et al., "The lin-4 Regulatory RNA Controls Developmental Timing in Caenorhabditis elegans by Blocking Lin-14 Protein Synthesis after the Initiation of Translation," Developmental Biology, vol. 216:671-680 (1999).
Opalinska et al., Nature Rev., vol. 1, pp. 503-514 (2002).
Opalinska, Joanna B. et al., "Nucleic Acid Therapeutic for Hematologic Malignancies--Theoretical Considerations," Ann. N.Y. Acad. Sci., vol. 1082:124-136 (2006).
Opalinska, Joanna B. et al., "Nucleic-Acid Therapeutics: Basic Principles and Recent Applications," Nature Reviews, Drug Discovery, vol. 1:503-514 (2002).
Orrell, Richard W. et al., "Clinical implications of the genetics of ALS and other motor neuron diseases," Neurology, vol. 57:9-17 (2001).
Paddison, Patrick J. et al., "Short hairpin RNAs (shRNAs) induce sequence-specific silencing in mammalian cells," Genes & Development, vol. 16:948-958 (2002).
Parrish, Susan et al., "Functional Anatomy of a dsRNA Trigger: Differential Requirement for the Two Trigger Strands in RNA Interference," Molecular Cell, vol. 6:1077-1087 (2000).
Paul, Cynthia P. et al., "Effective expression of small interfering RNA in human cells," Nature Biotechnology, vol. 29:505-508 (2002).
Peracchi et al., Rev. Med. Virol., vol. 14, pp. 47-64 (2004).
Persengiev, Stephan P. et al., "Nonspecific, concentration-dependent stimulation and repression of mammalian gene expression by small interfering RNAs (siRNAs)," RNA, vol. 10:12-18 (2004).
Pfister, Edith L. et al., "Five siRNAs Targeting Three SNPs May Provide Therapy for Three-Quarters of Huntington's Disease Patients," Current Biology, vol. 19:774-778 (2009).
Pooga, Margus et al., "Cell penetration by transportan," FASEB J., vol. 12:67-77 (1998).
Poy, Matthew N. et al., "A pancreatic islet-specific microRNA regulates insulin secretion," Nature, vol. 432:226-230 (2004).
Pusch, Oliver et al., "Nucleotide sequence homology requirements of Hiv-1-specific short hairpin RNA," Nucleic Acids Research, vol. 31(22):6444-6449 (2003).
Puttaparthi, Krishna et al., "Disease Progression in a Transgenic Model of Familial Amyotrophic Lateral Sclerosis Is Dependent on Both Neuronal and Non-Neuronal Zinc Binding Proteins," The Journal of Neuroscience, vol. 22 (20):8790-8796 (2002).
Qin, Zheng-Hong et al., "Autophagy regulates the processing of amino terminal huntingtin fragments," Human Molecular Genetics, vol. 12(24):3231-3244 (2003).
Radunovic, Aleksandar et al., "ALSODatabase: Database of SOD1 (and other) gene mutations in ALS on the internet," Amyot. Lat. Scler., vol. 1:45-49 (1999).
Ralph, G. Scott et al., "Silencing mutant SOD1 using RNAi protects against neurodegeneration and extends survival in an ALS model," Nature Medicine, vol. 11(4):429-433 (2005).

(56) References Cited

OTHER PUBLICATIONS

Raoul, Cedric et al., "Lentiviral-mediated silencing of SOD1 through RNA interference retards disease onset and progression in a mouse model of ALS," Nature Medicine, vol. 11(4):423-428 (2005).
Reich, Samuel J. et al., "Small interfering RNA (siRNA) targeting VEGF effectively inhibits ocular neovascularization in a mouse model," Molecular Vision, vol. 9:210-216 (2003).
Reinhart, Brenda J. et al., "MicroRNAs in plants," Genes & Development, vol. 16:1616-1626 (2002).
Reinhart, Brenda J. et al., "The 21-nucleotide let-7 Rna regulates developmental timing in Caenorhabditis elegans," Nature, vol. 403:901-906 (2000).
Reynolds, Angela et al., "Rational siRNA design for RNA interference," Nature Biotechnology, vol. 22(3):326330 (2004).
Rival, Thomas et al., "Decreasing Glutamate Buffering Capacity Triggers Oxidative Stress and Neuropil Degeneration in the Drosophila Brain," Current Biology, vol. 14:599-605 (2004).
Rose, Scott D. et al., "Functional polarity is introduced by Dicer processing of short substrate RNAs," Nucleic Acids Research, vol. 33(13):4140-4156 (2005).
Saenger, Wolfram, Principles of Nucleic Acid Struture, Springer-Verlag, New York, Charles R. Cantor (Ed.), 575 Pages, (1984).
Sahin-Toth, Miklos et al., "Gain-of-Function Mutations Associated with Hereditary Pancreatitis Enhance Autoactivation of Human Cationic Trypsinogen," Biochemical and Biophysical Research Communications, vol. 278:286-289 (2000).
Savitt, Joseph M. et al., "Diagnosis and treatment of Parkinson disease: molecules to medicine," The Journal of Clinical Investigation, vol. 116(7):1744-1754 (2006).
Saxena, Sandeep et al., "Small RNAs with Imperfect Match to Endogenous mRNA Repress Translation," The Journal of Biological Chemistry, vol. 278(45):44312-44319 (2003).
Scadden, A.D.J. et al., "Editing of RNA reduces the production of siRNAs," EMBO Reports, vol. 21(12):1109-1111 (2001).
Scherer, Lisa et al., "Therapeutic Applications of RNA Interference: Recent Advances in siRNA Design," Advances in Genetics, vol. 52:1-21 (2004).
Scherer, Lisa J. et al., "Approaches for the sequence-specific knockdown of mRNA," Nature Biotechnology, vol. 21 (12):1457-1465 (2003).
Scherer, Lisa J. et al., "Rapid Assessment of Anti-HIV siRNA Efficacy Using PCR-Derived Pol III shRNA Cassettes," Molecular Therapy, vol. 10(3):597-603 (2004).
Scherer, Lisa J. et al., "Recent Applications of RNAi in Mammalian Systems," Current Pharmaceutical Biotechnology, vol. 5:355-360 (2004).
Schmidt, Charlie, "Negotiating the RNAi patent thicket," Nature Biotechnology, vol. 25(3):273-275 (2007).
Schwarz, Dianne S. et al., "Asymmetry in the Assembly of the RNAi Enzyme Complex," Cell, vol. 115:199-208 (2003).
Schwarz, Dianne S. et al., "Designing siRNA That Distinguish between Genes That Differ by a Single Nucleotide," PLoS Genetics, vol. 2(9):1307-1318 (2006).
Schwarz, Dianne S. et al., "Evidence that siRNAs Function as Guides, Not Primers, in the Drosophila and Human RNAi Pathways," Molecular Cell, vol. 10:537-548 (2002).
Schwarz, Dianne S. et al., "The RNA-Induced Silencing Complex Is a Mg2+-Dependent Endonuclease," Current Biology, vol. 14:787-791 (2004).
Schwarz, Dianne S. et al., "Why do miRNAs live in the miRNP?," Genes & Development, vol. 16:1025-1031 (2002).
Seggerson, Kathy et al., "Two Genetic Circuits Repress the Caenorhabditis elegans Heterochronic Gene lin-28 after Translation Initiation," Developmental Biology, vol. 243:215-225 (2002).
Semizarov, D. et al., "Specificity of short interfering RNA determined through gene expression signatures," Pnas, vol. 100(11):6347-6352 (2003).
Shackel, Nick A. et al., "Intrahepatic Gene Silencing by RNA Interference," Gastroenterology, vol. 126(1):356-358 (2004).
Sharp, Phillip A. et al., "RNA Interference," Science, vol. 287:2431-2432 (2000).
Shefner, J.M. et al., "Mice lacking cytosolic copper/zinc superoxide dismutase display a distinctive motor axonopathy," Neurology, vol. 53:1239-1246 (1999).
Shi, Yang, "Mammalian RNAi for the masses," Trends in Genetics, vol. 19(1):9-12 (2003).
Siddique, Teepu et al., "Molecular genetic basis of familial ALS," Neurology, vol. 47(Suppl. 2):527-535 (1996).
Sijen, Titia et al., "One the Role of RNA Amplification in dsRNA-Triggered Gene Silencing," Cell, vol. 107:465- 476 (2001).
Simeoni, Federica et al., "Insight into the mechanism of the peptide-based gene delivery system MPG: implications for delivery of siRNA into mammalian cells," Nucleic Acids Research, vol. 31(11):2717-2724 (2003).
Simon, E.S. et al., "Creutzfeldt-Jakob Disease Profile in Pateints Homozygous for the PRNP E200K Mutation," Annals of Neurology, vol. 47(2):257-260 (2000).
Slack, Frank J. et al., "The lin-41 RBCC Gene Acts in the C. elegans Heterochronic Pathway between the let-7 Regulatory RNA and the LIN-29 Transcription Factor," Molecular Cell, vol. 5:659-669 (2000).
Sledz, Carol A. et al., "Activation of the interferon system by short-interfering RNAs," Nature Cell Biology, vol. 5 (9):834-838 (2003).
Snove, Ola Jr., et al., "Chemical Modifications Rescue Off-Target Effects of RNAi," ACS Chemical Biology, vol. 1 (5):274-276 (2006).
Song, Erwei et al., "RNA interference targeting Fas protects mice from fulminant hepatitis," Nature Medicine, vol. 9 (3):347-351 (2003).
Soutschek, Jurgen et al., "Therapeutic silencing of an endogenous gene by systemic administration of modified siRNAs," Nature, vol. 432:173-178 (2004).
Stark, Alexander et al., "Identification of Drosophila MicroRNA Targets," PLOS Biology, vol. 1(3):397-409 (2003).
Sui, Guangchao et al., "A DNA vector-based RNAi technology to suppress gene expression in mammalian cells," PNAS, vol. 99(8):5515-5520 (2002).
Sundaralingam, Muttaiya et al., "Hydrogen and hydration of DNA and RNA oligonucleotides," Biophysical Chemistry, vol. 95:273-282 (2002).
Supplementary European Search Report for Application No. 06836174, 6 pages, dated Dec. 10, 2008.
Supplementary European Search Report for Application No. 07810269.6, 7 pages, dated Oct. 19, 2010.
Supplementary Partial European Search Report for Application No. 04753972, 6 pages, dated Oct. 31, 2006.
Tabara, Hiroaki et al., "The dsRNA Binding Protein RDE-4 Interacts with RDE-1, DCR-1, and a DExH-Box Helicase to Direct RNAi in C. elegans," Cell, vol. 109:861-871 (2002).
Tabara, Hiroaki et al., "The rde-1 Gene, RNA Interference and Transposon Silencing in C. elegans," Cell, vol. 99:123-132 (1999).
Tan, P-H et al., "Gene knockdown with intrathecal siRNA of NMDA receptor NR2B subunit reduces formalin-induced nociception in the rat," Gene Therapy, vol. 12:59-66 (2005).
Tang, Guiliang et al., "A biochemical framework for RNA silencing in plants," Genes & Development, vol. 17:4963 (2003).
Tang, Guiliang et al., "Biochemical Dissection of RNA Silencing in Plants," Methods in Molecular Biology, vol. 257:223-243 (2004).
Taylor, J. Paul et al., "Toxic Proteins in Neurodegenerative Disease," Science, vol. 296:1991-1995 (2002).
Ten Asbroek, Anneloor L.M.A. et al., "Polymorphisms in the large subunit of human RNA polymerase II as target for allele-specific inhibition," Nucleic Acids Research, vol. 28(5):1133-1138 (2000).
Thakker, Deepak R. et al., "Neurochemical and behavioral consequences of widespread gene knockdown in the adult mouse brain by using nonviral RNA interference," PNAS, vol. 101(49):17270-17275 (2004).
Tijsterman, Marcel et al., "PPW-1, a PAZ/PIWI Protein Required for Efficient Germline RNAi, Is Defective in a Natural Isolate of C. elegans," Current Biology, vol. 12:1535-1540 (2002).

(56) References Cited

OTHER PUBLICATIONS

Tijsterman, Marcel et al., "RNA Helicase MUT-14-Dependent Gene Silencing Triggered in C. elegans by Short Antisense RNAs," Science, Vo. 295:694-697 (2002).
Tomari, Yukihide et al., "A Protein Sensor for siRNA Asymmetry," Science, vol. 306:1377-1380 (2004).
Tomari, Yukihide et al., "Perspective: machines for RNAi," Genes & Development, vol. 19:517-529 (2005).
Tomari, Yukihide et al., "RISC ASsembly Defects in the Drosophila RNAi Mutant armitage," Cell, vol. 116:831-841 (2004).
Tuschl, Thomas et al., "siRNAs and miRNAs," Keystone Symposia, Abstract Book (2004).
Tuschl, Thomas et al., "Small Interfering RNAs: A Revolutionary Tool for the Analysis of Gene Function and Gene Therapy," Molecular Interventions, vol. 2(3):158-167 (2002).
Tuschl, Thomas et al., "Targeted mRNA degradation by double-starnded RNA in vitro," Genes & Development, vol. 13:3191-3197 (1999).
Tuschl, Thomas, "Expanding small RNA interference," Nature Biotechnology, vol. 20:446-448 (2002).
Valdink, Jan H. et al., "The future of motor neuron disease," J. Neurol., vol. 241:491-500 (2004).
Van Bilsen, P.H.J. et al., "Identification and Allele-Specific Silencing of the Mutant Huntingtin Allele in Huntington's Disease Patient-Derived Fibroblasts," Human Gene Therapy, vol. 19:710-718 (2008).
Vargason, Jeffrey M. et al., "Size selective recognition of siRNA by an RNA silencing suppressor," Cell, vol. 115:799-811 (2003).
Vella, Monica C. et al., "The C. elegans microRNA let-7 binds to imperfect let-7 complementary sites from the lin-41 3'UTR," Genes & Development, vol. 18:132-137 (2004).
Victor, Martin et al., "HAT activity is essential for CBP-1-dependent transcription and differentiation in Caenorhabditis elegans," EMBO Reports, vol. 31(1):50-55 (2002).
Vives, Eric et al., "A Truncated HIV-1 Tat Protein Basic Domain Rapidly Translocates through the Plasma Membrane and Accumulates in the Cell Nucleus," The Journal of Biological Chemistry, vol. 272(25):16010-16017 (1997).
Wang, J. et al., "Fas siRNA Reduces Apoptotic Cell Death of Allogeneic-Transplanted Hepatocytes in Mouse Spleen," Transplantation Proceedings, Vo. 35:1594-1595 (2003).
Wang, Yu-Lai et al., "Clinico-pathological rescue of a model mouse of Huntington's disease by siRNA," Neuroscience Research, vol. 53:241-249 (2005).
Wianny, Florence et al., "Specific interference with gene function by double-stranded RNA in early mouse development," Nature Cell Biology, vol. 2:70-75 (2000).
Wightman, Bruce et al., "Posttranscriptional Regulation of the Heterochronic Gene lin-14 by lin-4 Mediates Temporal Pattern Formation in C. elegans," Cell, vol. 75:855-862 (1993).
Wikipedia, "Human genetic variation," obtained online at: http://en.wikipedia.org/wiki/Human.sub.--genetic-variation (2008).
Wu-Sharf, Dancia et al., "Transgene and Transposon Silencing in Chlamydomonas reinhardtii by a DEAH-Box RNA Helicase," Science, vol. 290:1159-1162 (2000).
Xia, Haibin et al., "siRNA-mediated gene silencing in vitro and in vivo," Nature Biotechnology, vol. 20:1006-1010 (2002).
Xia, Xu Gang et al., "An enhanced U6 promoter for synthesis of short hairpin RNA," Nucleic Acids Research, vol. 31 (17):e100 (2003).
Xia, Xu Gang et al., "An RNAi strategy for treatment of amyotrophic lateral sclerosis caused by mutant Cu,Zn superoxide dismutase," Journal of Neurochemistry, vol. 92:362-367 (2005).
Xie, Jun et al., "RNAi knockdown of Par-4 inhibits neurosynaptic degeneration in ALS-linked mice," Journal of Neurochemistry, vol. 92:59-71 (2005).
Xie, Zhongcong et al., "Effects of RNA Interference-mediated Silencing of g-Secretase Complex Components on Cell Sensitivity to Caspase-3 Activation," The Journal of Biological Chemistry, vol. 279(33):34130-34137 (2004).
Xu, Peizhang et al., "The Drosophila MicroRNA Mir-14 Suppresses Cell Death and Is Required for Normal Fat Metabolism," Current Biology, vol. 13:790-795 (2003).
Yi, Rui et al., "Exportin-5 mediates the nuclear export of pre-microRNAs and short hairpin RNAs," Genes & Development, vol. 17:3011-3016 (2003).
Yohrling, George J. et al., "Mutant huntingtin increases nuclear corepressor function and enhances ligand-dependent nuclear hormone receptor activation," Molecular and Cellular Neuroscience, vol. 23:28-38 (2003).
Yu, Jenn-Yah et al., "RNA interference by expression of short-interfering RNAs and hairpin RNAs in mammalian cells," PNAS, vol. 99(9):6047-6052 (2002).
Zamore, Phillip D. et al., "RNAi: Double-Stranded RNA Directs the ATP-Dependent Cleavage of mRNA at 21 to 23 Nucleotide Intervals," Cell, vol. 101:25-33 (2000).
Zamore, Phillip D. et al., "siRNAs knock down hepatitis," Nature Medicine, vol. 9(3):266-267 (2003).
Zeng, Yan et al, "Sequence requirements for micro RNA processing and function in human cells," RNA, vol. 9:112-123 (2003).
Zeng, Yan et al., "Both Natural and Designed Micro RNAs Can Inhibit the Expression in Cognate mRNAs When Expressed in Human Cells," Molecular Cell, vol. 9:1327-1333 (2002).
Zeng, Yan et al., "MicroRNAs and small interfering RNAs can inhibit mRNA expression by similar mechanisms," Pnas, vol. 100(17):9779-9784 (2003).
Zeng, Yan et al., "Structural requirements for pre-microRNA binding and nuclear export by Exportin 5," Nucleic Acids Research, vol. 32(16):4776-4785 (2004).
Zhang, Haidi et al., "Human Dicer preferentially cleaves dsRNAs at their termini without a requirement for ATP," The EMBO Journal, vol. 21(21):5875-5885 (2002).
Zhang, J. et al., "Targeted Gene Silencing by Small Interfering RNA-Based Knock-Down Technology," Current Pharmaceutical Biotechnology, vol. 5:1-7 (2004).
Zhang, Yingjie et al., "Engineering Mucosal RNA Interference in Vivo," Molecular Therapy, vol. 14(3):336-342 (2006).
Zhou, Hongxia et al., "An RNA polymerase II construct synthesizes short-hairpin RNA with a quantitative indicator and mediates highly efficient RNAi," Nucleic Acids Research, vol. 33(6):e62, 8 pp., (2005).
Zimmermann, Tracy S. et al, "RNAi-mediated Gene Silencing in Non-human Primates," Nature, vol. 441, 111-114 (2006).
Zitzmann, Sabine et al., "Arginine-Glycine-Aspartic Acid (RGD)-Peptide Binds to Both Tumor and Tumor-Endothelial Cells in Vivo," Cancer Research, vol. 62:5139-5143 (2002).
Zuccato, Chiara et al., "Loss of Huntingtin-Mediated BDNF Gene Transcription in Huntington's Disease," Science, vol. 293:493-498 (2001).
Molecular Biology of the Cell, Fourth Edition, "Figure 4-4," retrieved online at http://www.ncbi.nlm.nih.gov/books/bv.fcgi?rid=mboc4.figgrp (2008).
Molecular Biology of the Cell, Fourth Edition, "The Chemical Composition of a Cell," retrieved online at http://www.ncbi.nlm.nih.gov/books/bv.fcgi?highlight-hydrogen,dna,bond&hd-mboc4.section185 (2008).
Molecular Biology of the Cell, Fourth Edition, "Wobble base-pairing between codons and anticodons," retrieved online at http://www.ncbi.nlm.nih.gov/books/bv.fcgi?highlight=lnosIne&rld=mboc4.figgrp.1058 (2008).

* cited by examiner

FIG. 1A

| | | | | |
|---|---|---|---|---|
| 1 | TTGCTGTGTG | AGGCAGAACC | TGCGGGGGCA | GGGGCGGGCT | GGTTCCCTGG | CCAGCCATTG |
| 61 | GCAGAGTCCG | CAGGCTAGGG | CTGTCAATCA | TGCTGGCCCG | CGTGGCCCCG | CCTCCGCCCG |
| 121 | CGCGGCCCCG | CCTCCGCCCG | CGCACGTCTG | GGACGCAAGG | CGCCGTGGGG | GCTGCCGGGA |
| 181 | CGGGTCCAAG | ATGGACGGCC | GCTCAGGTTC | TGCTTTTACC | TGCGGCCCAG | AGCCCCATTC |
| 241 | ATTGCCCCGG | TGCTGAGCGG | CGCCGCGAGT | CGGCCCGAGG | CCTCCGGGGA | CTGCCGTGCC |
| 301 | GGGCGGGAGA | CCGCCATGGC | GACCCTGGAA | AAGCTGATGA | AGGCCTTCGA | GTCCCTCAAG |
| 361 | TCCTTCCAGC | AGCAGCAGCA | GCAGCAGCAG | CAGCAGCAGC | AGCAGCAGCA | GCAGCAGCAG |
| 421 | CAGCAGCAGC | AACAGCCCGC | ACCGCCCCCG | CCGCCGCCCG | CGCCTCCTCA | GCTTCCTCAG |
| 481 | CCGCCGCCGC | AGGCACACCT | GCTGCTGCCT | CAGCCGCAGC | CCGCCGCAGC | GCCGCCCCCG |
| 541 | CCGCCACCCG | GCCCGGCTGT | GGCTGAGGAG | CCGCTGCACC | CGCCGCCACC | AGAACTTTCA |
| 601 | GCTACCAAGA | AAGACCGTGT | GAATCATTGT | CTGACAATAT | GTGAAAACAT | AGTGGCACAG |
| 661 | TCTGTCAGAA | ATTCTCCAGA | ATTTCAGAAA | CTTCTGGGCA | TCGCTATGGA | ACTTTTTCTG |
| 721 | CTGTGCAGTG | ATGACGCAGA | GTCAGATGTC | AGGATGGTGG | CTGACGAATG | CCTCAACAAA |
| 781 | GTTATCAAAG | CTTTGATGGA | TTCTAATCTT | CCAAGGTTAC | AGCTCGAGCT | CTATAAGGAA |
| 841 | ATTAAAAAGA | ATGGTGCCCC | TCGGAGTTTG | CGTGCTGCCC | TGTGGAGGTT | TGCTGAGCTG |
| 901 | GCTCACCTGG | TTCGGCCTCA | GAAATGCAGG | CCTTACCTGG | TGAACCTTCT | GCCGTGCCTG |
| 961 | ACTCGAACAA | GCAAGAGACC | CGAAGAATCA | GTCCAGGAGA | CCTTGGCTGC | AGCTGTTCCC |
| 1021 | AAAATTATGG | CTTCTTTTGG | CAATTTTGCA | AATGACAATG | AAATTAAGGT | TTTGTTAAAG |
| 1081 | GCCTTCATAG | CGAACCTGAA | GTCAAGCTCC | CCCACCATTC | GGCGGACAGC | GGCTGGATCA |
| 1141 | GCAGTGAGCA | TCTGCCAGCA | CTCAAGAAGG | ACACAATATT | TCTATAGTTG | GCTACTAAAT |
| 1201 | GTGCTCTTAG | GCTTACTCGT | TCCTGTCGAG | GATGAACACT | CCACTCTGCT | GATTCTTGGC |

FIG.1B

```
1261  GTGCTGCTCA  CCCTGAGGTA  TTTGGTGCCC  TTGCTGCAGC  AGCAGGTCAA  GGACACAAGC
1321  CTGAAAGGCA  GCTTCGGAGT  GACAAGGAAA  GAAATGGAAG  TCTCTCCTTC  TGCAGAGCAG
1381  CTTGTCCAGG  TTTATGAACT  GACGTTACAT  CATACACAGC  ACCAAGACCA  CAATGTTGTG
1441  ACCGGAGCCC  TGGAGCTGTT  GCAGCAGCTC  TTCAGAACGC  CTCCACCCGA  GCTTCTGCAA
1501  ACCCTGACCG  CAGTCGGGGG  CATTGGGCAG  CTCACGCTG   CTAAGGAGGA  GTCTGGTGCC
1561  CGAAGCCGTA  GTGGGAGTAT  TGTGGAACTT  ATAGCTGGAG  GGGGTTCCTC  ATGCAGCCCT
1621  GTCCTTTCAA  GAAAACAAAA  AGGCAAAGTG  CTCTTAGGAG  AAGAAGAAGC  CTTGGAGGAT
1681  GACTCTGAAT  CGAGATCGGA  TGTCAGCAGC  TCTGCCTTAA  CAGCCTCAGT  GAAGGATGAG
1741  ATCAGTGGAG  AGCTGGCTGC  TTCTTCAGG   GTTTCCACTC  CAGGGTCAGC  AGGTCATGAC
1801  ATCATCACAG  AACAGCCACG  GTCACAGCAC  ACACTGCAGG  CGGACTCAGT  GGATCTGGCC
1861  AGCTGTGACT  TGCCACTGAGC TGCCACTGAT GGGGATGAGG  AGGATATCTT  GAGCCACAGC
1921  TCCAGCCAGG  TCAGCGCCGT  CCCATCTGAC  CCTGCCATGG  ACCTGAATGA  TGGGACCCAG
1981  GCCTCGTCGC  CCATCAGCGA  CAGCTCCCAG  TCTCAACAGG  AAGGGCCTGA  TTCAGCTGTT
2041  ACCCCTTCAG  ACAGTTCTGA  AATTGTGTTA  GACGGTACCG  ACAACCAGTA  TTTGGGCCTG
2101  CAGATTGGAC  AGCCCCAGGA  TGAAGATGAG  GAAGCCACAG  GTATTCTTCC  TGATGAAGCC
2161  TCGGAGGCCT  TCAGGAACTC  TTCCATGGCC  CTTCAACAGG  CACATTTATT  GAAAAACATG
2221  AGTCACTGCA  GGCAGCCTTC  TGACAGCAGT  AAACAAGCCT  GTTGATAAAT  TTGTGTTGAG  AGATGAAGCT
2281  ACTGAACCG   GTGATCAAGA  TCTTGTCCAC  TCTTGTCCAT  TGCCCGCATCA  AAGGTGACAT  TGGACAGTCC
2341  ACTGATGATG  ACTCTGCACC  TCTTGTCCAC  AAGGTGACAT  TTTTATCTGC  TTCGTTTTTG
2401  CTAACAGGGG  GAAAAAATGT  GCTGGTTCCG  TGCCCGCATCA  TGAGGGTCAG  CGTGAAGCC
2461  CTGGCCCTCA  GCTGTGTGGG  AGCAGCTGTG  GCCCTCCACC  CGGAATCTTT  CTTCAGCAAA
```

FIG.1C

```
2521  CTCTATAAAG  TTCCTCTTGA  CACCACGGAA  TACCCTGAGG  AACAGTATGT  CTCAGACATC
2581  TTGAACTACA  TCGATCATGG  AGACCCACAG  GTTCGAGGAG  CCACTGCCAT  TCTCTGTGGG
2641  ACCCTCATCT  GCTCCATCCT  CAGCAGGTCC  CGCTTCCACG  TGGGAGATTG  GATGGGCACC
2701  ATTAGAACCC  TCACAGGAAA  TACATTTTCT  TTGGCGGATT  GCATTCCTTT  GCTGCGGAAA
2761  ACACTGAAGG  ATGAGTCTTC  TGTTACTTGC  AAGTTAGCTT  GTACAGCTGT  GAGGAACTGT
2821  GTCATGAGTC  TCTGCAGCAG  CAGCTACAGT  GAGTTAGGAC  TGCAGCTGAT  CATCGATGTG
2881  CTGACTCTGA  GGAACAGTTC  CTATTGGCTG  GTGAGGACAG  AGCTTCTGGA  AACCCTTGCA
2941  GAGATTGACT  TCAGGCTGGT  GAGCTTTTTG  TTTAAAAACTG  CAGAAAACTT  ACACAGAGGG
3001  GCTCATCATT  ATACAGGGCT  TTTAAAAACTG  CAAGAACGAG  TGCTCAATAA  TGTTGTCATC
3061  CATTGCTTG   GAGATGAAGA  CCCAGGGTG   CGACATGTTG  CCGCAGCATC  ACTAATTAGG
3121  CTTGTCCCAA  AGCTGTTTTA  TAAATGTGAC  CAAGGACAAG  CTGATCCAGT  AGTGGCCGTG
3181  GCAAGAGATC  AAAGCAGTGT  TTACCTGAAA  CTTCTCATGC  ATGAGACGCA  GCCTCCATCT
3241  CATTTCTCCG  TCAGCACAAT  AACCAGAATA  TATAGAGGCT  ATAACCTACT  ACCAAGCATA
3301  ACAGACGTCA  CTATGGAAAA  TAACCTTTCA  AGAGTTATTG  CAGCAGTTTC  TCATGAACTA
3361  ATCACATCAA  CCACCAGAGC  ACTCACATTT  GGATGCTGTG  AAGCTTTGTG  TCTTCTTTCC
3421  ACTGCCTTCC  CAGTTTGCAT  TTGGAGTTTA  GGTTGGCACT  GTGGAGTGCC  TCCACTGAGT
3481  GCCTCAGATG  AGTCTAGGAA  GAGCTGTACC  GTTGGGATGG  CCACAATGAT  TCTGACCCTG
3541  CTCTCGTCAG  CTTGGTTCCC  ATTGGATCTC  TCAGCCCATC  AAGATGCTTT  GATTTTGGCC
3601  GGAAACTTGC  TTGCAGCCAG  TGCTCCCAAA  CAAGCAAGAG  GTTCATGGGC  CTCTGAAGAA
3661  GAAGCCAACC  CAGCAGCCAC  CAAGCAAGAG  GAGGTCTGGC  CAGCCCTGGG  GGACCGGGCC
3721  CTGGTGCCCA  TGGTGGAGCA  GCTCTCTCT   CACCTGCTGA  AGGTGATTAA  CATTTGTGCC
```

```
3781  CACGTCCTGG ATGACGTGGC TCCTGGACCC GCAATAAAGG CAGCCTTGCC TTCTCTAACA
3841  AACCCCCCTT CTCTAAGTCC CATCCGACGA AAGGGGAAGG AGAAAGAACC AGGAGAACAA
3901  GCATCTGTAC CGTTGAGTCC CAAGAAAGGC AGTGAGGCCA GTGCAGCTTC TAGACAATCT
3961  GATACCTCAG GTCCTGTTAC AACAAGTAAA TCCTCATCAC TGGGGAGTTT CTATCATCTT
4021  CCTTCATACC TCAAACTGCA AAAGCTACAC ACGCTAACTA CAAGGTCACG
4081  CTGGATCTTC AGAACAGCAC GGAAAAGTTT GGAGGGTTTC CTTGGATGTT
4141  CTTTCTCAGA TACTAGAGCT GGCCACACTG CAGGACATTG TCCGCTCAGC
4201  CTAGGATACC CGTTGAGTCG CTTTAGTCGA GAAGTGTGT TGAAGAGATC
4261  CAATTGTTGA AGACTCTCTT TGGCACAAAC TTTGGCCTCC AGTTTGATGG CTTATCTTCC
4321  AACCCCAGCA AGTCACAAGG CCGAGCACAG CGCCTTGGCT CCTCCAGTGT GAGGCCAGGC
4381  TTGTACCACT ACTGCTTCAT GGCCCCGTAC ACCCACTTCA CCCAGGCCCT CGCTGACGCC
4441  AGCTGAGGA ACATGGTGCA GGCGGAGCA CCTCGGGATG GTTGATGTC
4501  CTCCAGAAAG TGTCTACCCA GTTGAAGACA AACCTCACGA GTGTCACAAA GAACCGTGCA
4561  GATAAGAATG CTATTCATAA TCACATTCGT CTCTTGTTAT AAAAGCTTTA
4621  AAACAGTACA CGACTACAAC ATGTGTGCAG TTACAGAAGC AGGTTTTAGA TTTGCTGGCG
4681  CAGCTGGTTC AGTTACGGGT TAATTACTGT CTTCTGGATT CAGATCAGGT GTTTATTGGC
4741  TTTGTATTGA AACAGTTGA ATACATTGAA GTGGGCCAGT TCAGGGAATC AGAGGCAATC
4801  ATTCCAAACA TCTTTTTCTT CTTGGTATTA CTATCTTATG AACGCTATCA TTCAAAACAG
4861  ATCATTGGAA TTCCTAAAAT CATTCAGCTC TGTGATGGCA TCATGGCCAG TGGAAGGAAG
4921  GCTGTGACAC ATGCCATACC GGCTCTGCAC CCCATAGTCC ACGACCTCTT TGTATTAAGA
4981  GGAACAAATA AAGCTGATGC AGGAAAAGAG CTTGAAACCC AAAAAGAGGT GGTGGTGTCA
```

```
5041  ATGTTACTGA GACTCATCCA GTACCATCCAG AGACAAGTGG AGACAAGATGT AGCTGACATC
5101  CAGTGCCACA AGGAGAATGA AGACAAGTGG AGACAAGATGT AGCTGACATC
5161  ATCCTCCCAA TGTTAGCCAA ACAGCAGATG CACATTGACT CTCATGAAGC CCTTGGAGTG
5221  TTAAATACAT TATTTGAGAT TTTGGCCCCT TCCTCCCTCC GTCCGGTAGA CATGCTTTTA
5281  CGGAGTATGT TCGTCACTCC AAACACAATG GCGTCCGTGA GCACTGTTCA ACTGTGGATA
5341  TCGGGAATTC TGGCCATTTT GAGGGTTCTG ATTTCCCAGT CAACTGAAGA TATTGTTCTT
5401  TCTCGTATTC AGGAGCTCTC CTTCTCTCCG TATTTAATCT CCTGTACAGT AATTAATAGG
5461  TTAAGAGATG GGGACAGTAC TTCAACGCTA GAAGAACACA GTGAAGGGAA ACAAATAAAG
5521  AATTTGCCAG AAGAAACATT TTCAAGGTTT CTATTACAAC TGGTTGGTAT TCTTTTAGAA
5581  GACATTGTTA CAAAACAGCT GAAGGTGGAA ATGAGTGAGC AGCAACATAC TTTCTATTGC
5641  CAGGAACTAG GCACACTGCT AATGTGTCTG ATCCACATCT TCAAGTCTGG AATGTTCCGG
5701  AGAATCACAG CAGCTGCCAC TAGGCTGTTC CGCAGTGATG GCTGTGGCGG CAGTTTCTAC
5761  ACCCTGGACA GCTTGAACTT GCGGGCTCGT TCCATGATCA CCACCCACCC GGCCCTGGTG
5821  CTGCTCTGGT GTCAGATACT GCTGCTTGTC AACCACACCG ACTACCGCTG GTGGGCAGAA
5881  GTGCAGCAGA CCCCGAAAAG ACACAGTCTG TCCAGCACAA AGTTACTTAG TCCCCAGATG
5941  TCTGGAGAAG AGGAGGATTC TGACTTGGCA GCCAAACTTG GAATGTGCAA TAGAGAAATA
6001  GTACGAAGAG GGGCTCTCAT TCTCTTCTGT GATTATGTCT GTCAGAACCT CCATGACTCC
6061  GAGCACTTAA CGTGGCTCAT TGTAAATCAC ATTCAAGATC TGATCAGCCT TTCCCACGAG
6121  CCTCCAGTAC AGGACTTCAT CAGTGCCGTT CATCGGAACT CTGCTGCCAG CGGCCTGTTC
6181  ATCCAGGCAA TTCAGTCTCG TTGTGAAAAC CTTTCAACTC CAACCATGCT GAAGAAAACT
6241  CTTCAGTGCT TGGAGGGGAT CCAATCTCAGC CAGTCGGGAG CTGTGCTCAC GCTGTATGTG
```

```
6301 GACAGGCTTC TGTGCACCCC TTTCCGTGTG CTGGCTCGCA TGGTCGACAT CCTTGCTTGT
6361 CGCCGGGTAG AAATGCTTCT GGCTGCAAAT TTACAGAGCA GCATGGCCCA GTTGCCAATG
6421 GAAGAACTCA ACAGAATCCA GGAATACCTT CAGAGCAGCG GGCTCGCTCA GAGACACCAA
6481 AGGCTCTATT CCCTGCTGGA CAGGTTTCGT CTCTCCACCA TGCAAGACTC ACTTAGTCCC
6541 TCTCCTCCAG TCTCTTCCCA CCCGCTGGAC GGGGATGGGC ACGTGTCACT GGAAACAGTG
6601 AGTCCGGACA AAGACTGGTA CGTTCATCTT GTCAAATCCC AGTGTTGGAC CAGGTCAGAT
6661 TCTGCACTGC TGGAAGGTGC AGAGCTGGTG AATCGGATTC CTGCTGAAGA TATGAATGCC
6721 TTCATGATGA ACTCGGAGTT CAACCTAAGC CTGCTAGCTC CATGCTTAAG CCTAGGGATG
6781 AGTGAAATTT CTGGTGGCCA GAAGAGTGCC CTTTTTGAAG CAGCCCGTGA GGTGACTCTG
6841 GCCCGTGTGA GCGGCACCGT GCAGCAGCTC CCTGCTGTCC ATCATGTCTT CCAGCCCGAG
6901 CTGCCTGCAG AGCCGGCGGC CTACTGGAGC AAGTTGAATG ATCTGTTTGG GGATGCTGCA
6961 CTGTATCAGT CCCTGCCCAC TCTGGCCCGG GCCCTGGCAC AGTACCTGGT GGTGGTCTCC
7021 AAACTGCCCA GTCATTTGCA CCTTCCTCCT GAGAAAGAGA AGGACATTGT GAAATTCGTG
7081 GTGGCAACCC TTGAGGCCCT GTCCTGGCAT GTCGATCCATG AGCAGATCCC GCTGAGTCTG
7141 GATCTCCAGG CAGGGCTGGA CTGCTGCTGC GCCCTGCTGG AGCTGCCTGG CCTCTGGAGC
7201 GTGGTCTCCT CCACAGAGTT TGTGACCCAC GCCTGCTCCC TCATCTACTG TGTGCACTTC
7261 ATCCTGGAGG CCGTTGCAGT GCAGCCTGGA GAGCAGCTTC TTAGTCCAGA AAGAAGGACA
7321 AATACCCCAA AAGCCATCAG CGAGGAGGAG GAGGAAGTAG ATCCAAACAC ACAGAATCCT
7381 AAGTATATCA CTGCAGCCTG TGAGATGGTG GCAGAAATGG TGGAGTCTCT GCAGTCGGTG
7441 TTGGCCTTGG GTCATAAAAG GAATAGCGGC GTGCCGGCGT TTCTCACGCC ATTGCTCAGG
7501 AACATCATCA TCAGCCTGGC CCGCCTGCCC CTTGTCAACA GCTACACACG TGTGCCCCCA
```

```
7561 CTGGTGTGGA AGCTTGGATG GTCACCCAAA CCGGGAGGGG ATTTTGGCAC AGCATTCCCT
7621 GAGATCCCCG TGGAGTTCCT CCAGGAAAAG GAAGTCTTTA AGGAGTTCAT CTACCGCATC
7681 AACACACTAG GCTGGACCAG TCGTACTCAG TTTGAAGAAA CTTGGGCCAC CCTCCTTGGT
7741 GTCCTGGTGA CGCAGCCCCT CGTGATGGAG CAGGAGGAGA GCCCACCAGA AGAAGACACA
7801 GAGAGGACCC AGATCAACGT CCTGGCCGTG CAGGCCATCA CCTCACTGGT GCTCAGTGCA
7861 ATGACTGTGC CTGTGCCCGG CAACCCAGCT GTAAGCTGCT TGGAGCAGCA GCCCCGGAAC
7921 AAGCCCTCGA AAGCTCTCGA CACCAGGTTT GGGAGGAAGC TGAGCATTAT CAGAGGGATT
7981 GTGGAGCAAG AGATTCAAGC AATGGTTTCA AAGAGAGAGA ATATTGCCAC CCATCATTTA
8041 TATCAGGCAT GGGATCCTGT CCCTTCTCTG TCTCCGGCTA CTACAGGTGC CCTCATCAGC
8101 CACGAGAAGC TGCTGCTACA GATCAACCCC GAGCGGGAGC TGGGGAGCAT GAGCTACAAA
8161 CTCGGCCAGG TGTCCATACA CTCCGTGTGG CTGGGGAACA GCATCACACC CCTGAGGGAG
8221 GAGGAATGGG ACGAGGAAGA GGAGGAGGAG GCCGACGCCC CTGCACCTTC GTCACCACCC
8281 ACGTCTCCAG TCAACTCCAG GAAACACCGG GCTGGAGTTG ACATCCACTC CTGTTCGCAG
8341 TTTTTGCTTG AGTTGTACAG CCCTGGATC CTGCCGTCCA GCTCAGCCAG GAGGACCCCG
8401 GCCATCCTGA TCAGTGAGGT GGTCAGATCC CTTCTAGTGG TCTCAGACTT GTTCACCGAG
8461 CGCAACCAGT TTGAGCTGAT GTATGTGACG CTGACAGAAC TGCCAAGGGT GCACCCTTCA
8521 GAAGACGAGA TCCTCGCTCA GTACCTGGTG CCTGCCACCT GCAAGGCAGC TGCCGTCCTT
8581 GGGATGGACA AGGCCGTGGC GGAGCCTGTC AGCCGCCTGC TGGAGAGCAC GCTCAGGAGC
8641 AGCCACCTGC CCAGCAGGGT TGGAGCCCTG CACGGCGTCC TCTATGTGCT GGAGTGCGAC
8701 CTGCTGGACG ACACTGCCAA GCAGCTCATC CGGTCATCA GCGACTATCT CCTCTCCAAC
8761 CTGAAAGGGA TCGCCCACTG CACAGCCAGC AGCACGTACT GGTCATGTGT
```

FIG. 1H

```
8821   GCCACTGCGT TTTACCTCAT TGAGAACTAT CCTCTGGACG TAGGGCCGGA ATTTTCAGCA
8881   TCAATAATAC AGATGTGTGG GGTGATGCTG TCTGGAAGTG AGGAGTCCAC CCCCTCCATC
8941   ATTTACCACT GTGCCCTCAG AGGCCTGGAG CGCCTCCTGC TCTCTGAGCA GCTCTCCCGC
9001   CTGGATGCAG AATCGCTGGT CAAGCTGTGT GTGGACAGAG CGGACAGTGCA CAGCCCGCAC
9061   CGGGCCATGG CGGCTCTGGG CCTGATGCTC ACCTGCATGT TGAACGTGCA GGAGAAAGTC
9121   AGTCCGGGTA GAACTTCAGA CCCTAATCCT GCAGCCCCCG ACAGCGAGTC AGTGATTGTT
9181   GCTATGGAGC GGGTATCTGT TCTTTTTGAT AGGATCAGGA AAGGCTTTCC TTGTGAAGCC
9241   AGAGTGGTGG CCAGGATCCT GCCCCAGTTT CTAGACGACT TCTTCCCACC CCAGGACATC
9301   ATGAACAAAG TCATCGGAGA GTTTCTGTCC AACCAGCAGC CATACCCCCA GTTCATGGCC
9361   ACCGTGGTGT ATAAGGTGTT TCAGACTCTG CACAGCACCG GCCAGTCGTC CATGGTCCGG
9421   GACTGGGTCA TGCTGTCCCT CTCCAACTTC ACGCAGAGGG CCCCGGTCGC CATGGCCACG
9481   TGGAGCCCTCT CCTGCTTCTT TGTCAGCGCG TCCACCAGCC CGTGGGTCGC GGCGATCCTC
9541   CCACATGTCA TCAGCAGGAT GGGCAAGCTG GAGCAGGTGG ACGTGAACCT TTTCTGCCTG
9601   GTCGCCACAG ACTTCTACAG ACACCAGATA GAGGAGGAGC TCGACCGCAG GGCCTTCCAG
9661   TCTGTGCTTG AGGTGGTTGC AGCCCCAGGA AGCCCATATC ACCGGCTGCT GACTTGTTTA
9721   CGAAATGTCC ACAAGGTCAC CACCTGCTGA GCGCCATGGT GGGAGAGACT GTGAGGCGGC
9781   AGCTGGGGCC GGAGCCTTTG GAAGTCTGTG CCCTTGTGCC CTGCCTCCAC CGAGCCAGCT
9841   TGGTCCCTAT GGGCTTCCGC ACATGCCGCG GCGGCCAGG CAACGTCTGT GTCTCTGCCA
9901   TGTGGCAGAA GTGTCTTTG TGGCAGTGGC CAGGCAGGGA GTGTCTGCAG TCCTGGTGGG
9961   GCTGAGCCTG AGGCCTTCCA GAAAGCAGGA GCAGCTGTGC TGCACCCCAT GTGGGTGACC
10021  AGGTCCTTTC TCCTGATAGT CACCTGCTGG GTTGCAGCTG CTCTTGCATC
```

```
10081  TGGGCCAGAA  GTCCTCCCTC  CTGCAGGCTG  GCTGTTGGCC  CCTCTGCTGT  CCTGCAGTAG
10141  AAGGTGCCGT  GAGCAGGCTT  TGGGAACACT  GCCCTGGGTC  TCCCTGGTGG  GGTGTGCATG
10201  CCACGCCCCG  TGTCTGGATG  CACAGATGCC  ATGGCCTGTG  CTGGGCCAGT  GGCTGGGGGT
10261  GCTAGACACC  CGGCACCATT  CTCCCTTCTC  TCTTTTCTTC  TCAGGATTTA  AAATTTAATT
10321  ATATCAGTAA  AGAGATTAAT  TTTAACGAAC  TCTTTCTATG  CCCGTGTAAA  GTATGTGAAT
10381  CGCAAGGCCT  GTGCTGCATG  CGACAGCGTC  CGGGGTGGTG  GACAGGGCCC  CCGGCCACGC
10441  TCCCTCTCCT  GTAGCCACTG  GCATAGCCCT  CCTGAGCACC  CGCTGACATT  TCCGTTGTAC
10501  ATGTTCCTGT  TTATGCATTC  ACAAGGTGAC  TGGGATGTAG  AGAGGCGTTA  GTGGGCAGGT
10561  GGCCACAGCA  GGACTGAGGA  CAGGCCCCCA  TTATCCTAGG  GGTGCGCTCA  ACTGCAGCCC
10621  CTCCCTCCTG  GGCACAGACG  ACTGTCGTTC  TCCACCCACC  AGTCAGGGAC  AGCAGCCTCC
10681  CTGTCACTCA  GCTGAGAAGG  CCAGCCCTCC  CTGGCTGTGA  GCAGCCTCCA  CTGTGTCCAG
10741  AGACATGGGC  CTCCCACTCC  TGTTCCTTGC  TAGCCCTGGG  GTGGCCGTCTG  CCTAGGAGCT
10801  GGCTGGCAGG  TGTTGGGACC  TGCTGCTCCA  TGGATGCATG  CCCTAAGAGT  GTCACTGAGC
10861  TGTGTTTTGT  CTGAGCCTCT  CTCGGTCAAC  AGCAAAGCTT  GGTGTCTTGG  CACTGTTAGT
10921  GACAGAGCCC  AGCATCCCTT  CTGCCCCCGT  TCCAGCTGAC  ATCTTGCACG  GTGACCCCTT
10981  TTAGTCAGGA  GAGTGCAGAT  CTGTGCTCAT  CGGAGACTGC  CCCACGGCCC  TGTCAGAGCC
11041  GCCACTCCTA  TCCCCAGGAC  AGGTCCCTGG  ACCAGCCTCC  TGTTTGCAGG  CCCAGAGGAG
11101  CCAAGTCATT  AAAATGGAAG  TGGATTCTGG  ATGGCCGGGC  TGCTGCTGAT  GTAGGAGCTG
11161  GATTTGGGAG  CTCTGCTTGC  CGACTGGCTG  TGAGACGAGG  CAGGGCTCT  GCTTCCTCAG
11221  CCCTAGAGGC  GAGCCAGGCA  AGTTGGCGA  CTGTCATGTG  GCTTGGTTTG  GTCATGCCCG
11281  TCGATGTTTT  GGGTATTGAA  TGTGGTAAGT  GGAGGAAATG  TTGGAACTCT  GTGCAGGTGC
```

FIG.11

```
11341  TGCCTTGAGA  CCCCCAAGCT  TCCACCTGTC  CCTCTCCTAT  GTGGCAGCTG  GGGAGCAGCT
11401  GAGATGTGGA  CTTGTATGCT  GCCCACATAC  GTGAGGGGGA  GCTGAAAGGG  AGCCCCTGCT
11461  CAAAGGGAGC  CCCTCCTCTG  AGCAGCCTCT  GCCAGGCCTG  TATGAGGCTT  TTCCCACCAG
11521  CTCCCAACAG  AGGCCTCCCC  CAGCCAGGAC  CACCTCGTCC  TCGTGGCGGG  GCAGCAGGAG
11581  CGGTAGAAAG  GGGTCCGATG  TTTGAGGAGG  CCCTTAAGGG  AAGCTACTGA  ATTATAACAC
11641  GTAAGAAAAT  CACCATTCTT  CCGTATTGGT  TGGGGGCTCC  TGTTTCTCAT  CCTAGCTTTT
11701  TCCTGGAAAA  GCCCGCTAGA  AGTTTGGGA   ACGAGGGGAA  AGTTCTCAGA  ACTGTTGCTG
11761  CTCCCCACCC  GCCTCCCGCC  TCCCCCGCAG  GTTATGTCAG  CAGCTCTGAG  ACAGCAGTAT
11821  CACAGGCCAG  ATGTTGTTCC  TGGCTAGATG  TTTACATTTG  TAAGAAAATAA CACTGTGAAT
11881  GTAAAACAGA  GCCATTCCCT  TGGAATGCAT  ATCGCTGGGC  TCAACATAGA  GTTGTCTTC
11941  CTCTTGTTTA  CGACGTGATC  TAAACCAGTC  CTTAGCAAGG  GGCTCAGAAC  ACCCCGCTCT
12001  GGCAGTAGGT  GTCCCCCACC  CCCAAAGACC  TGCCTGTGTG  CTCCGGAGAT  GAATATGAGC
12061  TCATTAGTAA  AAATGACTTC  ACCCACGCAT  ATACATAAAG  TATCCATGCA  CTCTAAGAGT
12121  GACACATCTA  TAATTTTACA  CACACACCTC  TCAAGACGGA  GATGCATGGC  CCGCCAGGTC AAGTTAGCCG
12181  GCCCGTGTCG  GTTCTTCCTG  GAAGTTGACT  TTCCTTAGAC  CAGGGCAGGG  CTCATTCATT  GCCCACTAGG
12241  CGTGACGGAC  ATCCAGGCGT  GGGACGTGGT  GCTCTCTGCA  GCTCTCTGCA  GAAGGGAGGA AGACTTTATC
12301  ATCCCACTGG  CGAAGATGGT  CTCCATATCA  GCTCTCTGCA  TCGTATTATC  TGCAAATGTG
12361  ATGTTCCTAA  AAATCTGTGG  CAAGCACCCA  CAAATTTTGT  TGCAAATGTG
12421  ATTAATTTGG  TTGTCAAGTT  TTGGGGGTGG  GCTGTGGGGA  GATTGCTTTT  GTTTTCCTGC
12481  TGGTAATATC  GGGAAAGATT  TTAATGAAAC  CAGGGTAGAA  TTGTTTGGCA  ATGCACTGAA
12541  GCGTGTTTCT  TTCCCAAAAT  GTGCCTCCCT  TCCGCTGCGG  GCCCAGCTGA  GTCTATGTAG
```

```
12601  GTGATGTTTC  CAGCTGCCAA  GTGCTCTTTG  TTACTGTCCA  CCCTCATTTC  TGCCAGCGCA
12661  TGTGTCCTTT  CAAGGGGAAA  ATGTGAAGCT  GAACCCCCTC  CAGACACCCA  GAATGTAGCA
12721  TCTGAGAAGG  CCCTGTGCCC  TAAAGGACAC  CCCTCGCCCC  CATCTTCATG  GAGGGGGTCA
12781  TTTCAGAGCC  CTCGGAGCCA  ATGAACAGCT  CCTCCTCTTG  GAGCTGAGAT  GAGCCCCACG
12841  TGGAGCTCGG  GACGGATAGT  AGACAGCAAT  AACTCGGTGT  GTGGCCGCCT  GGCAGGTGGA
12901  ACTTCCTCCC  GTTGCGGGGT  GGAGTGAGGT  TAGTTCTGTG  TGTCTGGTGG  GTGGAGTCAG
12961  GCTTCTCTTG  CTACCTGTGA  GCATCCTTCC  CAGCAGACAT  CCTCATCGGG  CTTTGTCCCT
13021  CCCCGCTTC   CTCCCTCTGC  GGGGAGGACC  CGGGACCACA  GCTGCTGGCC  AGGGTAGACT
13081  TGGAGCTGTC  CTCCAGAGGG  GTCACGTGTA  GGAGTGAGAA  GAAGGAAGAT  CTTGAGAGCT
13141  GCTGAGGGAC  CTTGGAGAGC  TCAGGATGGC  TCAGACGAGG  ACACTCGCTT  GCCGGGCCTG
13201  GCCCTTCCTGG GAAGGAGGGA  GCTGCTCAGA  ATGCCGCATG  ACAACTGAAG  GCAACCTGGA
13261  AGGTTCAGGG  CCCGCTCTTC  CCCCATGTGC  CTGTCACGCT  CTGGTGCAGT  CAAAGGAACG
13321  CCTTCCCCTC  AGTTGTTTCT  AAGAGCAGAG  TCTCCCGCTG  CAATCTGGGT  GGTAACTGCC
13381  AGCCTTGGAG  GATCGTGGCC  AACGTGGACC  TGCCTACGGA  GGGTGGGCTC  TGACCCAAGT
13441  GGGGCCTCCT  TGCCCAGGTC  TCACTGCTTT  GCAGGGGACT  CAGAGGGACT  GTCAGCTGAG
13501  CTTGAGCTCC  CCTGGAGCCA  GCAGGGCTGT  GATGGGCGAG  TCCCGGAGCC  CCACCCAGAC
13561  CTGAATGCTT  CTGAGAGCAA  AGGGAAGGAC  TGACGAGAGA  TGTATATTTA  ATTTTTTAAC
13621  TGCTGCAAAC  ATTGTACATC  CAAATTAAAG  GGAAAAAAATG GAAACCATCA  AT
```

```
   1 matleklmka feslksfggq gqqqqqqqq qqqqqqqqq pppppppppp pqlpqpppqa
  61 qplpqpqpp pppppppppp avaeeeplhrp kkelsatkkd rvnhcltice nivagsvrns
 121 pefgkligia melflicedd aesdvrmvad ecInkvikal mdsnlprigl elykeikkng
 181 aprslraalw rfaelahlvr pqkcrpylvn llpcltrtsk rpeesvqetl aaavpkimas
 241 fgnfandnei kvllkafian lksssptirr taagsavsic qhsrrtqyfy swlinvllgl
 301 lvpvedehst llilgvlltl rylvpllgqq vkdtslkgsf gvtrkemevs psaeqlvqvy
 361 eitlhhtqhq dhnvvtgale llqqlfrtpp peliqtltav ggigqltaak eesggrsrsg
 421 siveliaggg sscspvlsrk qkgkvllgee ealeddsesr sdvsssalta svkdeisgel
 481 aassgvstpg saghdiiteq prsqhtlgad svdlascdlt ssatdgdeed ilshsssqvs
 541 avpsdpamdl ndgtgasspi sdssqttteg pdsavtpsds seivldgtdn qylglqiqgp
 601 qdedeeatgi lpdeaseafr nssmalgqah llknmshcrq psdssvdkfv lrdeatepgd
 661 qenkpcrikg diggstddds aplvhcvrli sasflitggk nvlvpdrdvr vsvkalalsc
 721 vgaavalhpe sffsklykvp ldtteypeeq yvsdilnyid hgdpqvrgat ailcgtlics
 781 ilsrsrfhvg dwmgtirtlt gntfsladci plirktlkde ssvtcklact avrncvmslc
 841 ssysellglq liidvltlrn ssywlvrtel letlaeidfr lvsfleakae nlhrgahhyt
 901 glikIqervl nnvvihligd edprvrhvaa aslirlvpkl fykcdggqad pvvavardgs
 961 svylkllmhe tqppshfsvs titrlyrgyn llpsitdvtm ennlsrviaa vshelitstt
1021 raltfgccea lcllstafpv ciwslgwhcg vpplsasdes rksctvgmat mlltlssaw
1081 fpldlsahgd alilagnlla asapkslrss waseeeanpa atkqeevwpa lgdralvpmv
1141 eqlfshllkv inicahvldd vapgpaikaa lpslnppsl spirrkgkek epgeqasvpl
1201 spkkgseasa asrqsdtsgp vttsksssIg sfyhlpsylk lhdvlkatha nykvtldlqn
1261 stekfggflr saldvlsqil elatlqdigk cveeilgylk scfsrepmma tvcvqqllkt
1321 lfgtnlasqf dglssnpsks ggraqrlgss svrpglyhyc fmapythftq aladaslrnm
1381 vgaeegendts gwfdvlqkvs tqlktnltsv tknradknai hnhirlfepl vikalkqytt
1441 ttcvqlgkqv ldllaglvql rvnyclldsd qvfigfvlkq feyievggfr eseaiipnif
1501 fffvllsyer yhskqiigip kiiqlcdgim asgrkavtha ipalqpivhd lfvIrgtnka
1561 dagkeletqk evvvsmlirl iqyhqvlemf ilvlqgchke nedkwkrlsr qiadiilpml
1621 akqqmhidsh ealgvIntlf eilapsslrp vdmllrsmfv tpntmasvst vqlwisgila
1681 ilrvlisqst edivlsrige lsfspylisc tvinrlrdgd ststleehse gkqiknlpee
```

```
1741 tfsrfiliqlv gilledivtk qlkvemseqq htfycqelgt llmclihifk sgmfrritaa
1801 atrlfrsdgc ggsfytldsl nlrarsmitt hpalvllwcq illlvnhtdy rwwaevqqtp
1861 krhslsstkl lspqmsgeee dsdlaaklgm cnreivrrga lilfcdyvcq nlhdsehltw
1921 livnhiqdli slsheppvqd fisavhrnsa asglfiqaiq srcenlstpt mlkktlqcle
1981 gihlsqsgav ltlyvdrllc tpfrvlarmv dilacrrvem llaanlqssm aqlpmeelnr
2041 iqeylqssgl aqrhqrlysl ldrfrlstmq dslspsppvs shpldgdghv sletvspdkd
2101 wyvhlvksgc wtrsdsalle gaelvnripa edmnafmmns efnlsllapc lslgmseisg
2161 gqksalfeaa revtlarvsg tvgqlpavhh vfqpelpaep aaywsklndl fgdaalygsl
2221 ptlaralagy lvvvsklpsh lhlppekekd ivkfvvatle alswhliheq iplsldlqag
2281 ldccclalql pglwsvvsst efvthacsli ycvhfileav avqpgeqlis perrtntpka
2341 iseeeeevdp ntqnpkyita acemvaemve slgsvlalgh krnsgvpafl tplirnliis
2401 larlplvnsy trvpplvwkl gwspkpggdf gtafpeipve flqekevfke flyrintlgw
2461 tsrtqfeetw atilgvlvtq plvmeqeesp peedtertgi nvlavqaits lvlsamtvpv
2521 agnpavscle gqprnkpika ldtrfgrkls iirgivegei qamvskreni athhlygawd
2581 pvpslspatt galishekll lqinperelg smsyklgqvs ihsvwlgnsi tplreeewde
2641 eeeeeadapa psspptspvn srkhragvdi hscsqfllel ysrwilpsss arrtpailis
2701 evvrslivvs difterngfe lmyvtltelr rvhpsedeil aqylvpatck aaavlgmdka
2761 vaepvsrlle stlrsshlps rvgalhgvly vlecdllddt akqlipvisd yllsnlkgia
2821 hcvnihsqgh vlvmcatafy lienypldvg pefsasliqm cgvmlsgsee stpsiiyhca
2881 lrglerllls eqlsrldaes lvklsvdrvn vhsphramaa lglmltcmyt gkekvspgrt
2941 sdpnpaapds esvivamerv svlfdrirkg fpcearvvar ilpqflddff ppqdimnkvi
3001 geflsnqqpy pqfmatvvyk vfqtlhstgq ssmvrdwvml slsnftgrap vamatwslsc
3061 ffvsastspw vaailphvis rmgkleqvdv nlfclvatdf yrhqieeeld rrafqsvlev
3121 vaapgspyhr lltclrnvhk vttc
```

FIG. 3 htt sense target:      5´-...ugcagcugaucaucgaugugcugacccugaggaacaguuc...-3´
htt anti-sense target: 3´-...acgucgacuaguagcuacacgacugggacuccuugucaag...-5´

SEQ ID NO:20    5′-UGUGC
                •••••
SEQ ID NO:21   3′-CUACACG        ΔG = -10.5

SEQ ID NO:22    5′-GUUGC
                •••••
SEQ ID NO:23   3′-GAGAAGG        ΔG = -10.5

FIG. 4

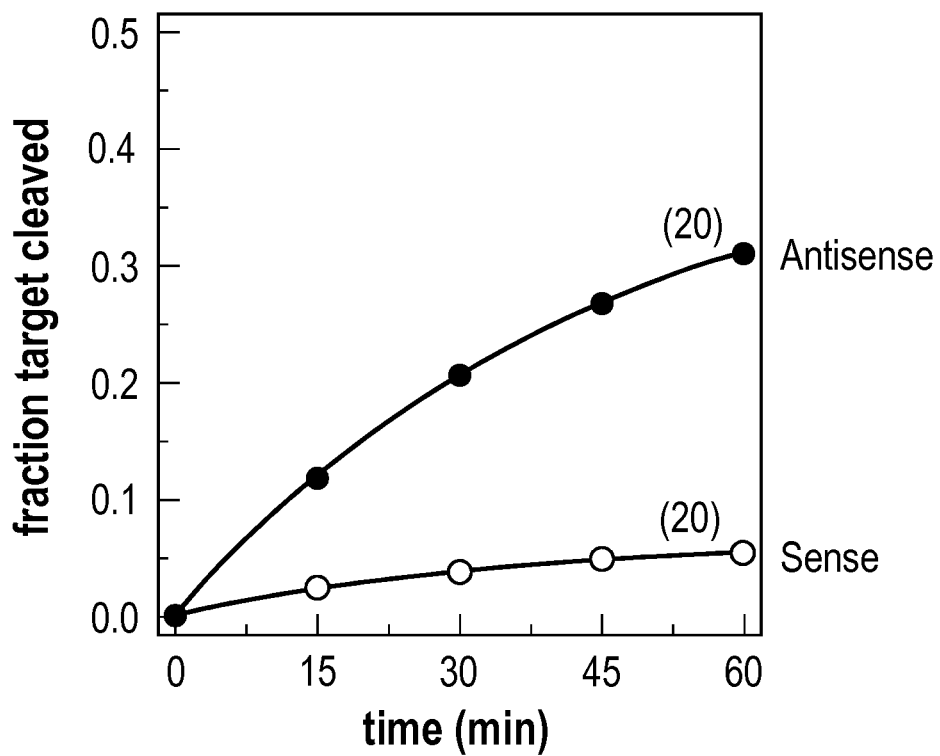
FIG. 5B

5'-UGUGCUGACCCUGAGGAAAAG-3'   SEQ ID NO:28
3'-CUACACGACUGGGACUCCUUG-5'   SEQ ID NO:29
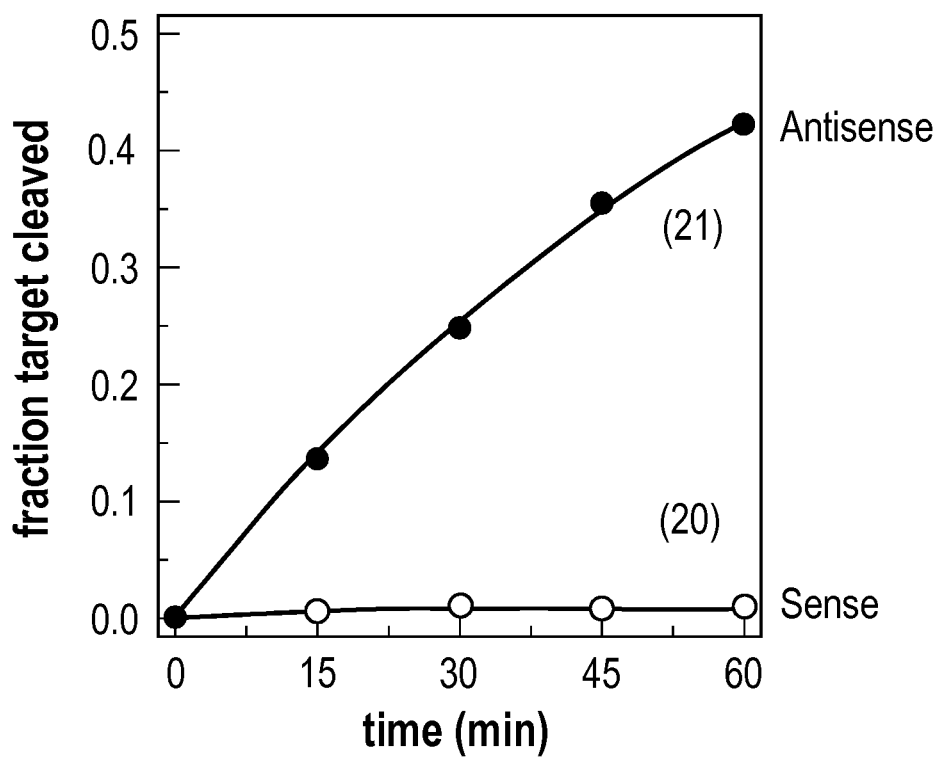
FIG. 5C

FIG. 7

| SNP site (refSNP) | Location | Allelic Frequency | SNP alleles (gene) | SNP alleles (mRNA) |
|---|---|---|---|---|
| RS362331 | Exon 50 | 42% | C/T | C/U |
| RS4690077 | Exon 48 | 34.9% | A/G | A/G |
| RS363125 | Exon 39 | 15.4% | A/C | A/C |
| 47bp into | Exon 25 | 11.2% | G/A | G/A |
| RS363075 | Exon 20 | 11.2% | G/A | G/A |
| RS362268 | 3'UTR | 33.9% | C/G | C/G |
| RS362267 | 3'UTR | 33.3% | C/T | C/U |
| RS362307 | 3'UTR | 32.8% | C/T | C/U |
| RS362306 | 3'UTR | 33.3% | A/G | A/G |
| RS362305 | 3'UTR | 16.4% | C/T | C/U |
| RS362304 | 3'UTR | 17.9% | C/A | C/A |
| RS362303 | 3'UTR | 15.8% | C/T | C/U |

FIG. 8
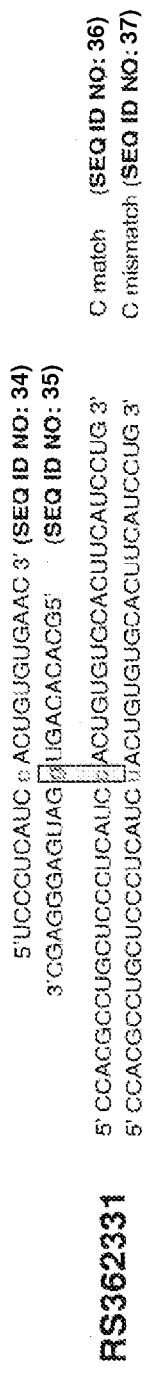
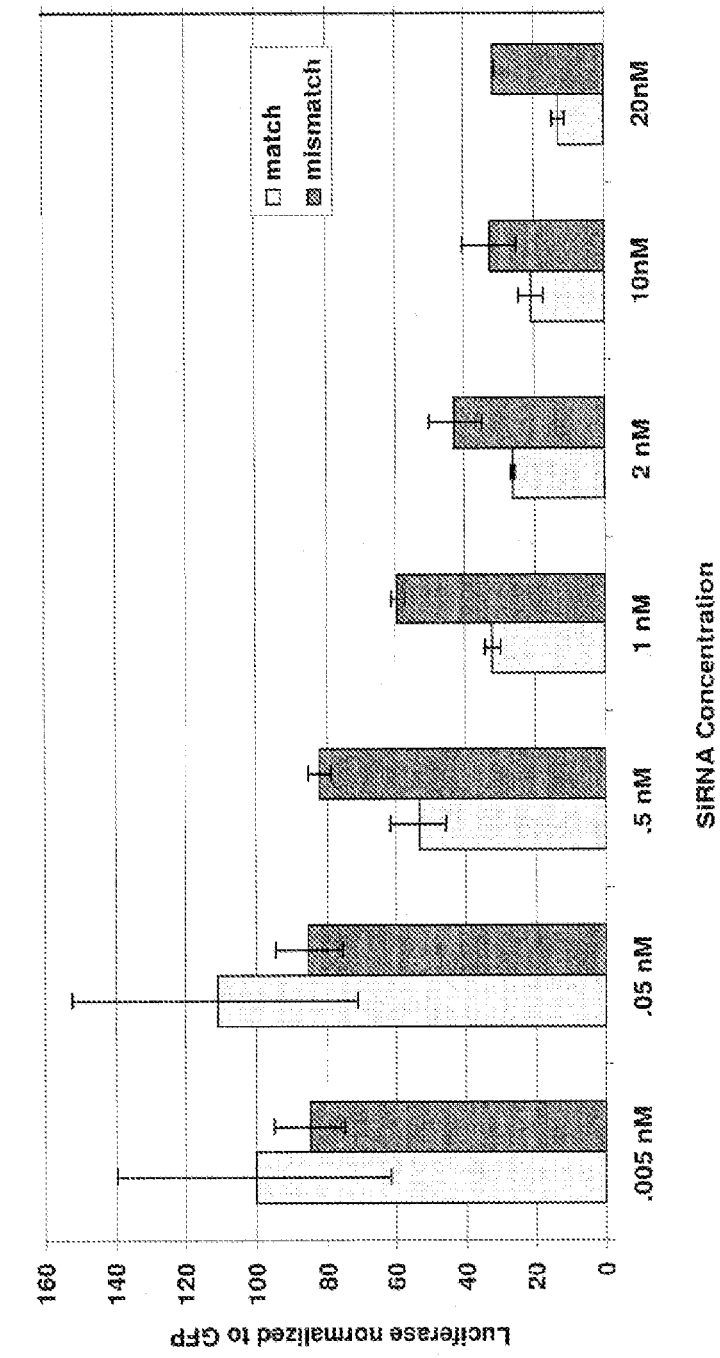

FIG. 10
A.
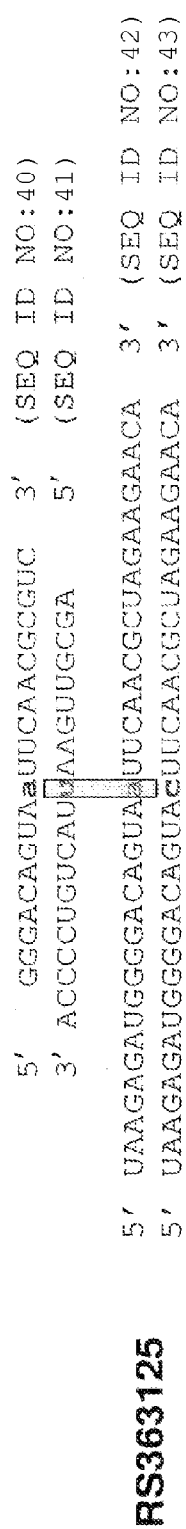
RS363125
B.
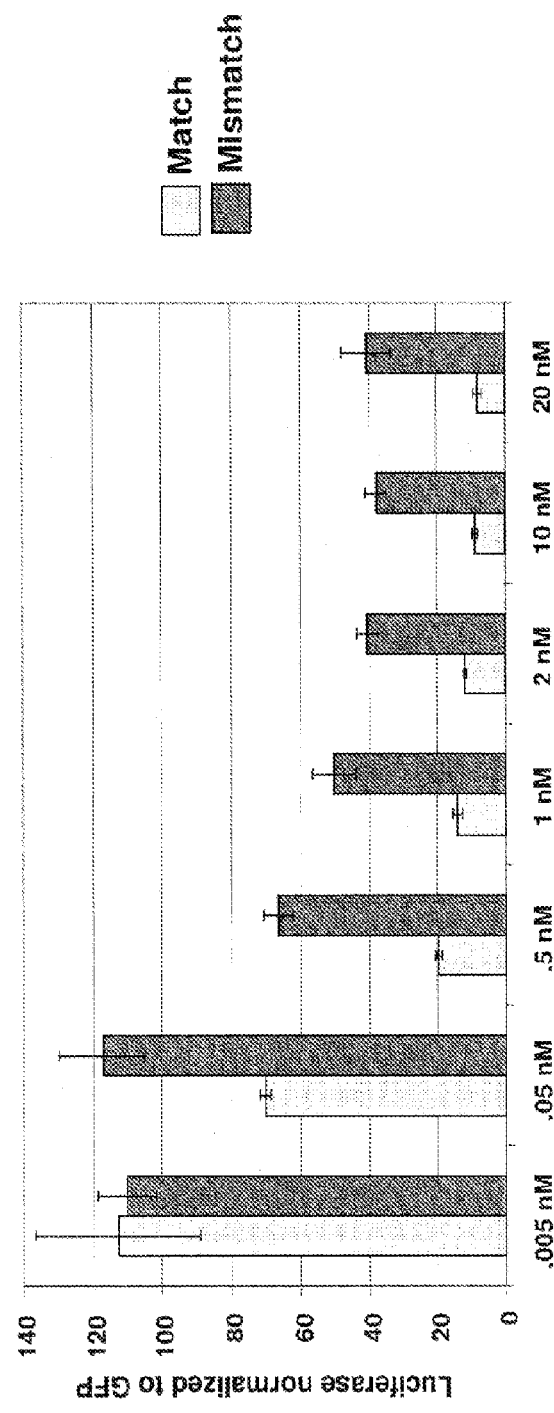

FIG. 11
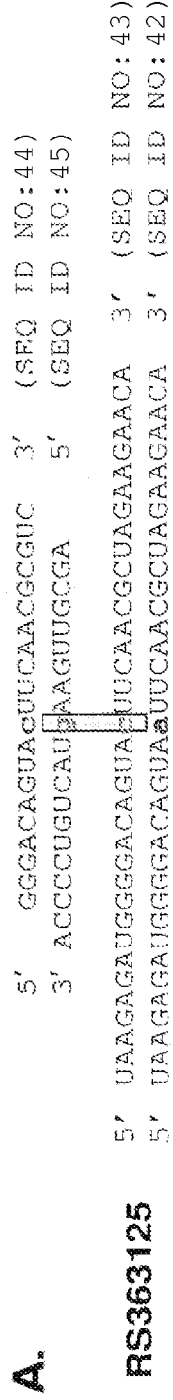
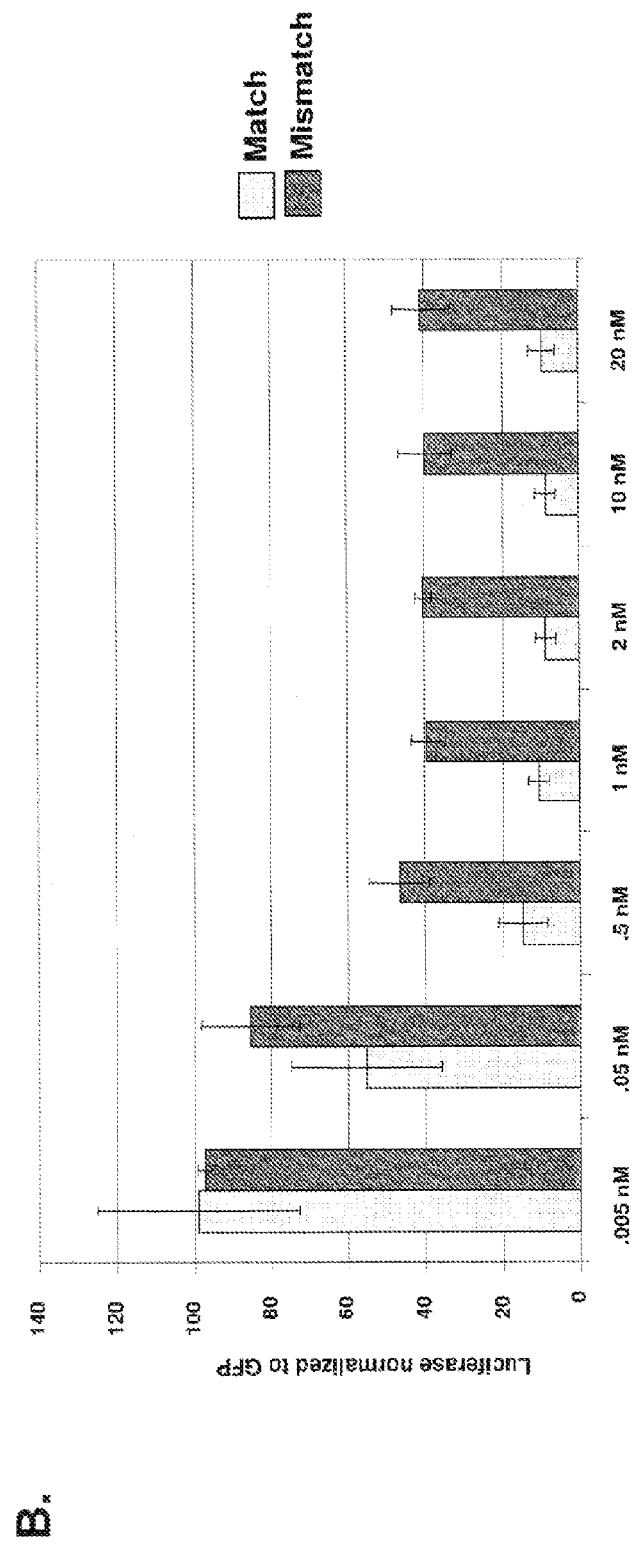

FIG. 12
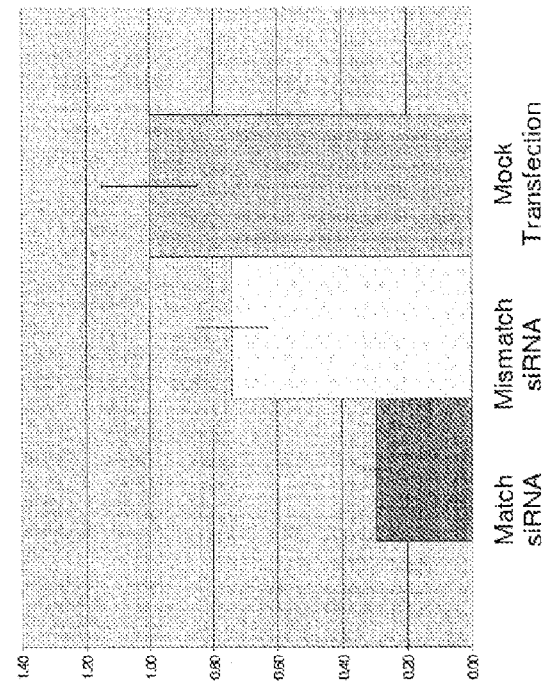
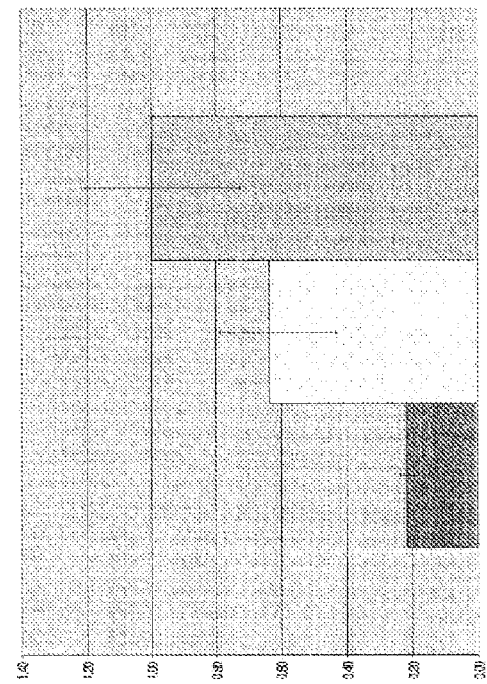

SEQUENCE LISTING

```
<160> NUMBER OF SEQ ID NOS: 50

<210> SEQ ID NO 1
<211> LENGTH: 13672
<212> TYPE: DNA
<213> ORGANISM: Homo sapiens

<400> SEQUENCE: 1
ttgctgtgtg aggcagaacc tgcgggggca ggggcgggct ggttccctgg ccagccattg      60
gcagagtccg caggctaggg ctgtcaatca tgctggccgg cgtggccccg cctccgccgg     120
```

| | |
|---|---|
| cgcggccccg cctccgccgg cgcacgtctg ggacgcaagg cgccgtgggg gctgccggga | 180 |
| cgggtccaag atggacggcc gctcaggttc tgcttttacc tgcggcccag agccccattc | 240 |
| attgccccgg tgctgagcgg cgccgcgagt cggcccgagg cctccgggga ctgccgtgcc | 300 |
| gggcgggaga ccgccatggc gaccctggaa aagctgatga aggccttcga gtccctcaag | 360 |
| tccttccagc agcagcagca gcagcagcag cagcagcagc agcagcagca gcagcagcag | 420 |
| cagcagcagc aacagccgcc accgccgccg ccgccgccgc cgcctcctca gcttcctcag | 480 |
| ccgccgccgc aggcacagcc gctgctgcct cagccgcagc cgcccccgcc gccgccccg | 540 |
| ccgccacccg gccggctgt ggctgaggag ccgctgcacc gaccaaagaa agaactttca | 600 |
| gctaccaaga aagaccgtgt gaatcattgt ctgacaatat gtgaaaacat agtggcacag | 660 |
| tctgtcagaa attctccaga atttcagaaa cttctgggca tcgctatgga acttttctg | 720 |
| ctgtgcagtg atgacgcaga gtcagatgtc aggatggtgg ctgacgaatg cctcaacaaa | 780 |
| gttatcaaag cttttgatgga ttctaatctt ccaaggttac agctcgagct ctataaggaa | 840 |
| attaaaaaga atggtgcccc tcggagtttg cgtgctgccc tgtggaggtt tgctgagctg | 900 |
| gctcacctgg ttcggcctca gaaatgcagg ccttacctgg tgaaccttct gccgtgcctg | 960 |
| actcgaacaa gcaagagacc cgaagaatca gtccaggaga ccttggctgc agctgttccc | 1020 |
| aaaattatgg cttcttttgg caattttgca aatgacaatg aaattaaggt tttgttaaag | 1080 |
| gccttcatag cgaacctgaa gtcaagctcc cccaccattc ggcggacagc ggctggatca | 1140 |
| gcagtgagca tctgccagca ctcaagaagg acacaatatt tctatagttg gctactaaat | 1200 |
| gtgctcttag gcttactcgt tcctgtcgag gatgaacact ccactctgct gattcttggc | 1260 |
| gtgctgctca ccctgaggta tttggtgccc ttgctgcagc agcaggtcaa ggacacaagc | 1320 |
| ctgaaaggca gcttcggagt gacaaggaaa gaaatgaag tctctccttc tgcagagcag | 1380 |
| cttgtccagg tttatgaact gacgttacat catacacagc accaagacca caatgttgtg | 1440 |
| accgagcccc tggagctgtt gcagcagctc ttcagaacgc ctccacccga gcttctgcaa | 1500 |
| accctgaccg cagtcggggg cattgggcag ctcaccgctg ctaaggagga gtctggtggc | 1560 |
| cgaagccgta gtgggagtat tgtggaactt atagctggag ggggttcctc atgcagccct | 1620 |
| gtcctttcaa gaaaacaaaa aggcaaagtg ctcttaggag aagaagaagc cttggaggat | 1680 |
| gactctgaat cgagatcgga tgtcagcagc tctgccttaa cagcctcagt gaaggatgag | 1740 |
| atcagtggag agctggctgc ttcttcaggg gtttccactc cagggtcagc aggtcatgac | 1800 |
| atcatcacag aacagccacg gtcacagcac acactgcagg cggactcagt ggatctggcc | 1860 |
| agctgtgact tgacaagctc tgccactgat ggggatgagg aggatatctt gagccacagc | 1920 |
| tccagccagg tcagcgccgt cccatctgac cctgccatgg acctgaatga tgggaccccag | 1980 |
| gcctcgtcgc ccatcagcga cagctcccag accaccaccg aagggcctga ttcagctgtt | 2040 |
| accccttcag acagttctga aattgtgtta gacggtaccg acaaccagta tttgggcctg | 2100 |
| cagattggac agccccagga tgaagatgag gaagccacag gtattcttcc tgatgaagcc | 2160 |
| tcggaggcct tcaggaactc ttccatggcc cttcaacagg cacatttatt gaaaaacatg | 2220 |
| agtcactgca ggcagccttc tgacagcagt gttgataaat ttgtgttgag agatgaagct | 2280 |
| actgaaccgg gtgatcaaga aaacaagcct tgccgcatca aggtgacat ggacagtcc | 2340 |
| actgatgatg actctgcacc tcttgtccat tgtgtccgcc ttttatctgc ttcgttttg | 2400 |
| ctaacagggg gaaaaaatgt gctggttccg gacagggatg tgagggtcag cgtgaaggcc | 2460 |
| ctggccctca gctgtgtggg agcagctgtg gccctccacc cggaatcttt cttcagcaaa | 2520 |

```
ctctataaag ttcctcttga caccacggaa taccctgagg aacagtatgt ctcagacatc    2580
ttgaactaca tcgatcatgg agacccacag gttcgaggag ccactgccat tctctgtggg    2640
accctcatct gctccatcct cagcaggtcc cgcttccacg tgggagattg gatgggcacc    2700
attagaaccc tcacaggaaa tacattttct ttggcggatt gcattccttt gctgcggaaa    2760
acactgaagg atgagtcttc tgttacttgc aagttagctt gtacagctgt gaggaactgt    2820
gtcatgagtc tctgcagcag cagctacagt gagttaggac tgcagctgat catcgatgtg    2880
ctgactctga ggaacagttc ctattggctg gtgaggacag agcttctgga aacccttgca    2940
gagattgact tcaggctggt gagcttttg gaggcaaaag cagaaaactt acacagaggg    3000
gctcatcatt atacagggct tttaaaactg caagaacgag tgctcaataa tgttgtcatc    3060
catttgcttg gagatgaaga ccccagggtg cgacatgttg ccgcagcatc actaattagg    3120
cttgtcccaa agctgtttta taatgtgac caaggacaag ctgatccagt agtggccgtg    3180
gcaagagatc aaagcagtgt ttacctgaaa cttctcatgc atgagacgca gcctccatct    3240
catttctccg tcagcacaat aaccagaata tatagaggct ataacctact accaagcata    3300
acagacgtca ctatggaaaa taaccttcca agagttattg cagcagtttc tcatgaacta    3360
atcacatcaa ccaccagagc actcacattt ggatgctgtg aagctttgtg tcttctttcc    3420
actgccttcc cagtttgcat ttggagttta ggttggcact gtggagtgcc tccactgagt    3480
gcctcagatg agtctaggaa gagctgtacc gttgggatgg ccacaatgat tctgaccctg    3540
ctctcgtcag cttggttccc attggatctc tcagcccatc aagatgcttt gattttggcc    3600
ggaaacttgc ttgcagccag tgctcccaaa tctctgagaa gttcatgggc ctctgaagaa    3660
gaagccaacc cagcagccac caagcaagag gaggtctggc cagccctggg ggaccgggcc    3720
ctggtgccca tggtggagca gctcttctct cacctgctga aggtgattaa catttgtgcc    3780
cacgtcctgg atgacgtggc tcctggaccc gcaataaagg cagccttgcc ttctctaaca    3840 aaccccccctt ctctaagtcc catccgacga aaggggaagg agaaagaacc aggagaacaa    3900
gcatctgtac cgttgagtcc caagaaaggc agtgaggcca gtgcagcttc tagacaatct    3960
gatacctcag gtcctgttac aacaagtaaa tcctcatcac tggggagttt ctatcatctt    4020
ccttcatacc tcaaactgca tgatgtcctg aaagctacac acgctaacta caaggtcacg    4080
ctggatcttc agaacagcac ggaaaagttt ggagggtttc tccgctcagc cttgatgtt    4140 cttctctcaga tactagagct ggccacactg caggacattg ggaagtgtgt tgaagagatc    4200
ctaggatacc tgaaatcctg ctttagtcga gaaccaatga tggcaactgt ttgtgttcaa    4260
caattgttga agactctctt tggcacaaac ttggcctccc agtttgatgg cttatcttcc    4320
aaccccagca gtcacaaagg ccgagcacag cgccttggct cctccagtgt gaggccaggc    4380
ttgtaccact actgcttcat ggccccgtac acccacttca cccaggccct cgctgacgcc    4440
agcctgagga acatggtgca ggcggagcag gagaacgaca cctcgggatg gtttgatgtc    4500
ctccagaaag tgtctaccca gttgaagaca aacctcacga gtgtcacaaa gaaccgtgca    4560
gataagaatg ctattcataa tcacattcgt ttgtttgaac ctcttgttat aaaagcttta    4620
aaacagtaca cgactacaac atgtgtgcag ttacagaagc aggttttaga tttgctggcg    4680
cagctggttc agttacgggt taattactgt cttctggatt cagatcaggt gtttattggc    4740
tttgtattga acagtttga atacattgaa gtgggccagt tcaggaatc agaggcaatc    4800 attccaaaca tctttttctt cttggtatta ctatcttatg aacgctatca ttcaaaacag    4860
atcattggaa ttcctaaaat cattcagctc tgtgatggca tcatggccag tggaaggaag    4920
```

```
gctgtgacac atgccatacc ggctctgcag cccatagtcc acgacctctt tgtattaaga    4980
ggaacaaata aagctgatgc aggaaaagag cttgaaaccc aaaaagaggt ggtggtgtca    5040
atgttactga gactcatcca gtaccatcag gtgttggaga tgttcattct tgtcctgcag    5100
cagtgccaca aggagaatga agacaagtgg aagcgactgt ctcgacagat agctgacatc    5160
atcctcccaa tgttagccaa acagcagatg cacattgact ctcatgaagc ccttggagtg    5220
ttaaatacat tatttgagat tttggcccct tcctccctcc gtccggtaga catgcttta     5280
cggagtatgt tcgtcactcc aaacacaatg gcgtccgtga gcactgttca actgtggata    5340
tcggaattc tggccatttt gagggttctg atttcccagt caactgaaga tattgttctt     5400
tctcgtattc aggagctctc cttctctccg tatttaatct cctgtacagt aattaatagg    5460
ttaagagatg gggacagtac ttcaacgcta agaacacaca gtgaagggaa acaaataaag    5520
aatttgccag aagaaacatt ttcaaggttt ctattacaac tggttggtat tcttttagaa    5580
gacattgtta caaaacagct gaaggtggaa atgagtgagc agcaacatac tttctattgc    5640
caggaactag gcacactgct aatgtgtctg atccacatct tcaagtctgg aatgttccgg    5700
agaatcacag cagctgccac taggctgttc cgcagtgatg gctgtggcgg cagtttctac    5760
accctggaca gcttgaactt gcgggctcgt tccatgatca ccacccaccc ggccctggtg    5820
ctgctctggt gtcagatact gctgcttgtc aaccacaccg actaccgctg gtgggcagaa    5880
gtgcagcaga ccccgaaaag acacagtctg tccagcacaa agttacttag tccccagatg    5940
tctggagaag aggaggattc tgacttggca gccaaacttg gaatgtgcaa tagagaaata    6000
gtacgaagag gggctctcat tctcttctgt gattatgtct gtcagaacct ccatgactcc    6060
gagcacttaa cgtggctcat tgtaaataac attcaagatc tgatcagcct ttcccacgag    6120
cctccagtac aggacttcat cagtgccgtt catcggaact ctgctgccag cggcctgttc    6180
atccaggcaa ttcagtctcg ttgtgaaaac ctttcaactc caaccatgct gaagaaaact    6240
cttcagtgct tggaggggat ccatctcagc cagtcgggag ctgtgctcac gctgtatgtg    6300
gacaggcttc tgtgcacccc tttccgtgtg ctggctcgca tggtcgacat ccttgcttgt    6360
cgccgggtag aaatgcttct ggctgcaaat ttacagagca gcatggccca gttgccaatg    6420
gaagaactca acagaatcca ggaatacctt cagagcagcg ggctcgctca gagacaccaa    6480
aggctctatt ccctgctgga caggtttcgt ctctccacca tgcaagactc acttagtccc    6540
tctcctccag tctcttccca cccgctggac ggggatgggc acgtgtcact ggaaacagtg    6600
agtccggaca aagactggta cgttcatctt gtcaaatccc agtgttggac caggtcgat    6660
tctgcactgc tggaaggtgc agagctggtg aatcggattc ctgctgaaga tatgaatgcc    6720
ttcatgatga actcggagtt caacctaagc ctgctagctc catgcttaag cctagggatg    6780
agtgaaattt ctggtggcca aagagtgcc ctttttgaag cagcccgtga ggtgactctg     6840
gcccgtgtga gcggcaccgt gcagcagctc cctgctgtcc atcatgtctt ccagcccgag    6900
ctgcctgcag agccggcggc ctactggagc aagttgaatg atctgtttgg ggatgctgca    6960
ctgtatcagt ccctgcccac tctggcccgg gccctggcac agtacctggt ggtggtctcc    7020
aaactgccca gtcatttgca ccttcctcct gagaaagaga aggacattgt gaaattcgtg    7080
gtggcaaccc ttgaggccct gtcctggcat ttgatccatg agcagatccc gctgagtctg    7140
gatctccagg cagggctgga ctgctgctgc ctggccctgc agctgcctgg cctctggagc    7200
gtggtctcct ccacagagtt tgtgacccac gcctgctccc tcatctactg tgtgcacttc    7260
atcctggagg ccgttgcagt gcagcctgga gagcagcttc ttagtccaga aagaaggaca    7320
```

| | |
|---|---|
| aatacccaa aagccatcag cgaggaggag gaggaagtag atccaaacac acagaatcct | 7380 |
| aagtatatca ctgcagcctg tgagatggtg gcagaaatgg tggagtctct gcagtcggtg | 7440 |
| ttggccttgg gtcataaaag gaatagcggc gtgccggcgt ttctcacgcc attgctcagg | 7500 |
| aacatcatca tcagcctggc ccgcctgccc cttgtcaaca gctacacacg tgtgccccca | 7560 |
| ctggtgtgga agcttggatg gtcacccaaa ccgggagggg attttggcac agcattccct | 7620 |
| gagatccccg tggagttcct ccaggaaaag gaagtcttta aggagttcat ctaccgcatc | 7680 |
| aacacactag gctggaccag tcgtactcag tttgaagaaa cttgggccac cctccttggt | 7740 |
| gtcctggtga cgcagcccct cgtgatggag caggaggaga gcccaccaga agaagacaca | 7800 |
| gagaggaccc agatcaacgt cctggccgtg caggccatca cctcactggt gctcagtgca | 7860 |
| atgactgtgc ctgtggccgg caacccagct gtaagctgct ggagcagca gccccggaac | 7920 |
| aagcctctga aagctctcga caccaggttt gggaggaagc tgagcattat cagagggatt | 7980 |
| gtggagcaag agattcaagc aatggtttca aagagagaga atattgccac ccatcattta | 8040 |
| tatcaggcat gggatcctgt cccttctctg tctccggcta ctacaggtgc cctcatcagc | 8100 |
| cacgagaagc tgctgctaca gatcaaccc gagcgggagc tggggagcat gagctacaaa | 8160 |
| ctcggccagg tgtccataca ctccgtgtgg ctggggaaca gcatcacacc cctgagggag | 8220 |
| gaggaatggg acgaggaaga ggaggaggag gccgacgccc ctgcaccttc gtcaccaccc | 8280 |
| acgtctccag tcaactccag gaaacaccgg gctggagttg acatccactc ctgttcgcag | 8340 |
| tttttgcttg agttgtacag ccgctggatc ctgccgtcca gctcagccag gaggacccg | 8400 |
| gccatcctga tcagtgaggt ggtcagatcc cttctagtgg tctcagactt gttcaccgag | 8460 |
| cgcaaccagt ttgagctgat gtatgtgacg ctgacagaac tgcgaagggt gcaccttca | 8520 |
| gaagacgaga tcctcgctca gtacctggtg cctgccacct gcaaggcagc tgccgtcctt | 8580 |
| gggatggaca aggccgtggc ggagcctgtc agccgcctgc tggagagcac gctcaggagc | 8640 |
| agccacctgc ccagcagggt tggagccctg cacggcgtcc tctatgtgct ggagtgcgac | 8700 |
| ctgctggacg acactgccaa gcagctcatc ccggtcatca gcgactatct cctctccaac | 8760 |
| ctgaaaggga tcgcccactg cgtgaacatt cacagccagc agcacgtact ggtcatgtgt | 8820 |
| gccactgcgt tttacctcat tgagaactat cctctggacg tagggccgga attttcagca | 8880 |
| tcaataatac agatgtgtgg ggtgatgctg tctggaagtg aggagtccac cccctccatc | 8940 |
| atttaccact gtgccctcag aggcctggag cgcctcctgc tctctgagca gctctcccgc | 9000 |
| ctggatgcag aatcgctggt caagctgagt gtggacagag tgaacgtgca cagcccgcac | 9060 |
| cgggccatgg cggctctggg cctgatgctc acctgcatgt acacaggaaa ggagaaagtc | 9120 |
| agtccgggta gaacttcaga ccctaatcct gcagccccg acagcgagtc agtgattgtt | 9180 |
| gctatggagc gggtatctgt tcttttgat aggatcagga aaggctttcc ttgtgaagcc | 9240 |
| agagtggtgg ccaggatcct gccccagttt ctagacgact tcttcccacc ccaggacatc | 9300 |
| atgaacaaag tcatcggaga gtttctgtcc aaccagcagc ataccccca gttcatggcc | 9360 |
| accgtggtgt ataaggtgtt tcagactctg cacagcaccg ggcagtcgtc catggtccgg | 9420 |
| gactgggtca tgctgtccct ctccaacttc acgcagaggg ccccgtcgc catggccacg | 9480 |
| tggagcctct cctgcttctt tgtcagcgcg tccaccagcc cgtgggtcgc ggcgatcctc | 9540 |
| ccacatgtca tcagcaggat gggcaagctg agcaggtgg acgtgaacct tttctgcctg | 9600 |
| gtcgccacag acttctacag acaccagata gaggaggagc tcgaccgcag ggccttccag | 9660 |
| tctgtgcttg aggtggttgc agccccagga agcccatatc accggctgct gacttgttta | 9720 |

```
cgaaatgtcc acaaggtcac cacctgctga gcgccatggt gggagagact gtgaggcggc   9780
agctggggcc ggagccttg gaagtctgtg cccttgtgcc ctgcctccac cgagccagct   9840
tggtccctat gggcttccgc acatgccgcg ggcggccagg caacgtgcgt gtctctgcca   9900
tgtggcagaa gtgctctttg tggcagtggc caggcaggga gtgtctgcag tcctggtggg   9960
gctgagcctg aggccttcca gaaagcagga gcagctgtgc tgcaccccat gtgggtgacc  10020
aggtcctttc tcctgatagt cacctgctgg ttgttgccag gttgcagctg ctcttgcatc  10080
tgggccagaa gtcctccctc ctgcaggctg gctgttggcc cctctgctgt cctgcagtag  10140
aaggtgccgt gagcaggctt tgggaacact ggcctgggtc tccctggtgg ggtgtgcatg  10200
ccacgccccg tgtctggatg cacagatgcc atggcctgtg ctgggccagt ggctggggt   10260 gctagacacc cggcaccatt ctcccttctc tcttttcttc tcaggattta aaatttaatt  10320
atatcagtaa agagattaat tttaacgaac tctttctatg cccgtgtaaa gtatgtgaat  10380
cgcaaggcct gtgctgcatg cgacagcgtc cggggtggtg gacagggccc ccggccacgc  10440
tccctctcct gtagccactg gcatagccct cctgagcacc cgctgacatt tccgttgtac  10500
atgttcctgt ttatgcattc acaaggtgac tgggatgtag agaggcgtta gtgggcaggt  10560
ggccacagca ggactgagga caggccccca ttatcctagg ggtgcgctca actgcagccc  10620
ctcctcctcg ggcacagacg actgtcgttc tccacccacc agtcagggac agcagcctcc  10680
ctgtcactca gctgagaagg ccagccctcc ctggctgtga gcagcctcca ctgtgtccag  10740
agacatgggc ctcccactcc tgttccttgc tagccctggg gtggcgtctg cctaggagct  10800
ggctggcagg tgttgggacc tgctgctcca tggatgcatg ccctaagagt gtcactgagc  10860
tgtgttttgt ctgagcctct ctcggtcaac agcaaagctt ggtgtcttgg cactgttagt  10920
gacagagccc agcatccctt ctgccccgt tccagctgac atcttgcacg gtgaccccctt  10980 ttagtcagga gagtgcagat ctgtgctcat cggagactgc cccacggccc tgtcagagcc  11040
gccactccta tccccaggac aggtccctgg accagcctcc tgtttgcagg cccagaggag  11100
ccaagtcatt aaaatggaag tggattctgg atggccgggc tgctgctgat gtaggagctg  11160
gatttgggag ctctgcttgc cgactggctg tgagacgagg caggggctct gcttcctcag  11220
ccctagaggc gagccaggca aggttggcga ctgtcatgtg gcttggtttg gtcatgcccg  11280
tcgatgtttt gggtattgaa tgtggtaagt ggaggaaatg ttggaactct gtgcaggtgc  11340
tgccttgaga ccccccaagct tccacctgtc cctctcctat gtggcagctg gggagcagct  11400
gagatgtgga cttgtatgct gcccacatac gtgagggga gctgaaaggg agccctgct   11460 caaagggagc cctcctctg agcagcctct gccaggcctg tatgaggctt ttcccaccag  11520
ctcccaacag aggcctcccc cagccaggac cacctcgtcc tcgtggcggg gcagcaggag  11580
cggtagaaag gggtccgatg tttgaggagg cccttaaggg aagctactga attataacac  11640
gtaagaaaat caccattctt ccgtattggt tgggggctcc tgtttctcat cctagctttt  11700
tcctggaaaa gcccgctaga aggtttggga acgagggaa agttctcaga actgttgctg   11760
ctccccaccc gcctcccgcc tccccgcag gttatgtcag cagctctgag acagcagtat  11820
cacaggccaa atgttgttcc tggctagatg tttacatttg taagaaataa cactgtgaat  11880
gtaaaacaga gccattccct tggaatgcat atcgctgggc tcaacataga gtttgtcttc  11940
ctcttgttta cgacgtgatc taaaccagtc cttagcaagg ggctcagaac accccgctct  12000
ggcagtaggt gtccccacc cccaaagacc tgcctgtgtg ctccggagat gaatatgagc  12060
tcattagtaa aaatgacttc acccacgcat atacataaag tatccatgca tgtgcatata  12120
```

-continued

```
gacacatcta taattttaca cacacacctc tcaagacgga gatgcatggc ctctaagagt    12180
gcccgtgtcg gttcttcctg gaagttgact ttccttagac ccgccaggtc aagttagccg    12240
cgtgacggac atccaggcgt gggacgtggt cagggcaggg ctcattcatt gcccactagg    12300
atcccactgg cgaagatggt ctccatatca gctctctgca aagggagga agactttatc    12360
atgttcctaa aaatctgtgg caagcaccca tcgtattatc caaattttgt tgcaaatgtg    12420
attaatttgg ttgtcaagtt ttgggggtgg gctgtgggga gattgctttt gttttcctgc    12480
tggtaatatc gggaaagatt ttaatgaaac cagggtagaa ttgtttggca atgcactgaa    12540
gcgtgtttct ttcccaaaat gtgcctccct tccgctgcgg gcccagctga gtctatgtag    12600
gtgatgtttc cagctgccaa gtgctctttg ttactgtcca ccctcatttc tgccagcgca    12660
tgtgtccttt caaggggaaa atgtgaagct gaaccccctc cagacaccca gaatgtagca    12720
tctgagaagg ccctgtgccc taaggacac ccctcgcccc catcttcatg gagggggtca    12780
tttcagagcc ctcggagcca atgaacagct cctcctcttg gagctgagat gagccccacg    12840
tggagctcgg gacggatagt agacagcaat aactcggtgt gtggccgcct ggcaggtgga    12900
acttcctccc gttgcggggt ggagtgaggt tagttctgtg tgtctggtgg gtggagtcag    12960
gcttctcttg ctacctgtga gcatccttcc cagcagacat cctcatcggg ctttgtccct    13020
cccccgcttc ctccctctgc ggggaggacc cgggaccaca gctgctggcc agggtagact    13080
tggagctgtc ctccagaggg gtcacgtgta ggagtgagaa gaaggaagat cttgagagct    13140
gctgagggac cttggagagc tcaggatggc tcagacgagg acactcgctt gccgggcctg    13200
gccctcctgg gaaggaggga gctgctcaga atgccgcatg acaactgaag gcaacctgga    13260
aggttcaggg cccgctcttc ccccatgtgc ctgtcacgct ctggtgcagt caaaggaacg    13320
ccttcccctc agttgtttct aagagcagag tctcccgctg caatctgggt ggtaactgcc    13380
agccttggag gatcgtggcc aacgtggacc tgcctacgga gggtgggctc tgacccaagt    13440
ggggcctcct tgcccaggtc tcactgcttt gcaccgtggt cagagggact gtcagctgag    13500
cttgagctcc cctggagcca gcagggctgt gatgggcgag tcccggagcc ccacccagac    13560
ctgaatgctt ctgagagcaa agggaaggac tgacgagaga tgtatattta atttttaac    13620
tgctgcaaac attgtacatc caaattaaag ggaaaaaatg gaaaccatca at            13672
```

<210> SEQ ID NO 2
<211> LENGTH: 3144
<212> TYPE: PRT
<213> ORGANISM: Homo sapiens

<400> SEQUENCE: 2

```
Met Ala Thr Leu Glu Lys Leu Met Lys Ala Phe Glu Ser Leu Lys Ser
  1               5                  10                  15

Phe Gln Gln Gln Gln Gln Gln Gln Gln Gln Gln Gln Gln Gln Gln Gln
                 20                  25                  30

Gln Gln Gln Gln Gln Gln Gln Gln Pro Pro Pro Pro Pro Pro Pro Pro
             35                  40                  45

Pro Pro Pro Gln Leu Pro Gln Pro Pro Gln Ala Gln Pro Leu Leu
         50                  55                  60

Pro Gln Pro Gln Pro Pro Pro Pro Pro Pro Pro Pro Gly Pro
 65                  70                  75                  80

Ala Val Ala Glu Glu Pro Leu His Arg Pro Lys Lys Glu Leu Ser Ala
                 85                  90                  95
```

-continued

```
Thr Lys Lys Asp Arg Val Asn His Cys Leu Thr Ile Cys Glu Asn Ile
            100                 105                 110
Val Ala Gln Ser Val Arg Asn Ser Pro Glu Phe Gln Lys Leu Leu Gly
        115                 120                 125
Ile Ala Met Glu Leu Phe Leu Leu Cys Ser Asp Asp Ala Glu Ser Asp
    130                 135                 140
Val Arg Met Val Ala Asp Glu Cys Leu Asn Lys Val Ile Lys Ala Leu
145                 150                 155                 160
Met Asp Ser Asn Leu Pro Arg Leu Gln Leu Glu Leu Tyr Lys Glu Ile
                165                 170                 175
Lys Lys Asn Gly Ala Pro Arg Ser Leu Arg Ala Ala Leu Trp Arg Phe
            180                 185                 190
Ala Glu Leu Ala His Leu Val Arg Pro Gln Lys Cys Arg Pro Tyr Leu
        195                 200                 205
Val Asn Leu Leu Pro Cys Leu Thr Arg Thr Ser Lys Arg Pro Glu Glu
    210                 215                 220
Ser Val Gln Glu Thr Leu Ala Ala Ala Val Pro Lys Ile Met Ala Ser
225                 230                 235                 240
Phe Gly Asn Phe Ala Asn Asp Asn Glu Ile Lys Val Leu Leu Lys Ala
                245                 250                 255
Phe Ile Ala Asn Leu Lys Ser Ser Ser Pro Thr Ile Arg Arg Thr Ala
            260                 265                 270
Ala Gly Ser Ala Val Ser Ile Cys Gln His Ser Arg Arg Thr Gln Tyr
        275                 280                 285
Phe Tyr Ser Trp Leu Leu Asn Val Leu Leu Gly Leu Leu Val Pro Val
    290                 295                 300
Glu Asp Glu His Ser Thr Leu Leu Ile Leu Gly Val Leu Leu Thr Leu
305                 310                 315                 320
Arg Tyr Leu Val Pro Leu Leu Gln Gln Gln Val Lys Asp Thr Ser Leu
                325                 330                 335
Lys Gly Ser Phe Gly Val Thr Arg Lys Glu Met Glu Val Ser Pro Ser
            340                 345                 350
Ala Glu Gln Leu Val Gln Val Tyr Glu Leu Thr Leu His His Thr Gln
        355                 360                 365
His Gln Asp His Asn Val Val Thr Gly Ala Leu Glu Leu Leu Gln Gln
    370                 375                 380
Leu Phe Arg Thr Pro Pro Pro Glu Leu Leu Gln Thr Leu Thr Ala Val
385                 390                 395                 400
Gly Gly Ile Gly Gln Leu Thr Ala Ala Lys Glu Glu Ser Gly Gly Arg
                405                 410                 415
Ser Arg Ser Gly Ser Ile Val Glu Leu Ile Ala Gly Gly Gly Ser Ser
            420                 425                 430
Cys Ser Pro Val Leu Ser Arg Lys Gln Lys Gly Lys Val Leu Leu Gly
        435                 440                 445
Glu Glu Glu Ala Leu Glu Asp Asp Ser Glu Ser Arg Ser Asp Val Ser
    450                 455                 460
Ser Ser Ala Leu Thr Ala Ser Val Lys Asp Glu Ile Ser Gly Glu Leu
465                 470                 475                 480
Ala Ala Ser Ser Gly Val Ser Thr Pro Gly Ser Ala Gly His Asp Ile
                485                 490                 495
Ile Thr Glu Gln Pro Arg Ser Gln His Thr Leu Gln Ala Asp Ser Val
            500                 505                 510
```

-continued

```
Asp Leu Ala Ser Cys Asp Leu Thr Ser Ser Ala Thr Asp Gly Asp Glu
            515                 520                 525

Glu Asp Ile Leu Ser His Ser Ser Ser Gln Val Ser Ala Val Pro Ser
        530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Ala Thr
        595                 600                 605

Gly Ile Leu Pro Asp Glu Ala Ser Glu Ala Phe Arg Asn Ser Ser Met
            610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Ser Ala Pro Leu Val His Cys Val Arg
        675                 680                 685

Leu Leu Ser Ala Ser Phe Leu Leu Thr Gly Gly Lys Asn Val Leu Val
            690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
        755                 760                 765

Ala Thr Ala Ile Leu Cys Gly Thr Leu Ile Cys Ser Ile Leu Ser Arg
            770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
            850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925
```

-continued

Ala Ala Ala Ser Leu Ile Arg Leu Val Pro Lys Leu Phe Tyr Lys Cys
930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
                980                 985                 990

Pro Ser Ile Thr Asp Val Thr Met Glu Asn Asn Leu Ser Arg Val Ile
                995                 1000                1005

Ala Ala Val Ser His Glu Leu Ile Thr Ser Thr Arg Ala Leu Thr
1010                1015                1020

Phe Gly Cys Cys Glu Ala Leu Cys Leu Leu Ser Thr Ala Phe Pro Val
1025                1030                1035                1040

Cys Ile Trp Ser Leu Gly Trp His Cys Gly Val Pro Leu Ser Ala
                1045                1050                1055

Ser Asp Glu Ser Arg Lys Ser Cys Thr Val Gly Met Ala Thr Met Ile
                1060                1065                1070

Leu Thr Leu Leu Ser Ser Ala Trp Phe Pro Leu Asp Leu Ser Ala His
                1075                1080                1085

Gln Asp Ala Leu Ile Leu Ala Gly Asn Leu Leu Ala Ala Ser Ala Pro
1090                1095                1100

Lys Ser Leu Arg Ser Ser Trp Ala Ser Glu Glu Ala Asn Pro Ala
1105                1110                1115                1120

Ala Thr Lys Gln Glu Glu Val Trp Pro Ala Leu Gly Asp Arg Ala Leu
                1125                1130                1135

Val Pro Met Val Glu Gln Leu Phe Ser His Leu Leu Lys Val Ile Asn
                1140                1145                1150

Ile Cys Ala His Val Leu Asp Asp Val Ala Pro Gly Pro Ala Ile Lys
                1155                1160                1165

Ala Ala Leu Pro Ser Leu Thr Asn Pro Pro Ser Leu Ser Pro Ile Arg
1170                1175                1180

Arg Lys Gly Lys Glu Lys Glu Pro Gly Glu Gln Ala Ser Val Pro Leu
1185                1190                1195                1200

Ser Pro Lys Lys Gly Ser Glu Ala Ser Ala Ala Ser Arg Gln Ser Asp
                1205                1210                1215

Thr Ser Gly Pro Val Thr Thr Ser Lys Ser Ser Ser Leu Gly Ser Phe
                1220                1225                1230

Tyr His Leu Pro Ser Tyr Leu Lys Leu His Asp Val Leu Lys Ala Thr
                1235                1240                1245

His Ala Asn Tyr Lys Val Thr Leu Asp Leu Gln Asn Ser Thr Glu Lys
                1250                1255                1260

Phe Gly Gly Phe Leu Arg Ser Ala Leu Asp Val Leu Ser Gln Ile Leu
1265                1270                1275                1280

Glu Leu Ala Thr Leu Gln Asp Ile Gly Lys Cys Val Glu Glu Ile Leu
                1285                1290                1295

Gly Tyr Leu Lys Ser Cys Phe Ser Arg Glu Pro Met Met Ala Thr Val
                1300                1305                1310

Cys Val Gln Gln Leu Leu Lys Thr Leu Phe Gly Thr Asn Leu Ala Ser
                1315                1320                1325

Gln Phe Asp Gly Leu Ser Ser Asn Pro Ser Lys Ser Gln Gly Arg Ala
                1330                1335                1340

-continued

Gln Arg Leu Gly Ser Ser Val Arg Pro Gly Leu Tyr His Tyr Cys
1345                1350                1355                1360

Phe Met Ala Pro Tyr Thr His Phe Thr Gln Ala Leu Ala Asp Ala Ser
            1365                1370                1375

Leu Arg Asn Met Val Gln Ala Glu Gln Glu Asn Asp Thr Ser Gly Trp
        1380                1385                1390

Phe Asp Val Leu Gln Lys Val Ser Thr Gln Leu Lys Thr Asn Leu Thr
    1395                1400                1405

Ser Val Thr Lys Asn Arg Ala Asp Lys Asn Ala Ile His Asn His Ile
1410                1415                1420

Arg Leu Phe Glu Pro Leu Val Ile Lys Ala Leu Lys Gln Tyr Thr Thr
1425                1430                1435                1440

Thr Thr Cys Val Gln Leu Gln Lys Gln Val Leu Asp Leu Leu Ala Gln
            1445                1450                1455

Leu Val Gln Leu Arg Val Asn Tyr Cys Leu Leu Asp Ser Asp Gln Val
        1460                1465                1470

Phe Ile Gly Phe Val Leu Lys Gln Phe Glu Tyr Ile Glu Val Gly Gln
    1475                1480                1485

Phe Arg Glu Ser Glu Ala Ile Ile Pro Asn Ile Phe Phe Phe Leu Val
1490                1495                1500

Leu Leu Ser Tyr Glu Arg Tyr His Ser Lys Gln Ile Ile Gly Ile Pro
1505                1510                1515                1520

Lys Ile Ile Gln Leu Cys Asp Gly Ile Met Ala Ser Gly Arg Lys Ala
            1525                1530                1535

Val Thr His Ala Ile Pro Ala Leu Gln Pro Ile Val His Asp Leu Phe
        1540                1545                1550

Val Leu Arg Gly Thr Asn Lys Ala Asp Ala Gly Lys Glu Leu Glu Thr
    1555                1560                1565

Gln Lys Glu Val Val Val Ser Met Leu Leu Arg Leu Ile Gln Tyr His
1570                1575                1580

Gln Val Leu Glu Met Phe Ile Leu Val Leu Gln Gln Cys His Lys Glu
1585                1590                1595                1600

Asn Glu Asp Lys Trp Lys Arg Leu Ser Arg Gln Ile Ala Asp Ile Ile
            1605                1610                1615

Leu Pro Met Leu Ala Lys Gln Gln Met His Ile Asp Ser His Glu Ala
        1620                1625                1630

Leu Gly Val Leu Asn Thr Leu Phe Glu Ile Leu Ala Pro Ser Ser Leu
    1635                1640                1645

Arg Pro Val Asp Met Leu Leu Arg Ser Met Phe Val Thr Pro Asn Thr
1650                1655                1660

Met Ala Ser Val Ser Thr Val Gln Leu Trp Ile Ser Gly Ile Leu Ala
1665                1670                1675                1680

Ile Leu Arg Val Leu Ile Ser Gln Ser Thr Glu Asp Ile Val Leu Ser
            1685                1690                1695

Arg Ile Gln Glu Leu Ser Phe Ser Pro Tyr Leu Ile Ser Cys Thr Val
        1700                1705                1710

Ile Asn Arg Leu Arg Asp Gly Asp Ser Thr Ser Thr Leu Glu Glu His
    1715                1720                1725

Ser Glu Gly Lys Gln Ile Lys Asn Leu Pro Glu Glu Thr Phe Ser Arg
1730                1735                1740

Phe Leu Leu Gln Leu Val Gly Ile Leu Leu Glu Asp Ile Val Thr Lys
1745                1750                1755                1760

-continued

Gln Leu Lys Val Glu Met Ser Glu Gln Gln His Thr Phe Tyr Cys Gln
            1765                1770                1775

Glu Leu Gly Thr Leu Leu Met Cys Leu Ile His Ile Phe Lys Ser Gly
            1780                1785                1790

Met Phe Arg Arg Ile Thr Ala Ala Thr Arg Leu Phe Arg Ser Asp
        1795                1800                1805

Gly Cys Gly Gly Ser Phe Tyr Thr Leu Asp Ser Leu Asn Leu Arg Ala
            1810                1815                1820

Arg Ser Met Ile Thr Thr His Pro Ala Leu Val Leu Trp Cys Gln
1825                1830                1835                1840

Ile Leu Leu Leu Val Asn His Thr Asp Tyr Arg Trp Trp Ala Glu Val
                1845                1850                1855

Gln Gln Thr Pro Lys Arg His Ser Leu Ser Ser Thr Lys Leu Leu Ser
            1860                1865                1870

Pro Gln Met Ser Gly Glu Glu Glu Asp Ser Asp Leu Ala Ala Lys Leu
            1875                1880                1885

Gly Met Cys Asn Arg Glu Ile Val Arg Arg Gly Ala Leu Ile Leu Phe
            1890                1895                1900

Cys Asp Tyr Val Cys Gln Asn Leu His Asp Ser Glu His Leu Thr Trp
1905                1910                1915                1920

Leu Ile Val Asn His Ile Gln Asp Leu Ile Ser Leu Ser His Glu Pro
                1925                1930                1935

Pro Val Gln Asp Phe Ile Ser Ala Val His Arg Asn Ser Ala Ala Ser
            1940                1945                1950

Gly Leu Phe Ile Gln Ala Ile Gln Ser Arg Cys Glu Asn Leu Ser Thr
            1955                1960                1965

Pro Thr Met Leu Lys Lys Thr Leu Gln Cys Leu Glu Gly Ile His Leu
            1970                1975                1980

Ser Gln Ser Gly Ala Val Leu Thr Leu Tyr Val Asp Arg Leu Leu Cys
1985                1990                1995                2000

Thr Pro Phe Arg Val Leu Ala Arg Met Val Asp Ile Leu Ala Cys Arg
            2005                2010                2015

Arg Val Glu Met Leu Leu Ala Ala Asn Leu Gln Ser Ser Met Ala Gln
            2020                2025                2030

Leu Pro Met Glu Glu Leu Asn Arg Ile Gln Glu Tyr Leu Gln Ser Ser
            2035                2040                2045

Gly Leu Ala Gln Arg His Gln Arg Leu Tyr Ser Leu Leu Asp Arg Phe
            2050                2055                2060

Arg Leu Ser Thr Met Gln Asp Ser Leu Ser Pro Ser Pro Val Ser
2065                2070                2075                2080

Ser His Pro Leu Asp Gly Asp Gly His Val Ser Leu Glu Thr Val Ser
            2085                2090                2095

Pro Asp Lys Asp Trp Tyr Val His Leu Val Lys Ser Gln Cys Trp Thr
            2100                2105                2110

Arg Ser Asp Ser Ala Leu Leu Glu Gly Ala Glu Leu Val Asn Arg Ile
            2115                2120                2125

Pro Ala Glu Asp Met Asn Ala Phe Met Met Asn Ser Glu Phe Asn Leu
            2130                2135                2140

Ser Leu Leu Ala Pro Cys Leu Ser Leu Gly Met Ser Glu Ile Ser Gly
2145                2150                2155                2160

Gly Gln Lys Ser Ala Leu Phe Glu Ala Ala Arg Glu Val Thr Leu Ala
            2165                2170                2175

```
Arg Val Ser Gly Thr Val Gln Gln Leu Pro Ala Val His His Val Phe
            2180                2185                2190

Gln Pro Glu Leu Pro Ala Glu Pro Ala Ala Tyr Trp Ser Lys Leu Asn
    2195                2200                2205

Asp Leu Phe Gly Asp Ala Ala Leu Tyr Gln Ser Leu Pro Thr Leu Ala
2210                2215                2220

Arg Ala Leu Ala Gln Tyr Leu Val Val Ser Lys Leu Pro Ser His
2225                2230                2235                2240

Leu His Leu Pro Pro Glu Lys Glu Lys Asp Ile Val Lys Phe Val Val
            2245                2250                2255

Ala Thr Leu Glu Ala Leu Ser Trp His Leu Ile His Glu Gln Ile Pro
            2260                2265                2270

Leu Ser Leu Asp Leu Gln Ala Gly Leu Asp Cys Cys Cys Leu Ala Leu
            2275                2280                2285

Gln Leu Pro Gly Leu Trp Ser Val Ser Ser Thr Glu Phe Val Thr
            2290                2295                2300

His Ala Cys Ser Leu Ile Tyr Cys Val His Phe Ile Leu Glu Ala Val
2305                2310                2315                2320

Ala Val Gln Pro Gly Glu Gln Leu Leu Ser Pro Glu Arg Arg Thr Asn
            2325                2330                2335

Thr Pro Lys Ala Ile Ser Glu Glu Glu Glu Val Asp Pro Asn Thr
            2340                2345                2350

Gln Asn Pro Lys Tyr Ile Thr Ala Ala Cys Glu Met Val Ala Glu Met
    2355                2360                2365

Val Glu Ser Leu Gln Ser Val Leu Ala Leu Gly His Lys Arg Asn Ser
    2370                2375                2380

Gly Val Pro Ala Phe Leu Thr Pro Leu Leu Arg Asn Ile Ile Ile Ser
2385                2390                2395                2400

Leu Ala Arg Leu Pro Leu Val Asn Ser Tyr Thr Arg Val Pro Pro Leu
            2405                2410                2415

Val Trp Lys Leu Gly Trp Ser Pro Lys Pro Gly Gly Asp Phe Gly Thr
            2420                2425                2430

Ala Phe Pro Glu Ile Pro Val Glu Phe Leu Gln Glu Lys Glu Val Phe
            2435                2440                2445

Lys Glu Phe Ile Tyr Arg Ile Asn Thr Leu Gly Trp Thr Ser Arg Thr
    2450                2455                2460

Gln Phe Glu Glu Thr Trp Ala Thr Leu Leu Gly Val Leu Val Thr Gln
2465                2470                2475                2480

Pro Leu Val Met Glu Gln Glu Glu Ser Pro Pro Glu Glu Asp Thr Glu
            2485                2490                2495

Arg Thr Gln Ile Asn Val Leu Ala Val Gln Ala Ile Thr Ser Leu Val
    2500                2505                2510

Leu Ser Ala Met Thr Val Pro Val Ala Gly Asn Pro Ala Val Ser Cys
    2515                2520                2525

Leu Glu Gln Gln Pro Arg Asn Lys Pro Leu Lys Ala Leu Asp Thr Arg
    2530                2535                2540

Phe Gly Arg Lys Leu Ser Ile Ile Arg Gly Ile Val Glu Gln Glu Ile
2545                2550                2555                2560

Gln Ala Met Val Ser Lys Arg Glu Asn Ile Ala Thr His His Leu Tyr
            2565                2570                2575

Gln Ala Trp Asp Pro Val Pro Ser Leu Ser Pro Ala Thr Thr Gly Ala
            2580                2585                2590
```

-continued

```
Leu Ile Ser His Glu Lys Leu Leu Gln Ile Asn Pro Glu Arg Glu
        2595                2600                2605

Leu Gly Ser Met Ser Tyr Lys Leu Gly Gln Val Ser Ile His Ser Val
        2610                2615                2620

Trp Leu Gly Asn Ser Ile Thr Pro Leu Arg Glu Glu Trp Asp Glu
2625                2630                2635                2640

Glu Glu Glu Glu Glu Ala Asp Ala Pro Ala Pro Ser Ser Pro Pro Thr
                2645                2650                2655

Ser Pro Val Asn Ser Arg Lys His Arg Ala Gly Val Asp Ile His Ser
        2660                2665                2670

Cys Ser Gln Phe Leu Leu Glu Leu Tyr Ser Arg Trp Ile Leu Pro Ser
        2675                2680                2685

Ser Ser Ala Arg Arg Thr Pro Ala Ile Leu Ile Ser Glu Val Val Arg
        2690                2695                2700

Ser Leu Leu Val Val Ser Asp Leu Phe Thr Glu Arg Asn Gln Phe Glu
2705                2710                2715                2720

Leu Met Tyr Val Thr Leu Thr Glu Leu Arg Arg Val His Pro Ser Glu
        2725                2730                2735

Asp Glu Ile Leu Ala Gln Tyr Leu Val Pro Ala Thr Cys Lys Ala Ala
        2740                2745                2750

Ala Val Leu Gly Met Asp Lys Ala Val Ala Glu Pro Val Ser Arg Leu
        2755                2760                2765

Leu Glu Ser Thr Leu Arg Ser Ser His Leu Pro Ser Arg Val Gly Ala
        2770                2775                2780

Leu His Gly Val Leu Tyr Val Leu Glu Cys Asp Leu Leu Asp Asp Thr
2785                2790                2795                2800

Ala Lys Gln Leu Ile Pro Val Ile Ser Asp Tyr Leu Leu Ser Asn Leu
        2805                2810                2815

Lys Gly Ile Ala His Cys Val Asn Ile His Ser Gln Gln His Val Leu
        2820                2825                2830

Val Met Cys Ala Thr Ala Phe Tyr Leu Ile Glu Asn Tyr Pro Leu Asp
        2835                2840                2845

Val Gly Pro Glu Phe Ser Ala Ser Ile Ile Gln Met Cys Gly Val Met
        2850                2855                2860

Leu Ser Gly Ser Glu Glu Ser Thr Pro Ser Ile Ile Tyr His Cys Ala
2865                2870                2875                2880

Leu Arg Gly Leu Glu Arg Leu Leu Leu Ser Glu Gln Leu Ser Arg Leu
        2885                2890                2895

Asp Ala Glu Ser Leu Val Lys Leu Ser Val Asp Arg Val Asn Val His
        2900                2905                2910

Ser Pro His Arg Ala Met Ala Ala Leu Gly Leu Met Leu Thr Cys Met
        2915                2920                2925

Tyr Thr Gly Lys Glu Lys Val Ser Pro Gly Arg Thr Ser Asp Pro Asn
        2930                2935                2940

Pro Ala Ala Pro Asp Ser Glu Ser Val Ile Val Ala Met Glu Arg Val
2945                2950                2955                2960

Ser Val Leu Phe Asp Arg Ile Arg Lys Gly Phe Pro Cys Glu Ala Arg
        2965                2970                2975

Val Val Ala Arg Ile Leu Pro Gln Phe Leu Asp Asp Phe Phe Pro Pro
        2980                2985                2990

Gln Asp Ile Met Asn Lys Val Ile Gly Glu Phe Leu Ser Asn Gln Gln
        2995                3000                3005
```

```
Pro Tyr Pro Gln Phe Met Ala Thr Val Val Tyr Lys Val Phe Gln Thr
    3010                3015                3020

Leu His Ser Thr Gly Gln Ser Ser Met Val Arg Asp Trp Val Met Leu
3025                3030                3035                3040

Ser Leu Ser Asn Phe Thr Gln Arg Ala Pro Val Ala Met Ala Thr Trp
            3045                3050                3055

Ser Leu Ser Cys Phe Phe Val Ser Ala Ser Thr Ser Pro Trp Val Ala
        3060                3065                3070

Ala Ile Leu Pro His Val Ile Ser Arg Met Gly Lys Leu Glu Gln Val
            3075                3080            3085

Asp Val Asn Leu Phe Cys Leu Val Ala Thr Asp Phe Tyr Arg His Gln
    3090                3095                3100

Ile Glu Glu Glu Leu Asp Arg Arg Ala Phe Gln Ser Val Leu Glu Val
3105                3110                3115                3120

Val Ala Ala Pro Gly Ser Pro Tyr His Arg Leu Leu Thr Cys Leu Arg
                3125                3130                3135

Asn Val His Lys Val Thr Thr Cys
            3140
```

```
<210> SEQ ID NO 3
<211> LENGTH: 40
<212> TYPE: DNA
<213> ORGANISM: Artificial Sequence
<220> FEATURE:
<223> OTHER INFORMATION: synthetic construct

<400> SEQUENCE: 3
ugcagcugau caucgaugug cugacccuga ggaacaguuc                40

<210> SEQ ID NO 4
<211> LENGTH: 40
<212> TYPE: DNA
<213> ORGANISM: Artificial Sequence
<220> FEATURE:
<223> OTHER INFORMATION: synthetic construct

<400> SEQUENCE: 4
gaacuguucc ucaggqucag cacaucgaug aucagcugca                40

<210> SEQ ID NO 5
<211> LENGTH: 21
<212> TYPE: DNA
<213> ORGANISM: Artificial Sequence
<220> FEATURE:
<223> OTHER INFORMATION: synthetic construct

<400> SEQUENCE: 5
tgtgctgact ctgaggaaca g                                    21

<210> SEQ ID NO 6
<211> LENGTH: 21
<212> TYPE: DNA
<213> ORGANISM: Artificial Sequence
<220> FEATURE:
<223> OTHER INFORMATION: synthetic construct

<400> SEQUENCE: 6
ugugcugacu cugaggaaca g                                    21
```

<210> SEQ ID NO 7
<211> LENGTH: 21
<212> TYPE: DNA
<213> ORGANISM: Artificial Sequence
<220> FEATURE:
<223> OTHER INFORMATION: synthetic construct

<400> SEQUENCE: 7 cguuccuca gagucagcac a                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic construct

<400> SEQUENCE: 8
catacctcaa actgcatgat g                                             21

<210> SEQ ID NO 9
<211> LENGTH: 21
<212> TYPE: DNA
<213> ORGANISM: Artificial Sequence
<220> FEATURE:
<223> OTHER INFORMATION: synthetic construct

<400> SEQUENCE: 9
cauaccucaa acugcaugau g                                             21

<210> SEQ ID NO 10
<211> LENGTH: 21
<212> TYPE: DNA
<213> ORGANISM: Artificial Sequence
<220> FEATURE:
<223> OTHER INFORMATION: synthetic construct

<400> SEQUENCE: 10
caucaugcag uuugaggu au g                                            21

<210> SEQ ID NO 11
<211> LENGTH: 21
<212> TYPE: DNA
<213> ORGANISM: Artificial Sequence
<220> FEATURE:
<223> OTHER INFORMATION: synthetic construct

<400> SEQUENCE: 11
gcctgcagag ccggcggcct a                                             21

<210> SEQ ID NO 12
<211> LENGTH: 21
<212> TYPE: DNA
<213> ORGANISM: Artificial Sequence
<220> FEATURE:
<223> OTHER INFORMATION: synthetic construct

<400> SEQUENCE: 12
gccugcagag ccggcggccu a                                             21

<210> SEQ ID NO 13
<211> LENGTH: 21
<212> TYPE: DNA
<213> ORGANISM: Artificial Sequence
<220> FEATURE:
<223> OTHER INFORMATION: synthetic construct

```
<400> SEQUENCE: 13
uaggccgccg gcucugcagg c                                              21

<210> SEQ ID NO 14
<211> LENGTH: 21
<212> TYPE: DNA
<213> ORGANISM: Artificial Sequence
<220> FEATURE:
<223> OTHER INFORMATION: synthetic construct

<400> SEQUENCE: 14
acagagtttg tgacccacgc c                                              21

<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
acagaguuug ugacccacgc c                                              21

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
ggcguggguc acaaacucug u                                              21

<210> SEQ ID NO 17
<211> LENGTH: 21
<212> TYPE: DNA
<213> ORGANISM: Artificial Sequence
<220> FEATURE:
<223> OTHER INFORMATION: synthetic construct

<400> SEQUENCE: 17
tccctcatct actgtgtgca c                                              21

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
ucccucaucu acugugugca c                                              21

<210> SEQ ID NO 19
<211> LENGTH: 21
<212> TYPE: DNA
<213> ORGANISM: Artificial Sequence
<220> FEATURE:
<223> OTHER INFORMATION: synthetic construct

<400> SEQUENCE: 19
gugcacacag uagaugaggg a                                              21
```

```
<210> SEQ ID NO 20
<211> LENGTH: 5
<212> TYPE: DNA
<213> ORGANISM: Artificial Sequence
<220> FEATURE:
<223> OTHER INFORMATION: synthetic construct

<400> SEQUENCE: 20 ugugc                                                                    5

<210> SEQ ID NO 21
<211> LENGTH: 7
<212> TYPE: DNA
<213> ORGANISM: Artificial Sequence
<220> FEATURE:
<223> OTHER INFORMATION: synthetic construct

<400> SEQUENCE: 21 gcacauc                                                                  7

<210> SEQ ID NO 22
<211> LENGTH: 5
<212> TYPE: DNA
<213> ORGANISM: Artificial Sequence
<220> FEATURE:
<223> OTHER INFORMATION: synthetic construct

<400> SEQUENCE: 22 guugc                                                                    5

<210> SEQ ID NO 23
<211> LENGTH: 7
<212> TYPE: DNA
<213> ORGANISM: Artificial Sequence
<220> FEATURE:
<223> OTHER INFORMATION: synthetic construct

<400> SEQUENCE: 23 ggaagag                                                                  7

<210> SEQ ID NO 24
<211> LENGTH: 21
<212> TYPE: DNA
<213> ORGANISM: Artificial Sequence
<220> FEATURE:
<223> OTHER INFORMATION: synthetic construct

<400> SEQUENCE: 24
ugugcugacc cugaggaaca g                                                 21

<210> SEQ ID NO 25
<211> LENGTH: 21
<212> TYPE: DNA
<213> ORGANISM: Artificial Sequence
<220> FEATURE:
<223> OTHER INFORMATION: synthetic construct

<400> SEQUENCE: 25
guuccucagg gucagcacau c                                                 21

<210> SEQ ID NO 26
<211> LENGTH: 21
<212> TYPE: DNA
<213> ORGANISM: Artificial Sequence
<220> FEATURE:
<223> OTHER INFORMATION: synthetic construct
```

```
<400> SEQUENCE: 26
ugugcugacc cugaggaaaa g                                              21

<210> SEQ ID NO 27
<211> LENGTH: 21
<212> TYPE: DNA
<213> ORGANISM: Artificial Sequence
<220> FEATURE:
<223> OTHER INFORMATION: synthetic construct

<400> SEQUENCE: 27
uuuccucagg gucagcacau c                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic construct

<400> SEQUENCE: 28
ugugcugacc cugaggaaaa g                                              21

<210> SEQ ID NO 29
<211> LENGTH: 21
<212> TYPE: DNA
<213> ORGANISM: Artificial Sequence
<220> FEATURE:
<223> OTHER INFORMATION: synthetic construct

<400> SEQUENCE: 29
guuccucagg gucagcacau c                                              21

<210> SEQ ID NO 30
<211> LENGTH: 42
<212> TYPE: DNA
<213> ORGANISM: Artificial Sequence
<220> FEATURE:
<223> OTHER INFORMATION: synthetic construct

<400> SEQUENCE: 30
gcgtaatacg actcactata ggaacagtat gtctcagaca tc                       42

<210> SEQ ID NO 31
<211> LENGTH: 21
<212> TYPE: DNA
<213> ORGANISM: Artificial Sequence
<220> FEATURE:
<223> OTHER INFORMATION: synthetic construct

<400> SEQUENCE: 31
uucgaaguau uccgcguacg u                                              21

<210> SEQ ID NO 32
<211> LENGTH: 42
<212> TYPE: DNA
<213> ORGANISM: Artificial Sequence
<220> FEATURE:
<223> OTHER INFORMATION: synthetic construct

<400> SEQUENCE: 32
gcgtaatacg actcactata ggacaagcct aattagtgat gc                       42
```

```
<210> SEQ ID NO 33
<211> LENGTH: 21
<212> TYPE: DNA
<213> ORGANISM: Artificial Sequence
<220> FEATURE:
<223> OTHER INFORMATION: synthetic construct

<400> SEQUENCE: 33
gaacagtatg tctcagacat c                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ucccucaucc acugugugaa c                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcacacagug gaugagggag c                                              21

<210> SEQ ID NO 36
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ccacgccugc ucccucaucc acugugugca cuucauccug                          40

<210> SEQ ID NO 37
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ccacgccugc ucccucaucu acugugugca cuucauccug                          40

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucccucaucu acugugugaa c                                              21
```

```
<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cgagggagua gaugacacac g                                             21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggacaguaa uucaacgcgu c                                             21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
agcguugaau uacugucccc a                                             21

<210> SEQ ID NO 42
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uaagagaugg ggacaguaau ucaacgcuag aagaaca                            37

<210> SEQ ID NO 43
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uaagagaugg ggacaguacu ucaacgcuag aagaaca                            37

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggacaguac uucaacgcgu c                                             21
```

```
<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
accccuguca ugaaguugcg a                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ugccauggcc ugugcugguc c                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cccagcacag gccauggcau c                                              21

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cagatgccat ggcctgtgct gggccag                                        27

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugccauggca ugugcugguc c                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cccagcacau gccuaggcau c                                              21
```

RNA INTERFERENCE FOR THE TREATMENT OF GAIN-OF-FUNCTION DISORDERS

RELATED APPLICATIONS

This application is a continuation of U.S. patent application Ser. No. 12/966,525, filed Dec. 13, 2010, entitled "RNA Interference for the Treatment of Gain-of-Function Disorders," which is a continuation-in-part of U.S. patent application Ser. No. 10/571,705, filed Dec. 9, 2008, entitled "RNA Interference for the Treatment of Gain-of-Function Disorders," which is a national stage application of PCT Application No. PCT/US2004/029968, filed Sep. 13, 2004, which claims the benefit of priority to U.S. Provisional Patent Application No. 60/502,678, filed Sep. 12, 2003. This application is a continuation-in-part of U.S. patent application Ser. No. 12/348,794, filed Jan. 5, 2009, entitled "RNA Silencing Compositions and Methods for the Treatment of Huntington's Disease," which is a continuation of PCT Application No. PCT/US2007/015638, filed Jul. 9, 2007, which claims the benefit of priority to U.S. Provisional Patent Application No. 60/819,704, filed Jul. 7, 2006. The entire contents of the foregoing patent applications are incorporated herein by reference.

STATEMENT AS TO FEDERALLY FUNDED RESEARCH

This invention was made with government support under Grant No. NS038194, awarded by the National Institutions of Health (NIH). The government has certain rights in the invention.

BACKGROUND OF THE INVENTION

RNA interference (RNAi) is the mechanism of sequence-specific, post-transcriptional gene silencing initiated by double-stranded RNAs (dsRNA) homologous to the gene being suppressed. dsRNAs are processed by Dicer, a cellular ribonuclease III, to generate duplexes of about 21 nt with 3'-overhangs (small interfering RNA, siRNA) which mediate sequence-specific mRNA degradation. In mammalian cells siRNA molecules are capable of specifically silencing gene expression without induction of the unspecific interferon response pathway. Thus, siRNAs have become a new and powerful alternative to other genetic tools such as antisense oligonucleotides and ribozymes to analyze gene function. Moreover, siRNA's are being developed for therapeutic purposes with the aim of silencing disease genes in humans.

RNA silencing refers to a group of sequence-specific regulatory mechanisms (e.g. RNA interference (RNAi), transcriptional gene silencing (TGS), post-transriptional gene silencing (PTGS), quelling, co-suppression, and translational repression) mediated by RNA silencing agents which result in repression or "silencing" of a corresponding protein-coding gene. RNA silencing has been observed in many types of eurkayotes, including humans, and utility of RNA silencing agents as both therapetics and research tools is the subject of intense interest.

Several types of small (~19-23 nt), noncoding RNAs trigger RNA silencing in eukaryotes, including small interfering RNAs (siRNAs) and microRNAs (miRNAs), also known as small temporal RNAs (stRNAs)). Recent evidence suggests that the two classes of small RNAs are functionally interchangeable, with the choice of RNA silencing mechanism (e.g. RNAi-mediated mRNA cleavage or translational repression) determined largely by the degree of complementarity between the small RNA and its target (Schwarz and Zamore, 2002; Hutvágner and Zamore, 2002; Zeng et al., 2003; Doench et al., 2003). RNA silencing agents with a high degree of complementarity to a corresponding target mRNA have been shown to direct its silencing by the cleavage-based mechanism (Zamore et al., 2000; Elbashir et al., 2001a; Rhoades et al., 2002; Reinhart et al., 2002; Llave et al., 2002a; Llave et al., 2002b; Xie et al., 2003; Kasschau et al., 2003; Tang et al., 2003; Chen, 2003). RNA silencing agents with a lower degree of complementarity mediate gene silencing by recruiting the RISC complex to the target mRNA, thereby blocking its translation but leaving the mRNA intact (Mourelatos et al., 2002; Hutvágner and Zamore, 2002; Caudy et al., 2002; Martinez et al., 2002; Abrahante et al., 2003; Brennecke et al., 2003; Lin et al., 2003; Xu et al., 2003).

RNA silencing agents have received particular interest as research tools and therapeutic agents for their ability to knock down expression of a particular protein with a high degree of sequence specificity. The sequence specificity of RNA silencing agents is particularly useful for allele-specific silencing dominant, gain-of-function gene mutations. Diseases caused by dominant, gain-of-function gene mutations develop in heterozygotes bearing one mutant and one wild type copy of the gene. Some of the best-known diseases of this class are common neurodegenerative diseases, including Alzheimer's disease, Parkinson's disease and amyotrophic lateral sclerosis (ALS; "Lou Gehrig's disease") (Taylor et al., 2002). In these diseases, the exact pathways whereby the mutant proteins cause cell degeneration are not clear, but the origin of the cellular toxicity is known to be the mutant protein.

One group of inherited gain-of-function disorders are known as the trinucleotide repeat diseases. The common genetic mutation among these diseases is an increase in a series of a particular trinucleotide repeat. To date, the most frequent trinucleotide repeat is CAG, which codes for the amino acid glutamine. At least 9 CAG repeat diseases are known and there are more than 20 varieties of these diseases, including Huntington's disease, Kennedy's disease and many spinocerebellar diseases. These disorders share a neurodegenerative component in the brain and/or spinal cord. Each disease has a specific pattern of neurodegeneration in the brain and most have an autosomal dominant inheritance. The onset of the diseases generally occurs at 30 to 40 years of age, but in Huntington's disease CAG repeats in the huntingtin gene of >60 portend a juvenile onset.

Recent research by the instant inventors has shown that the genetic mutation (increase in length of CAG repeats from normal <36 in the huntingtin gene to >36 in disease) is associated with the synthesis of a mutant huntingtin protein, which has >36 polyglutamines (Aronin et al., 1995). It has also been shown that the protein forms cytoplasmic aggregates and nuclear inclusions (Difiglia et al., 1997) and associates with vesicles (Aronin et al., 1999). The precise pathogenic pathways are not known.

Huntington's disease (and by implication other trinucleotide repeat diseases) is believed to be caused, at least in part, by aberrant protein interactions, which cause impairment of critical neuronal processes, neuronal dysfunction and ultimately neuronal death (neurodegeneration in brain areas called the striatum and cortex).

In the search for an effective treatment for these diseases, researchers in this field emphasized understanding the pathogenesis of the disease and initially sought to intercede at the level of the presumed aberrant protein interactions. However, there is no approved treatment for Huntington's disease or other trinucleotide repeat diseases. Accordingly, therapeutic RNA silencing agents capable of silencing Huntingtin proteins are of considerable interest.

SUMMARY OF THE INVENTION

The present invention relates to the methods for treating a variety of gain-of-function diseases. In particular, the invention provides methods for the selective destruction of mutant mRNAs transcribed from gain-of-function mutant genes, thus preventing production of the mutant proteins encoded by such genes. Other RNAi-based methods for destroying mutant genes have been proposed in which siRNAs are targeted to, for example, a point mutation occurring in a single allele in the mutant gene (e.g., the point mutation in the superoxide dismutase (SOD) gene associated with amyotrophic lateral sclerosis (ALS)). However, there is a key difference between ALS and trinucleotide repeat diseases, such as Huntington's disease. ALS has a point mutation in one allele as the genetic change whereas trinucleotide repeat diseases have an expanded CAG repeat region in one allele as the genetic change. Use of RNAi against the expanded CAG repeat region has potential complications. Over 80 normal genes with CAG repeat regions are known to exist in cells. Thus, siRNAs targeting these CAG repeats cannot be used without risking widespread destruction of normal CAG repeat-containing mRNAs. Likewise, targeting non-allele-specific sites would result in loss of both normal and mutant huntingtin causes neuronal dysfunction.

The methods of the invention utilize RNA interference technology (RNAi) against selected polymorphic regions (i.e., regions containing allele-specific or allelic polymorphisms) which are distinct from the site of mutation in the genes encoding mutant proteins. The methodologies of the instant invention are effective treatments for gain-of-function diseases resulting from deletion mutations, insertion mutations, point mutations, and the like, provided that the mutant gene encodes a protein having a function not normally associated with wild type protein.

In a preferred aspect, the methodologies of the instant invention provide an effective treatment for Huntington's disease (HD). The methodologies also provide effective treatments for other polyglutamine disorders and/or trinucleotide repeat disease, as described in detail herein.

Accordingly, in one aspect, the present invention provides a method of treating a subject having or at risk of having a disease characterized or caused by a gain of function mutant protein by administering to the subject an effective amount of an RNAi agent targeting an allelic polymorphism within a gene encoding a mutant protein e.g.,) huntingtin protein, such that sequence-specific interference of a gene occurs resulting in an effective treatment for the disease. In one embodiment, the mutant protein contains an expanded polyglutamine region. In another one embodiment, the gene encoding the mutant protein contains an expanded trinucleotide repeat region.

In a yet another embodiment, the method of the invention can be used to treat Huntington's disease and a variety of other diseases selected from the group consisting of spino-cerebellar ataxia type 1, spino-cerebellar ataxia type 2, spino-cerebellar ataxia type 3, spino-cerebellar ataxia type 6, spino-cerebellar ataxia type 7, spino-cerebellar ataxia type 8, spino-cerebellar ataxia type 12, myotonic dystrophy, spinal bulbar muscular disease and dentatoiubral-pallidoluysian atrophy.

The method of the invention uses RNAi agents homologous to an allelic polymorphism within the gene encoding, for example, a mutant huntingtin protein for the treatment of Huntington's disease. In a preferred embodiment, the RNAi agent targets allelic polymorphism selected from the group consisting of P1-P5. In a further preferred embodiment, the RNAi agent targets an allelic polymorphism selected from the group consisting of P6-P43.

In a further embodiment, the invention provides RNAi agents comprising of a first and second strand each containing 16-25 nucleotides. The first strand of the present invention is homologous to a region of a gene encoding a gain-of-function mutant protein, wherein the nucleotide sequence of the gain-of-function mutant protein comprises an allelic polymorphism. The second strand includes 16-25 nucleotides complementary to the first strand. The RNAi agent can also have a loop portion comprising 4-11, e.g., 4, 5, 6, 7, 8, 9, 10, 11, nucleotides that connects the two nucleotides sequences. In still other embodiments, the target region of the mRNA sequence is located in a 5' untranslated region (UTR) or a 3' UTR of the mRNA of a mutant protein.

In another embodiment, the invention provides an expression construct comprising an isolated nucleic acid that encodes a nucleic acid molecule with a first sequence of 16-25 nucleotides homologous to an allelic polymorphism within, for example, the gene encoding a mutant huntingtin protein. The expression construct can be for example, a viral vector, retroviral vector, expression cassette or plasmid. The expression construct can also have an RNA polymerase II promoter sequence or RNA Polymerase II promoter sequence, such as, U6 snRNA promoter of H1 promoter.

In yet other embodiments, the present invention provides host cells e.g.,) mammalian cells) comprising nucleic acid molecules and expression constructs of the present invention.

In still other embodiments, the present invention provides therapeutic compositions comprising the nucleic acid molecules of the invention and a pharmaceutically acceptable carrier.

In other aspects, the present invention is based, at least in part, on the discovery of single nucleotide polymorphism (SNP) sites in the Huntingtin (htt) gene which are preferred target sites for RNA silencing. The htt SNP sites of the invention are relatively prevalent within a sample population. In particular, the htt SNPs of the invention are present within a population at an allelic frequency of at least 30%. Such SNPs sites may be analysed in a patient to determine if they are heterozygous. Each SNP allele of a heterozygous SNP site may then be sequenced in the patient to determine which SNP allele is linked with the expanded CAG repeat region of the HD-associated allele to form a HD-associated haplotype. Such HD-associated htt SNPs are attractive targets for therapeutic RNA silencing agents and circumvent complications associated with directly targeting the expanded CAG repeat region of htt. Over 80 normal genes with CAG repeat regions are known to exist in cells. Thus, RNA silencing agents targeting these CAG repeats cannot be used without risking widespread destruction of normal CAG repeat-containing mRNAs. Likewise, targeting non-allele-specific sites would result in loss of both normal and mutant huntingtin causes neuronal dysfunction.

In one aspect, the invention is directed to a method of treating a subject having or at risk for Huntington's disease, comprising: administering to said subject an effective amount of a RNA silencing agent targeting a heterozygous single nucleotide polymorphism (SNP) within a target mRNA encoding a mutant huntingtin (htt) protein, such that RNA silencing of said mRNA occurs; thereby treating said disease in said subject, wherein the SNP has an allelic frequency of at least 10% (e.g., at least 15%, 20%, 25%, 30%, 35%, 40% or more) in a sample population.

In another aspect, the invention is directed to a method of silencing a target mRNA encoding a mutant huntingtin (htt) protein in a cell, comprising contacting the cell with effective amount of a RNA silencing agent targeting a heterozygous single nucleotide polymorphism (SNP) within the target mRNA, such that RNA silencing of said mRNA occurs, wherein the SNP has an allelic frequency of at least 10% (e.g., at least 15%, 20%, 25%, 30%, 35%, 40% or more) in a sample population.

In another aspect, the invention is directed to an RNA silencing agent comprising an antisense strand comprising about 16-25 nucleotides homologous to a region of an mRNA encoding a mutant huntingtin (htt) protein, said region comprising a heterozygous single nucleotide polymorphism (SNP) allele having an allelic frequency of at least 10% (e.g., at least 15%, 20%, 25%, 30%, 35%, 40% or more) in a sample population, wherein the RNA silencing agent is capable of directing RNA silencing of said mRNA. In certain embodiments, the heterozygous SNP allele is found at a SNP site selected from the group consisting of RS362331, RS4690077, RS363125, 47 bp into Exon 25, RS363075, RS362268, RS362267, RS362307, RS362306, RS362305, RS362304, and RS362303.

In one embodiment, the SNP allele is present at SNP target site RS363125. In a particular embodiment, the SNP allele is a C nucleotide. In another particular embodiment, the SNP allele is a U nucleotide.

In another embodiment, the SNP allele is present at SNP target site RS362331. In a particular embodiment, the SNP allele is an A nucleotide. In another particular embodiment, the SNP allele is a C nucleotide.

In one embodiment, the target mRNA comprises the sequence set forth as SEQ ID NO: 36. In another embodiment, the target mRNA comprises the sequence set forth as SEQ ID NO: 37. In another embodiment, the target mRNA comprises the sequence set forth as SEQ ID NO: 42. In another embodiment, the target mRNA comprises the sequence set forth as SEQ ID NO:43. In another embodiment, the target mRNA comprises the sequence set forth as SEQ ID NO:48.

In certain embodiments, the RNA silencing agent is capable of inducing discriminatory RNA silencing.

In one embodiment, the antisense strand of said RNA silencing agent is complementary to the SNP and wherein said RNA silencing agent is capable of substantially silencing the mutant huntingtin protein without substantially silencing the corresponding wild-type huntingtin protein.

In certain preferred embodiments, the RNA silencing agent is an siRNA. In one embodiment, the siRNA comprises (i) a sense strand comprising the sequence set forth as SEQ ID NO: 34; and (ii) an antisense strand comprising the sequence set forth as SEQ ID NO: 35. In another embodiment, the siRNA comprises (i) a sense strand comprising the sequence set forth as SEQ ID NO: 38; and (ii) an antisense strand comprising the sequence set forth as SEQ ID NO: 39. In another embodiment, the siRNA comprises (i) a sense strand comprising the sequence set forth as SEQ ID NO:40; and (ii) an antisense strand comprising the sequence set forth as SEQ ID NO:41. In another embodiment, the siRNA comprises (i) a sense strand comprising the sequence set forth as SEQ ID NO:44; and (ii) an antisense strand comprising the sequence set forth as SEQ ID NO:45. In another embodiment, the siRNA comprises (i) a sense strand comprising the sequence set forth as SEQ ID NO:46; and (ii) an antisense strand comprising the sequence set forth as SEQ ID NO:47. In another embodiment, the siRNA comprises (i) a sense strand comprising the sequence set forth as SEQ ID NO:49; and (ii) an antisense strand comprising the sequence set forth as SEQ ID NO:50. In another embodiment, at least one nucleotide of the siRNA is modified with a nucleotide analog or backbone modification (e.g., a phosphorothioate or Locked Nucleic Acid (LNA) modification) which confers, for example, enhanced nuclease resistance.

In other embodiments, the siRNA comprises a lipophilic moiety. In a particular preferred embodiment, the lipophilic moiety is a cholesterol moiety.

In other embodiments, the siRNA is an asymmetric siRNA.

In certain embodiments, the subject is identified as having said SNP by (i) providing DNA from the subject; and (ii) sequencing the huntingtin gene, or portion thereof, using said DNA. In other embodiments, the sample population is of Western European origin.

Other features and advantages of the invention will be apparent from the following detailed description and claims.

BRIEF DESCRIPTION OF THE DRAWINGS

FIG. 1a-k: Human huntingtin gene, nucleotide sequence (SEQ ID NO:1)

FIG. 2a-b: Human huntingtin protein, amino acid sequence (SEQ ID NO:2)

FIG. 3: Sense (SEQ ID NO: 3) and antisense (SEQ ID NO: 4) of the huntingtin (htt) target RNA sequence FIG. 4: Thermodynamic analysis of siRNA strand 5' ends for the siRNA duplex FIG. 5a-c: In vitro RNAi reactions programmed with siRNA targeting a polymorphism within the huntingtin (htt) mRNA. (a) Standard siRNA. (b) siRNA improved by reducing the base-pairing strength of the 5' end of the anti-sense strand of the siRNA duplex. (c) siRNA improved by reducing the unpairing the 5' end of the anti-sense strand of the siRNA duplex.

FIG. 7: Frequency of SNP heterozygosity at SNP sites located in the human Huntingtin gene. The identity of the SNP at each SNP site in the target gene and target mRNA are also indicated.

FIG. 8a-b: In vitro RNAi reactions programmed with siRNA targeting a first SNP allele (C) in the heterozygous SNP site RS363331 within the human huntingtin gene. (a) Sequence of the siRNA (SEQ ID NO: 34; sense strand; SEQ ID NO: 35, guide strand), which is fully complementary to the target hht mRNA containing the "C" SNP allele (SEQ ID NO: 36) but which forms a G:U mismatch at position 10 (P10) with the non-target mRNA encoded by the corresponding "U" SNP (SEQ ID NO: 37). (b) Discriminatory RNA silencing (expressed as units of luciferase reporter gene activity relative to GFP) by the siRNA in (a) for the targeted "U" SNP allele ("match") versus the non-targeted "C" SNP allele ("mismatch").

FIG. 10a-b: In vitro RNAi reactions programmed with siRNA targeting a first SNP allele (A) in the heterozygous SNP site RS363125 within the human huntingtin gene. (a) Sequence of the siRNA (SEQ ID NO: 40; sense strand; SEQ ID NO: 41, guide strand), which is fully complementary to the target hht mRNA containing the "A" SNP allele (SEQ ID NO: 42) but which forms a U:C mismatch at position 10 (P10) with the non-target mRNA encoded by the corresponding "C" SNP (SEQ ID NO: 43). (b) Discriminatory RNA silencing (expressed as units of luciferase reporter gene activity relative to GFP) by the siRNA in (a) for the targeted "A" SNP allele ("match") versus the non-targeted "C" SNP allele ("mismatch").

FIG. 11a-b: In vitro RNAi reactions programmed with siRNA targeting the second SNP allele ("C") at the heterozygous SNP site RS363125 within the human huntingtin gene. (a) Sequence of the siRNA (SEQ ID NO: 44; sense strand; SEQ ID NO: 45, guide strand) which is fully complementary to the target hht mRNA containing the "C" SNP allele (SEQ ID NO: 43) but which forms a G:A mismatch at position 10 (P10) with the non-target mRNA encoded by the corresponding "C" SNP (SEQ ID NO: 42). (b) Discriminatory RNA silencing (expressed as units of luciferase reporter gene activity relative to GFP) by the siRNA in (a) for the targeted "C" SNP allele ("match") versus the non-targeted "A" SNP allele ("mismatch").

FIG. 12a-d: In vitro RNAi reactions performed in HEK cells homozygous for the C polymorphism in the 3' UTR of the human huntingtin (htt) gene. (a) Sequence of a matched siRNA (SEQ ID NO:46, sense strand; SEQ ID NO:47, guide strand) having a guide strand that is perfectly complementary to the target site in the homozygous target allele (SEQ ID NO:48). (b) Sequence of a mismatched siRNA (SEQ ID NO:49, sense strand; SEQ ID NO:50, guide strand) having a guide strand which forms a U:C mismatch at position 10 (P10) with the homozygous target allele. (c) Relative change in htt target mRNA levels in HEK cells transfected with 20 nM of siRNAs depicted in (a) and (b) versus mock transfection as measured by quantitative RT-PCR. (d) Relative change in Htt protein levels in HEK cells transfected with 20 nM of siRNAs depicted in (a) and (b) versus mock transfection as measured by Western blot.

DETAILED DESCRIPTION OF THE INVENTION

Figure 5A:
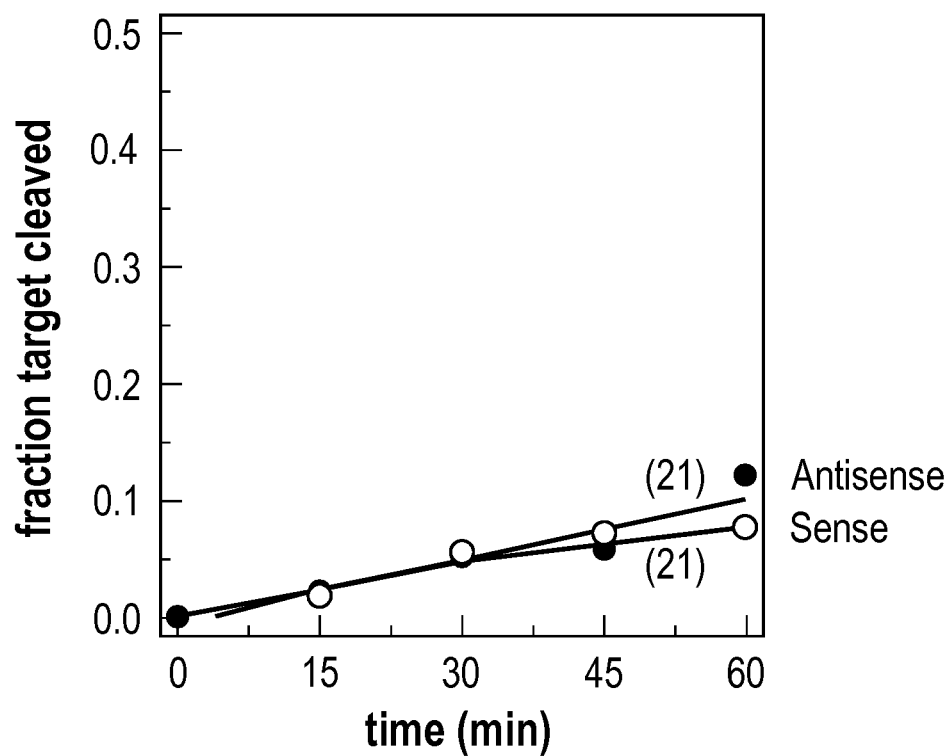

The present invention relates to methods and reagents for treating a variety of gain-of-function diseases. In one aspect, the invention relates to methods and reagents for treating a variety of diseases characterized by a mutation in one allele or copy of a gene, the mutation encoding a protein which is sufficient to contribute to or cause the disease. Preferably, the methods and reagents are used to treat diseases caused or characterized by a mutation that is inherited in an autosomal dominant fashion. In one embodiment, the methods and reagents are used for treating a variety of neurodegenerative disease caused by a gain-of-function mutation, e.g., polyglutamine disorders and/or trinucleotide repeat diseases, for example, Huntington's disease. In another embodiment, the methods and reagents are used for treating diseases caused by a gain-of-function in an oncogene, the mutated gene product being a gain-of-function mutant, e.g., cancers caused by a mutation in the ret oncogene (e.g., ret-1), for example, endocrine tumors, medullary thyroid tumors, parathyroid hormone tumors, multiple endocrine neoplasia type2, and the like. In another embodiment, the methods and reagents of the invention can be used to treat a variety of gastrointestinal cancers known to be caused by an autosomally-inherited, gain-of-function mutations.

The present invention utilizes RNA interference technology (RNAi) against allelic polymorphisms located within a gene encoding a gain-of-function mutant protein. RNAi destroys the corresponding mutant mRNA with nucleotide specificity and selectivity. RNA agents of the present invention are targeted to polymorphic regions of a mutant gene, resulting in cleavage of mutant mRNA. These RNA agents, through a series of protein-nucleotide interactions, function to cleave the mutant mRNAs. Cells destroy the cleaved mRNA, thus preventing synthesis of corresponding mutant protein e.g., the huntingtin protein.

Accordingly, in one aspect, the present invention provides a method of treating a subject having or at risk of having a disease characterized or caused by a gain of function mutant protein by administering to the subject an effective amount of an RNAi agent targeting an allelic polymorphism within a gene encoding a mutant protein e.g.,) huntingtin protein, such that sequence-specific interference of a gene occurs resulting in an effective treatment for the disease. In one embodiment, the mutant protein contains an expanded polyglutamine region. In another one embodiment, the gene encoding the mutant protein contains an expanded trinucleotide repeat region.

In a yet another embodiment, the method of the invention can be used to treat Huntington's disease and a variety of other diseases selected from the group consisting of spino-cerebellar ataxia type 1, spino-cerebellar ataxia type 2, spino-cerebellar ataxia type 3, spino-cerebellar ataxia type 6, spino-cerebellar ataxia type 7, spino-cerebellar ataxia type 8, spino-cerebellar ataxia type 12, myotonic dystrophy, spinal bulbar muscular disease and dentatoiubral-pallidoluysian atrophy.

The method of the invention uses RNAi agents homologous to an allelic polymorphism within the gene encoding, for example, a mutant huntingtin protein for the treatment of Huntington's disease. In a preferred embodiment, the RNAi agent targets allelic polymorphism selected from the group consisting of P1-P5. In a further preferred embodiment, the RNAi agent targets an allelic polymorphism selected from the group consisting of P6-P43.

In a further embodiment, the invention provides RNAi agents comprising of a first and second strand each containing 16-25 nucleotides. The first strand of the present invention is homologous to a region of a gene encoding a gain-of-function mutant protein, wherein the nucleotide sequence of the gain-of-function mutant protein comprises an allelic polymorphism. The second strand includes 16-25 nucleotides complementary to the first strand. The RNAi agent can also have a loop portion comprising 4-11, e.g., 4, 5, 6, 7, 8, 9, 10, 11, nucleotides that connect the two nucleotides sequences. In still other embodiments, the target region of the mRNA sequence is located in a 5' untranslated region (UTR) or a 3' UTR of the mRNA of a mutant protein.

In another embodiment, the invention provides an expression construct comprising an isolated nucleic acid that encodes a nucleic acid molecule with a first sequence of 16-25 nucleotides homologous to an allelic polymorphism within, for example, the gene encoding a mutant huntingtin protein. The expression construct can be for example, a viral vector, retroviral vector, expression cassette or plasmid. The expression construct can also have an RNA polymerase II promoter sequence or RNA Polymerase II promoter sequence, such as, U6 snRNA promoter of H1 promoter.

In yet other embodiments, the present invention provides host cells e.g.,) mammalian cells) comprising nucleic acid molecules and expression constructs of the present invention.

In still other embodiments, the present invention provides therapeutic compositions comprising the nucleic acid molecules of the invention and a pharmaceutically acceptable carrier.

In some embodiments, the present invention utilizes RNA silencing technology (e.g. RNAi) against single nucleotide polymorphisms (SNPs) located within the htt gene encoding the mutant Huntington protein. RNA silencing destroys the corresponding mutant mRNA with single nucleotide specificity and selectivity. RNA silencing agents of the present invention are targeted to polymorphic regions of the mutant htt gene, resulting in cleavage or translational repression of mutant htt mRNA. These RNA silencing agents, through a series of protein-nucleotide interactions, function to cleave or translationally repress the mutant htt mRNAs.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence", e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g. by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homolog (e.g. an ortholog or paralog) of the target gene.

A "target allele" is an allele (e.g., a SNP allele) whose expression is to be selectively inhibited or "silenced." This silencing can be achieved by RNA silencing, e.g. by cleaving the mRNA of the target gene or target allele by a siRNA. The term "non-target allele" is a allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism". In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In preferred embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g. a SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of consecutive glutamine residues linked to peptide bonds. In one embodiment the consecutive region includes at least 5 glutamine residues.

The term "expanded polyglutamine domain" or "expanded polyglutamine segment", as used herein, refers to a segment or domain of a protein that includes at least 35 consecutive glutamine residues linked by peptide bonds. Such expanded segments are found in subjects afflicted with a polyglutamine disorder, as described herein, whether or not the subject has shown to manifest symptoms.

The term "trinucleotide repeat" or "trinucleotide repeat region" as used herein, refers to a segment of a nucleic acid sequence e.g.,) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG, and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE Mental Retardation, Friedreich's ataxia and myotonic dystrophy. Preferred trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The term "polyglutamine disorder" as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also know as Machado-Joseph disease), and spino-cerebellar ataxia type 6, spino-cerebellar ataxia type 7 and dentatoiubral-pallidoluysian atrophy.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g. by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-μ., wherein T is an mRNA targeting moiety, L is a linking moiety, and μ is a miRNA recruiting moiety. As used herein, the terms "mRNA targeting moiety", "targeting moiety", "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g. an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g. an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry", as in the asymmetry of the duplex region of an RNA silencing agent (e.g. the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g, single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, Van der Waals interactions, and the like between said nucleotides (or nucleotide analogs).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (ie. Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of noncomplementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g. double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

I. Polyglutamine Disorders

Polyglutamine disorders are a class of disease or disorders characterized by a common genetic mutation. In particular, the disease or disorders are characterized by an expanded repeat of the trinucleotide CAG which gives rise, in the encoded protein, to an expanded stretch of glutamine residues. Polyglutamine disorders are similar in that the diseases are characterized by a progressive degeneration of nerve cells. Despite their similarities, polyglutamine disorders occur on different chromosomes and thus occur on entirely different segments of DNA. Examples of polyglutamine disorders include Huntington's disease, Dentatorubropallidoluysian Atrophy, Spinobulbar Muscular atrophy, Spinocerebellar Ataxia Type 1, Spinocerebellar Ataxia Type 2, Spinocerebellar Ataxia Type 3, Spinocerebellar Ataxia Type 6 and Spinocerebellar Ataxia Type 7 (Table 3).

TABLE 1

Polyglutamine disorders

| Disease | Gene | Locus | Protein | CAG repeat size Normal | Disease |
|---|---|---|---|---|---|
| Spinobulbar muscular atrophy (Kennedy disease) | AR | Xq13-21 | Androgen receptor (AR) | 9-36 | 38-62 |
| Huntington's disease | HD | 4p16.3 | Huntingtin | 6-35 | 36-121 |
| Dentatorubral-pallidoluysian atrophy (Haw-River syndrome) | DRPLA | 12p13.31 | Atrophin-1 | 6-35 | 49-88 |
| Spinocerebellar ataxia type 1 | SCA1 | 6p23 | Ataxin-1 | 6-44[a] | 39-82 |
| Spinocerebellar ataxia type 2 | SCA2 | 12q24.1 | Ataxin-2 | 15-31 | 36-63 |
| Spinocerebellar ataxia type 3 (Machado-Joseph disease) | SCA3 (MJD1) | 14q32.1 | Ataxin-3 | 12-40 | 55-84 |
| Spinocerebellar ataxia type 6 | SCA6 | 19p13 | $\alpha_{1A}$-voltage-dependent calcium channel subunit | 4-18 | 21-33 |
| Spinocerebellar ataxia type 7 | SCA7 | 13p12-13 | Ataxin-7 | 4-35 | 37-306 |

[a]Alleles with 21 or more repeats are interrupted by 1-3 CAT units; disease alleles contain pure CAG tracts.

Polyglutamine disorders of the invention are characterized by (e.g., domains having between about 30 to 35 glutamine residues, between about 35 to 40 glutamine residues, between about 40 to 45 glutamine residues and having about 45 or more glutamine residues. The polyglutamine domain typically contains consecutive glutamine residues (Q n>36).

II. Huntington Disease

In some embodiments, the RNA silencing agents of the invention are designed to target polymorphisms (e.g. single nucleotide polymorphisms) in the mutant human huntingtin protein (htt) for the treatment of Huntington's disease.

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. CAG repeat varies in number from 8 to 35 in normal individuals (Kremer et al., 1994). The genetic mutation e.g.,) an increase in length of the CAG repeats from normal less than 36 in the huntingtin gene to greater than 36 in the disease is associated with the synthesis of a mutant huntingtin protein, which has greater than 36 polyglutamates (Aronin et al., 1995). In general, individuals with 36 or more CAG repeats will get Huntington's disease. Prototypic for as many as twenty other diseases with a lengthened CAG as the underlying mutation, Huntington's disease still has no effective therapy. A variety of interventions—such as interruption of apoptotic pathways, addition of reagents to boost mitochondrial efficiency, and blockade of NMDA receptors—have shown promise in cell cultures and mouse model of Huntington's disease. However, at best these approaches reveal a short prolongation of cell or animal survival.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Mutant huntingtin (protein) probably accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome—loss of mutant huntingtin.

III. Huntingtin Gene

The disease gene linked to Huntington's disease is termed Huntington or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein. The amino acid sequence of the human huntingtin protein is set forth in FIG. 2 (SEQ ID NO:2).

A consensus nucleotide sequence of the human huntingtin gene (cDNA) is set forth in FIG. 1 (SEQ ID NO:1). The coding region consists of nucleotides 316 to 9750 of SEQ ID NO:1. The two alternative polyadenylation signals are found at nucleotides 10326 to 10331 and nucleotides 13644 to 13649, respectively. The corresponding two polyadenylation sites are found at nucleotides 10348 and 13672, respectively. The first polyadenylation signal/site is that of the 10.3 kb transcript. The second polyadenylation signal/site is that of the 13.7 kb transcript, the predominant transcript in brain.

Five (5) polymorphisms in the human htt gene were identified as described in Example I. An additional 38 polymorphisms in the huntingtin gene sequence have been identified via SNP (single nucleotide polymorphism) analysis (see Table 3). The polymorphisms set forth in Tables 2 and 3 represent preferred sites to target via single-nucleotide-specific RNAi, as described herein.

TABLE 2

Polymorphic sites (P) in the htt gene of human cell lines.

| Cell line | P1 (2886) | P2 (4034) | P3 (6912) | P4 (7222) | P5 (7246) |
|---|---|---|---|---|---|
| GFP-Htt (9kb construct) | C | G | A | T | C |
| HeLa | t | a | A | g | C |
| HEK 293T | t | a | G | g | t |
| HepG2 | t | a | G | g | t |
| FP-4 | t | a | g, A | g | t, C |

TABLE 3

Polymorphic sites (P) in the human htt gene identified by SNP analysis.

| | consensus | polymorphism | | db_xref |
|---|---|---|---|---|
| complement 103 | G | A | P6 | dbSNP: 396875 |
| complement 432 | T | C | P7 | dbSNP: 473915 |
| complement 474 | C | A | P8 | dbSNP: 603765 |
| 1509 | T | C | P9 | dbSNP: 1065745 |
| complement 1857 | T | C | P10 | dbSNP: 2301367 |
| 3565 | G | C, A | P11, P12 | dbSNP: 1065746 |
| 3594 | T | G | P13 | dbSNP: 1143646 |
| 3665 | G | C | P14 | dbSNP: 1065747 |
| complement 4122 | G | A | P15 | dbSNP: 363099 |
| complement 4985 | G | A | P16 | dbSNP: 363129 |
| complement 5480 | T | G | P17 | dbSNP: 363125 |
| 6658 | T | G | P18 | dbSNP: 1143648 |
| complement 6912 | T | C | P19 | dbSNP: 362336 |
| complement 7753 | G | A | P20 | dbSNP: 3025816 |
| complement 7849 | G | C | P21 | dbSNP: 3025814 |
| complement 8478 | T | C | P22 | dbSNP: 2276881 |
| 8574 | T | C | P23 | dbSNP: 2229985 |
| complement 9154 | C | A | P24 | dbSNP: 3025817 |
| 9498 | T | C | P25 | dbSNP: 2229987 |
| complement 9699 | G | A | P26 | dbSNP: 362308 |
| complement 9809 | G | A | P27 | dbSNP: 362307 |
| complement 10064 | T | C | P28 | dbSNP: 362306 |
| complement 10112 | G | C | P29 | dbSNP: 362268 |
| complement 10124 | G | C | P30 | dbSNP: 362305 |
| complement 10236 | T | G | P31 | dbSNP: 362304 |
| complement 10271 | G | A | P32 | dbSNP: 362303 |
| complement 10879 | G | A | P33 | dbSNP: 1557210 |
| complement 10883 | G | A | P34 | dbSNP: 362302 |
| complement 10971 | C | A | P35 | dbSNP: 3025805 |
| complement 11181 | G | A | P36 | dbSNP: 362267 |
| complement 11400 | C | A | P37 | dbSNP: 362301 |
| 11756 . . . 11757 | G | — | P38 | dbSNP: 5855774 |
| 12658 | G | A | P39 | dbSNP: 2237008 |
| complement 12911 | T | C | P40 | dbSNP: 362300 |
| complement 13040 | G | A | P41 | dbSNP: 2530595 |

TABLE 3-continued

Polymorphic sites (P) in the human htt gene identified by SNP analysis.

| | consensus | polymorphism | | db_xref |
|---|---|---|---|---|
| 13482 | G | A | P42 | dbSNP: 1803770 |
| 13563 | G | A | P43 | dbSNP: 1803771 |

The present invention targets mutant huntingtin using RNA interference (Hutvagner et al., 2002). One strand of double-stranded RNA (siRNA) complements a polymorphic region within the mutant huntingtin mRNA. After introduction of siRNA into neurons, the siRNA partially unwinds, binds to polymorphic region within the huntingtin mRNA in a site-specific manner, and activates an mRNA nuclease. This nuclease cleaves the huntingtin mRNA, thereby halting translation of the mutant huntingtin. Cells rid themselves of partially digested mRNA, thus precluding translation, or cells digest partially translated proteins. Neurons survive on the wild-type huntingtin (from the normal allele); this approach prevents the ravages of mutant huntingtin by eliminating its production.

Exemplary single nucleotide polymorphisms in the huntingtin gene sequence can be found at positions 2886, 4034, 6912, 7222, and 7246 of the human htt gene. In certain embodiments, RNA silencing agents of the invention are capable of targeting one of the SNP sites listed in FIG. 7. Genomic sequence for each SNP site can be found in, for example, the publically available "SNP Entrez" database maintained by the NCBI. Additional single nucleotide polymorphisms in the huntingtin gene sequence are set forth in Table 3.

In some embodiments, preferred htt SNPs have an allelic frequency of at least 30% in a sample population of patients. In some embodiments, a targeted htt SNP exhibits a frequency of heterozygosity of at least 25% within a sample patient population (e.g., at least 30, 40, 50, 60, 65, 70, 75, or 80% heterozygosity).

In a particular embodiment, the SNP allele is present at genomic site RS363125. In another embodiment, the SNP allele is present at genomic site RS362331. In another embodiment, the SNP allele is present at position 171, e.g., an A171C polymorphism, in the huntingtin gene according to the sequence numbering in GenBank Accession No. NM_002111 (Aug. 8, 2005).

IV. siRNA Design

In some embodiments, siRNAs are designed as follows. First, a portion of the target gene (e.g., the htt gene) is selected that includes the polymorphism. Exemplary polymorphisms are selected from the 5' untranslated region of a target gene. Cleavage of mRNA at these sites should eliminate translation of corresponding mutant protein. Polymorphisms from other regions of the mutant gene are also suitable for targeting. A sense strand is designed based on the sequence of the selected portion. Preferably the portion (and corresponding sense strand) includes about 19 to 25 nucleotides, e.g., 19, 20, 21, 22, 23, 24 or 25 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to ellicit an interferon or PKR response in certain mammalian cells which may be undesirable. Preferably the RNAi agents of the invention do not ellicit a PKR response (i.e., are of a sufficiently short length). However, longer RNAi agents may be useful, for example, in cell types incapable of generating a PRK response or in situations where the PKR response has been downregulated or dampened by alternative means.

The sense strand sequence is designed such that the polymorphism is essentially in the middle of the strand. For example, if a 21-nucleotide siRNA is chosen, the polymorphism is at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, the polymorphism is at, for example, nucleotide 7, 8, 9, 10, 11, 12, 13, 14, 15 or 16. For a 23-nucleotide siRNA, the polymorphism is at, for example, 7, 8, 9, 10, 11, 12, 13, 14, 15 or 16. For a 24-nucleotide siRNA, the polymorphism is at, for example, 9, 10, 11, 12, 13, 14 or 16. For a 25-nucleotide siRNA, the polymorphism is at, for example, 9, 10, 11, 12, 13, 14, 15, 16 or 17. Moving the polymorphism to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and include complementary nucleotides. In one embodiment, the strands are fully complementary, i.e., the strands are blunt-ended when aligned or annealed. In another embodiment, the strands comprise align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Provisional patent application Nos. 60/475,386 entitled "*Methods and Compositions for Controlling Efficacy of RNA Silencing*" (filed Jun. 2, 2003) and 60/475,331 entitled "*Methods and Compositions for Enhancing the Efficacy and Specificity of RNAi*" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). Preferably, the base pair is selected from the group consisting of an I:A, I:U and I:C. In yet another embodiment, the base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

The design of siRNAs suitable for targeting the htt polymorphisms set forth in Table 2 is described in detail below

```
P1 DNA
                                            (SEQ ID NO: 5)
TGTGCTGACTCTGAGGAACAG sense
                                            (SEQ ID NO: 6)
UGUGCUGACUCUGAGGAACAG antisense
                                            (SEQ ID NO: 7)
ACACGACUGAGACUCCUUGUC (blunt-ends, 21-mer)

(2-nt overhangs) see FIG. 5

P2 DNA
                                            (SEQ ID NO: 8)
CATACCTCAAACTGCATGATG sense
                                            (SEQ ID NO: 9)
CAUACCUCAAACUGCAUGAUG antisense
                                            (SEQ ID NO: 10)
GUAUGGAGUUUGACGUACUAC (blunt ends, 21-mer)

P3 DNA
                                            (SEQ ID NO: 11)
GCCTGCAGAGCCGGCGGCCTA sense
                                            (SEQ ID NO: 12)
GCCUGCAGAGCCGGCGGCCUA antisense
                                            (SEQ ID NO: 13)
CGGACGUCUCGGCCGCCGGAU (blunt ends, 21-mer)

P4 DNA
                                            (SEQ ID NO: 14)
ACAGAGTTTGTGACCCACGCC sense
                                            (SEQ ID NO: 15)
ACAGAGUUUGUGACCCACGCC antisense
                                            (SEQ ID NO: 16)
UGUCUCAAACACUGGGUGCGG (blunt ends, 21-mer)

P5 DNA
                                            (SEQ ID NO: 17)
TCCCTCATCTACTGTGTGCAC sense
                                            (SEQ ID NO: 18)
UCCCUCAUCUACUGUGUGCAC antisense
                                            (SEQ ID NO: 19)
AGGGAGUAGAUGACACACGUG (blunt ends, 21 mer)
``` siRNAs can be designed according to the above exemplary teachings for any other polymorphisms found in the htt gene. Moreover, the technology is applicable to targeting any other disease gene having associated polymorphisms, i.e., non-disease causing polymorphisms.

To validate the effectiveness by which siRNAs destroy mutant mRNAs (e.g., mutant huntingtin mRNA), the siRNA is incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

While the instant invention primarily features targeting polymorphic regions in the target mutant gene (e.g., in mutant htt) distinct from the expanded CAG region mutation, the skilled artisan will appreciate that targeting the mutant region may have applicability as a therapeutic strategy in certain situations. Targeting the mutant region can be accomplished using siRNA that complements CAG in series. The siRNA$^{cag}$ would bind to mRNAs with CAG complementation, but might be expected to have greater opportunity to bind to an extended CAG series. Multiple siRNA$^{cag}$ would bind to the mutant huntingtin mRNA (as opposed to fewer for the wild type huntingtin mRNA); thus, the mutant huntingtin mRNA is more likely to be cleaved. Successful mRNA inactivation using this approach would also eliminate normal or wild-type huntingtin mRNA. Also inactivated, at least to some extent, could be other normal genes (approximately 70) which also have CAG repeats, where their mRNAs could interact with the siRNA. This approach would thus rely on an attrition strategy—more of the mutant huntingtin mRNA would be destroyed than wild type huntingtin mRNA or the other approximately 69 mRNAs that code for polyglutamines.

V. RNAi Agents

The present invention includes siRNA molecules designed, for example, as described above. The siRNA molecules of the invention can be chemically synthesized, or can be transcribed in vitro from a DNA template, or in vivo from e.g., shRNA, or, by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002. supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org: 9331/RNAi/docs/BseRI-BamHI_Strategy.pdf and katandin.cshl.org:9331/RNAi/docs/Web_version_of_PCR_strategy1.pdf.

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, supra).

Synthetic siRNAs can be delivered into cells by methods known in the art, including cationic liposome transfection and electroporation. However, these exogenous siRNA generally show short term persistence of the silencing effect (4~5 days in cultured cells), which may be beneficial in only certain embodiments. To obtain longer term suppression of the target genes (i.e., mutant genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding mutant htt, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals.

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27).

VI. Anti-htt RNA Silencing Agents

The present invention features anti-huntingtin RNA silencing agents (e.g., siRNA and shRNAs), methods of making said RNA silencing agents, and methods (e.g., research and/or therapeutic methods) for using said improved RNA silencing agents (or portions thereof) for RNA silencing of mutant huntingtin protein. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

a) Design of Anti-htt siRNA Molecules

An siRNA molecule of the invention is a duplex consisting of a sense strand and complementary antisense strand, the antisense strand having sufficient complementary to a htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target region e.g., a gain-of-function gene target region, and the other strand is identical or substantially identical to the first strand.

Generally, siRNAs can be designed by using any method known in the art, for instance, by using the following protocol:

1. The siRNA should be specific for a heterozygous single-nucleotide polymorphism (SNP) found in a mutant huntingtin (htt) allele, but not a wild-type huntingtin allele. The first strand should be complementary to this sequence, and the other strand is substantially complementary to the first strand. In one embodiment, the SNP is outside the expanded CAG repeat of the mutant huntingin (htt) allele. In another embodiment, the SNP is outside a coding region of the target gene. Exemplary polymorphisms are selected from the 5' untranslated region (5'-UTR) of a target gene. Cleavage of mRNA at these sites should eliminate translation of corresponding mutant protein. Polymorphisms from other regions of the mutant gene are also suitable for targeting. A sense strand is designed based on the sequence of the selected portion. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to ellicit an interferon or PKR response in certain mammalian cells which may be undesirable. Preferably the RNA silencing agents of the invention do not ellicit a PKR response (i.e., are of a sufficiently short length). However, longer RNA silencing agents may be useful, for example, in cell types incapable of generating a PRK response or in situations where the PKR response has been downregulated or dampened by alternative means.

The siRNA molecules of the invention have sufficient complementarity with the target site such that the siRNA can mediate RNAi. In general, siRNA containing nucleotide sequences sufficiently identical to a portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between the wild type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. siRNAs are designed such that perfect complementarity exists between the siRNA and the target mRNA (e.g., the mutant mRNA) at the polymorphism (e.g., the point mutation), there thus being a mismatch if the siRNA is compared (e.g., aligned) to the reference sequence (e.g., wild type allele or mRNA sequence). The sense strand sequence may be designed such that the polymorphism is essentially in the middle of the strand. For example, if a 21-nucleotide siRNA is chosen, the polymorphism is at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, the polymorphism is at, for example, nucleotide 7, 8, 9, 10, 11, 12, 13, 14, 15 or 16. For a 23-nucleotide siRNA, the polymorphism is at, for example, 7, 8, 9, 10, 11, 12, 13, 14, 15 or 16. For a 24-nucleotide siRNA, the polymorphism is at, for example, 9, 10, 11, 12, 13, 14 or 16. For a 25-nucleotide siRNA, the polymorphism is at, for example, 9, 10, 11, 12, 13, 14, 15, 16 or 17.

In one preferred embodiment, the sense strand of the siRNA is identical to the polymorphism at a nucleotide position that is 10 nucleotides from the 5' end of the sense strand (i.e., position P10).

In another preferred embodiment, the sense strand of the siRNA is identical to the polymorphism at a nucleotide position that is 16 nucleotides from the 5' end of the sense strand (i.e., position P16).

4. siRNAs with single nucleotide specificity are preferably designed such that base paring at the single nucleotide in the corresponding reference (e.g., wild type) sequence is disfavored. For example, designing the siRNA such that purine:purine paring exists between the siRNA and the wild type mRNA at the single nucleotide enhances single nucleotide specificity. The purine:purine paring is selected, for example, from the group G:G, A:G, G:A and A:A pairing. Moreover, purine pyrimidine pairing between the siRNA and the mutant mRNA at the single nucleotide enhances single nucleotide specificity. The purine:pyrimidine paring is selected, for example, from the group G:C, C:G, A:U, U:A, C:A, A:C, U:A and A:U pairing.

5. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant: wild type mismatch is a purine:purine mismatch.

6. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

7. Select one or more sequences that meet your criteria for evaluation.

Further general information about the design and use of siRNA may be found in "The siRNA User Guide," available at The Max-Plank-Institut für Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 (log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

8. To validate the effectiveness by which siRNAs destroy mutant mRNAs (e.g., mutant huntingtin mRNA), the siRNA may be incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Anti-htt siRNAs may be designed to target any of the single nucleotide polymorphisms described supra. Said siRNAs comprise an antisense strand which is fully complementary with the single nucleotide polymorphism. In certain embodiments, the RNA silencing agent is a siRNA.

In certain embodiments, the siRNA comprises (i) a sense strand comprising the sequence set forth as SEQ ID NO: 34; and (ii) an antisense strand comprising the sequence set forth as SEQ ID NO: 35. In another embodiment, the siRNA comprises (i) a sense strand comprising the sequence set forth as SEQ ID NO: 38; and (ii) an antisense strand comprising the sequence set forth as SEQ ID NO: 39. In another embodiment, the siRNA comprises (i) a sense strand comprising the sequence set forth as SEQ ID NO: 40; and (ii) an antisense strand comprising the sequence set forth as SEQ ID NO: 41. In another embodiment, the siRNA comprises (i) a sense strand comprising the sequence set forth as SEQ ID NO: 44; and (ii) an antisense strand comprising the sequence set forth as SEQ ID NO: 45. In another embodiment, the siRNA comprises (i) a sense strand comprising the sequence set forth as SEQ ID NO: 46; and (ii) an antisense strand comprising the sequence set forth as SEQ ID NO: 47. In another embodiment, the siRNA comprises (i) a sense strand comprising the sequence set forth as SEQ ID NO: 49; and (ii) an antisense strand comprising the sequence set forth as SEQ ID NO: 50.

To validate the effectiveness by which siRNAs destroy mutant mRNAs (e.g., mutant huntingtin mRNA), the siRNA is incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

While the instant invention primarily features targeting polymorphic regions in the target mutant gene (e.g., in mutant htt) distinct from the expanded CAG region mutation, the skilled artisan will appreciate that targeting the mutant region may have applicability as a therapeutic strategy in certain situations. Targeting the mutant region can be accomplished using siRNA that complements CAG in series. The siRNA$^{cag}$ would bind to mRNAs with CAG complementation, but might be expected to have greater opportunity to bind to an extended CAG series. Multiple siRNA$^{cag}$ would bind to the mutant huntingtin mRNA (as opposed to fewer for the wild type huntingtin mRNA); thus, the mutant huntingtin mRNA is more likely to be cleaved. Successful mRNA inactivation using this approach would also eliminate normal or wild-type huntingtin mRNA. Also inactivated, at least to some extent, could be other normal genes (approximately 70) which also have CAG repeats, where their mRNAs could interact with the siRNA. This approach would thus rely on an attrition strategy—more of the mutant huntingtin mRNA would be destroyed than wild type huntingtin mRNA or the other approximately 69 mRNAs that code for polyglutamines.

b) siRNA-Like Molecules siRNA-like molecules of the invention have a sequence (i.e., have a strand having a sequence) that is "sufficiently complementary" to a heterozygous SNP of a htt mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of a heterozygous htt SNP with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs, or engineered precursor RNAs, of the instant invention, one portion of the duplex stem is a nucleic acid sequence that is complementary (or anti-sense) to the heterozygous SNP. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., SOD1 or htt mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. *The miRNA Registry; Griffiths-Jones S, Nuc. Acids Res.,* 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (*The miRNA Registry at the Sanger Institute website; Griffiths-Jones S, Nuc. Acids Res.,* 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., *Science*, 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing; accordingly the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-µ, wherein T is an mRNA targeting moiety, L is a linking moiety, and µ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-µ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA. Mammals are reported to have over 250 endogenous miRNAs (Lagos-Quintana et al. (2002) *Current Biol.* 12:735-739; Lagos-Quintana et al. (2001) *Science* 294:858-862; and Lim et al. (2003) *Science* 299:1540). In various embodiments, the miRNA may be any art-recognized miRNA. Table 3 lists some of the known human miRNAs The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O— methylnucleotides, e.g., 2'-β-methyladenosine, 2'-O-methylthymidine, 2'-O-methylguanosine or 2'-O-methyluridine.

VII. Modified Anti-htt RNA Silencing Agents

In certain aspects of the invention, an RNA silencing agent (or any portion thereof) of the invention as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A,G,C,U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analong thereof.

The RNA silencing agents of the invention are preferably modified by the introduction of at least one destabilizing nucleotide within 5 nucleotides from a specificity-determining nucleotide (ie. the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (ie. such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see International Publication No. WO 2005/001045, US Publication No. 2005-0181382 A1). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the aymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleoitde. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6, N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., *Nucleic Acids Res.*, (2005), 33(1): 439-447; Braasch et al. (2003) *Biochemistry* 42:7967-7975, Petersen et al. (2003) *Trends Biotechnol* 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby preorganizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., *Science*, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Preferred embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidine in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In a preferred embodiment, the lipophilic moiety is attached to one end of the sense strand of the siRNA. In another preferred embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In a preferred embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Preferred ligands are coupled, preferably covalently, either directly or indirectly via an intervening tether, to a ligand-conjugated carrier. In preferred embodiments, the ligand is attached to the carrier via an intervening tether. In preferred embodiments, a ligand alters the distribution, targeting or lifetime of an RNA silencing agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B 12, biotin, or an RGD peptide or RGD peptide mimetic.

Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., gyceryl disterarate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). Preferably the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

VIII. Methods of Introducing Nucleic Acids, Vectors, and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In a preferred aspect, the efficacy of an RNAi agent of the invention (e.g., an siRNA targeting a polymorphism in a mutant gene) is tested for its ability to specifically degrade mutant mRNA (e.g., mutant htt mRNA and/or the production of mutant huntingtin protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant huntingtin cDNA). Standard siRNA, modified siRNA or vectors able to produce siRNA from U-looped mRNA are co-transfected. Selective reduction in mutant mRNA (e.g., mutant huntingtin mRNA) and/or mutant protein (e.g., mutant huntingtin) is measured. Reduction of mutant mRNA or protein can be compared to levels of normal mRNA or protein. Exogenously-introduced normal mRNA or protein (or endogenous normal mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

IX. Methods of Treatment:

The present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In a preferred embodiment, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment", or "treating" as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for a polymorphism within the gene, such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a neurological disorder, such as HD. In one embodiment, the patient is diagnosed as having a neurological disorder, and the patient is otherwise in general good health. For example, the patient is not terminally ill, and the patient is likely to live at least 2, 3, 5, or 10 years or longer following diagnosis. The patient can be treated immediately following diagnosis, or treatment can be delayed until the patient is experiencing more debilitating symptoms, such as motor fluctuations and dyskinesis in PD patients. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder, e.g., HD. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

X. Pharmaceutical Compositions and Methods of Administration

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulator compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1:g to 1000 mg may be administered; in some embodiments, 10, 30, 100 or 1000:g may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), supra.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration. For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration.

The route of delivery can be dependent on the disorder of the patient. For example, a subject diagnosed with HD can be administered an anti-htt RNA silencing agent of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic, (e.g., for alleviating symptoms), neuroprotective (e.g., for slowing or halting disease progression), or restorative (e.g., for reversing the disease process). For the treatment of HD, for example, symptomatic therapies can include the drugs haloperidol, carbamazepine, or valproate. Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the invention can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

XI. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

This invention is further illustrated by the following examples, which should not be construed as limiting. The contents of all references, patents and published patent applications cited throughout this application are incorporated herein by reference.

EXAMPLES

Unlike other types of autosomal dominant diseases, Huntington's disease does not contain a point mutation e.g., a single nucleotide change. Therefore, the strategy to design siRNA directed against a point mutation in the disease allele cannot be implemented. Instead, the present invention directs designed siRNAs against polymorphisms in the Huntingtin gene, of which there are about 30 available in GenBank. The present invention also identifies the polymorphism in the Huntington disease allele which differs from the wild type allele, so that siRNA destroys only the disease mRNA and leaves intact the wild type (normal) allele mRNA. Thus, only the mutant Huntingtin protein is destroyed and the normal protein is intact.

Example I

Testing of RNAi Agents (e.g., siRNAs) Against Mutant Htt in *Drosophila* Lysates A siRNA targeting position 2886 in the htt mRNA was designed as described supra. The sequence of the siRNA is depicted in FIG. 5a (SEQ ID NO:24 sense; 25 anti-sense). Synthetic RNA (Dharmacon) was deprotected according to the manufacturer's protocol. siRNA strands were annealed (Elbashir et al., 2001a).

Target RNAs were prepared as follows. Target RNAs were transcribed with recombinant, histidine-tagged, T7 RNA polymerase from PCR products as described (Nykänen et al., 2001; Hutvágner et al., 2002). PCR templates for htt sense and anti-sense were generated by amplifying 0.1 ng/ml (final concentration) plasmid template encoding htt cDNA using the following primer pairs: htt sense target, 5'-GCG TAA TAC GAC TCA CTA TAG GAA CAG TAT GTCTCA GAC ATC-3' (SEQ ID NO:30) and 5'-UUCG AAG UAU UCC GCG UAC GU-3' (SEQ ID NO:31); htt anti-sense target, 5'-GCG TAA TAC GAC TCA CTA TAG GAC AAG CCT AAT TAG TGA TGC-3' (SEQ ID NO:32). and 5'-GAA CAG TAT GTC TCA GAC ATC-3' (SEQ ID NO:33).

The siRNA was tested using an in vitro RNAi assay, featuring *Drosophila* embryo lysates. In vitro RNAi reactions and analysis was carried out as previously described (Tuschl et al., 1999; Zamore et al., 2000; Haley et al., 2003). Target RNAs were used at ~5 nM concentration so that reactions are mainly under single-turnover conditions. Target cleavage under these conditions is proportionate to siRNA concentration.

FIG. 5a shows the efficacy of the siRNA directed against position 2886 in the mutant htt. The data clearly demonstrate that the siRNA directs cleavage of the sense target to a greater degree than observed for the anti-sense target. However, it is noticed that this first-designed siRNA did not produce a very active molecule, at least in this in vitro assay. Thermodynamic analysis of the base pair strength at the two ends of the siRNA duplex indicated roughly equivalent base pair strengths. FIG. 4 depicts the thermodynamic analysis of siRNA sense (SEQ ID NO:20; 22 respectively) and anti-sense (SEQ ID NO:21; 23 respectively) strand 5' ends for the siRNA duplex in 5a. ΔG (kcal/mole) was calculated in 1M NaCl at 37° C.

To improved the efficacy of the designed siRNA duplex, the 5' end of the sense strand or position 19 of the anti-sense strand of the htt siRNA tested in FIG. 5a was altered to produce siRNA duplexes in which the 5' end of the sense strand was either fully unpaired (FIG. 5c; SEQ ID NO: 28 sense; SEQ ID NO:29 anti-sense) or in an A:U base pair (FIG. 5b; SEQ ID NO:26 sense; SEQ ID NO:27 anti-sense). The unpairing the 5' end of an siRNA strand-the sense strand, in this case-causes that strand to function to the exclusion of the other strand. When the htt sense strand 5' end was present in an A:U base pair and the htt anti-sense strand 5' end was in a G:C pair, the sense strand dominated the reaction (FIG. 5b-c), but the htt anti-sense strand retained activity similar to that seen for the originally-designed siRNA.

Example II

RNAi Knockdown of Htt Protein in Cultured Cells

In a first experiment, siRNAs targeting a polymorphism in the htt mRNA (i.e., the polymorphism at position 2886 in the htt mRNA) were tested for their ability to down-regulate endogenous Htt protein in HeLa cells. HeLa cells were cultures and transfected as follows. HeLa cells were maintained at 37° C. in Dulbecco's modified Eagle's medium (DMEM, Invitrogen) supplemented with 10% fetal bovine serum (FBS), 100 unit/ml penicillin and 100 μg/ml streptomycin (Invitrogen). Cells were regularly passaged at sub-confluence and plated at 70% confluency 16 hours before transfection. Lipofectamine™ (Invitrogen)-mediated transient transfection of siRNAs were performed in duplicate 6-well plates (Falcon) as described for adherent cell lines by the manufacturer. A standard transfection mixture containing 100-150 nM siRNA and 9-10 μl Lipofectamine™ in 1 ml serum-reduced OPTI-MEM® (Invitrogen) was added to each well. Cells were incubated in transfection mixture at 37 C for 6 hours and further cultured in antibiotic-free DMEM. For Western blot analysis at various time intervals, the transfected cells were harvested, washed twice with phosphate buffered saline (PBS, Invitrogen), flash frozen in liquid nitrogen, and stored at −80° C. for analysis.

Figure 6A:
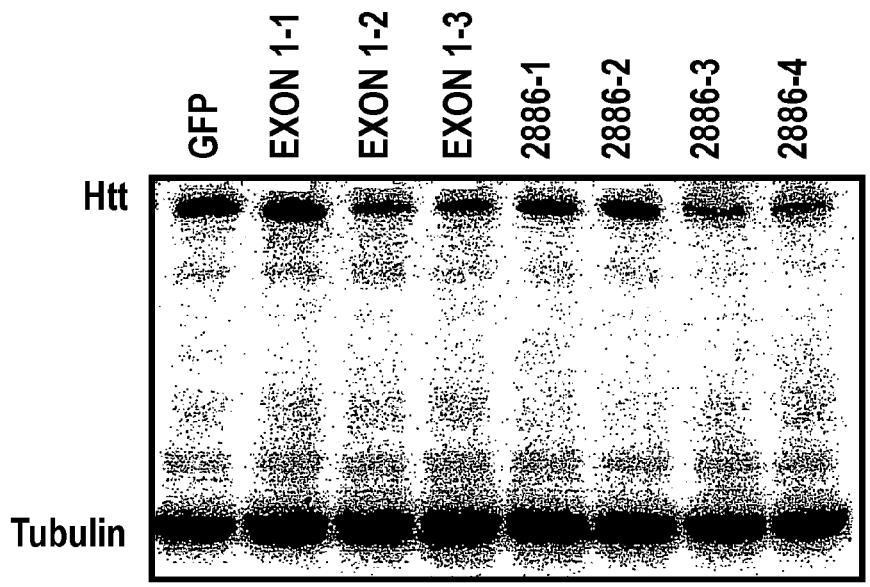
FIG. 6a-b. RNAi of endogenous Htt protein in HeLa cells. (a) Immunoblot of human Htt protein. (b) Quantification of same.
Figure 6B:
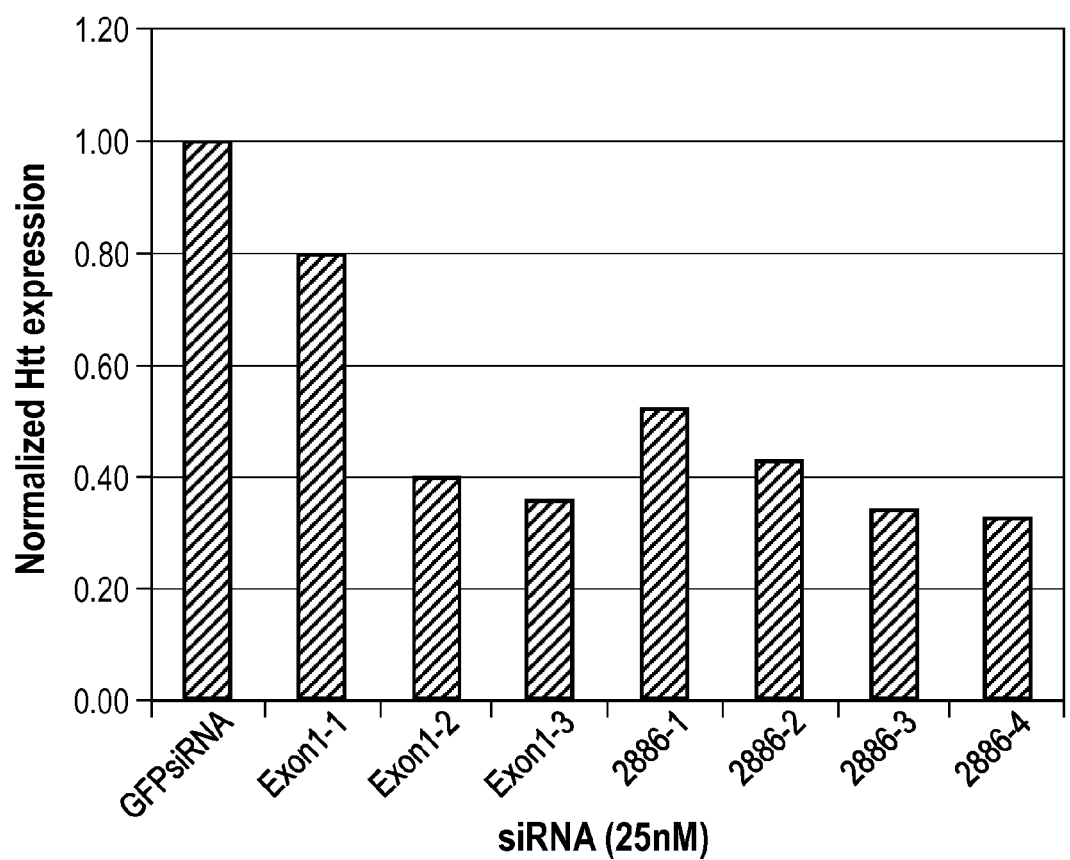

Three siRNAs were tested against a common target sequence in exon 1 and four siRNAs were tested for the position 2886 polymorphism. Western blot analysis was performed as follows. Cells treated with siRNA were harvested as described above and lysed in ice-cold reporter lysis buffer (Promega) containing protease inhibitor (complete, EDTA-free, 1 tablet/10 ml buffer, Roche Molecular Biochemicals). After clearing the resulting lysates by centrifugation, protein in clear lysates was quantified by Dc protein assay kit (Bio-Rad). Proteins in 60 μg of total cell lysate were resolved by 10% SDS-PAGE, transferred onto a polyvinylidene difluoride membrane (PVDF, Bio-Rad), and immuno-blotted with antibodies against CD80 (Santa Cruz). Protein content was visualized with a BM Chemiluminescence Blotting Kit (Roche Molecular Biochemicals). The blots were exposed to x-ray film (Kodak MR-1) for various times (30 s to 5 min). FIG. 6a depicts the results of the Western analysis. Tubulin served as the loading control. The data are quantified and normalized in FIG. 6b. Of the siRNAs tested, 2886-4, reproducibly showed enhanced efficacy in cultured HeLa cells (FIG. 6). This siRNA also reproducibly showed enhanced efficacy in vitro (not shown). GFP siRNA is a control siRNA that shares no sequence homology with htt mRNA.

siRNAs against polymorphic regions in the htt mRNA can likewise be tested in cells transfected with human htt cDNA or in cells transfected with htt reporter constructs. Lipofectamine™ (Invitrogen)-mediated transient cotransfections of cDNAs or reporter plasmids and siRNAs are performed as described supra. To test the ability of siRNAs to target htt reported constructs, RNAi was used to inhibit GFP-htt expression in cultured human Hela cell lines. Briefly, HeLa cells were transfected with GFP-htt siRNA duplex, targeting the GFP-htt mRNA sequence. To analyze RNAi effects against GFP-htt, lysates were prepared from siRNA duplex-treated cells at various times after transfection. Western blot experiments were carried out as described supra. Briefly, HeLa cells were harvested at various times post transfection, their protein content was resolved on 10% SDS-PAGE, transferred onto PVDF membranes, and immunoblotted with appropriate antibodies. Results of this study indicated that siRNA against GFP can eliminate expression of GFP-htt expression in Hela cells transfected with the GFP-htt gene. For studies targeting exogenously introduces htt, procedures are as described except that anti-Htt antibodies are used for immunoblotting.

RNAi can be used to inhibit htt expression in cultured neuronal cells as well. Exemplary cells include PC12 (Scheitzer et al., Thompson et al.) and NT3293 (Tagle et al.) cell lines as previously described. Additional exemplary cells include stably-transfected cells, e.g. neuronal cells or neuronally-derived cells. PC12 cell lines expressing exon 1 of the human huntingtin gene (Htt) can be used although expression of exon 1 reduces cell survival. GFP-Htt PC12 cells having an inducible GFP-Htt gene can also be used to test or validate siRNA efficacy.

Example III

Htt siRNA Delivery in an in vivo Setting

R6/2 mice models (expressing the R6/2 human htt cDNA product) are an accepted animal model to study the effectiveness of siRNA delivery in an in vivo setting. Genetically engineered R6/2 mice were used to test the effectiveness of siRNA at the 5' terminus of huntingtin mRNA. Htt siRNA was injected into the striatum of R6/2 mice through an Alzet pump. Mice were treated for 14 days with the siRNA/Alzet pump delivery system.

Results of this study indicated that two mice receiving the siRNA with Trans-IT TKO (Minis) as either a 20 or 200 nM solution at 0.250/hour showed no deterioration of motor impairment from day 67 to day 74. Generally, these R6/2 are expected to have a continued reduction in rotarod beyond day 60.

Example IV

SNP Analysis in Patients with Huntington's Disease (HD)

Single nucleotide polymorphism (SNP) sequencing analysis was performed to identify heterozygotic SNPs in patients with Huntington's Disease (HD). DNA samples were obtained from brain repositories in Charlestown, Mass., USA and New York City, N.Y. and a DNA repository in Ulm, Germany.

In one study, a total of 195 subjects (HD and control) were examined. Twenty-one SNP sites were identified; eighteen were reported in SNPPER and three have not previously been reported. In this population, four reported SNP sites were not confirmed. $^{149}/_{195}$ subjects (76%) contained SNP heterozygosity. The USA and German populations had 76% heterozygosity at SNP sites. HD patients and controls had the same frequency of SNP heterozygosity. Six SNP sites had an allelic frequency >30%.

In a second study, a total of twelve candidate polymorphic sites were sequenced in more than 107 HD brain specimens. Fifty-five percent of HD patients in the USA specimens ($^{26}/_{47}$; USA) and 57% of controls ($^{50}/_{88}$; USA) were heterozygous at one or more SNP site. Thirty-eight percent of HD patients in the German collection ($^{23}/_{60}$; Germany) were heterozygous at one or more polymorphic site. Forty-three of the total 107 HD patients had clusters of heterozygous polymorphic sites, with heterozygosity at five or eight SNP sites.

Example V

Testing of RNA Silencing Agents (e.g., siRNAs) Against Htt SNPs

Two SNPs (at genomic positions RS 363125 and RS 362331) were selected to test RNAi discrimination in an in vitro reporter assay.

SiRNAs targeting each SNP were designed as described supra. siRNA strands were annealed (Elbashir et al., 2001a).

Target RNAs may be prepared as follows. Target RNAs are transcribed with recombinant, histidine-tagged, T7 RNA polymerase from PCR products as described (Nykänen et al., 2001; Hutvágner et al., 2002). PCR templates for htt sense and anti-sense target RNA preparation are generated by amplifying plasmid template encoding htt cDNA using primer pairs. Each primer pair consists of forward and reverse primers which are complementary to regions that are immediately upstream and downstream, respectively, of one of the two alleles of a heterozygous SNP site.

Each siRNA was tested using a cell-based in vitro luciferase reporter assay. In vitro RNAi reactions and analysis may also be carried out in *Drosophila* embryo lysates as previously described (Tuschl et al., 1999; Zamore et al., 2000; Haley et al., 2003). Target RNAs are used at ~5 nM concentration so that reactions are mainly under single-turnover conditions. Target cleavage under these conditions is proportionate to siRNA concentration.

In RS363125 (predicted high discriminator), 80% knockdown was achieved at 0.5 nM siRNA for a siRNA having a guide strand perfectly complementary to a target mRNA containing the polymorphic adenosine ("A") SNP allele of the target SNP site from huntingtin, but containing a mismatch with a non-target mRNA containing the corresponding cytosine ("C") SNP allele of the heterozygous RS363125 SNP site (FIG. 10A). A single nucleotide mismatch effectively discriminated between both alleles of this SNP as the siRNA did not achieve the save level of knockdown of non-target ("mismatched") mRNA, even at up to 20 nM siRNA (FIG. 10B). In contrast, an siRNA having perfect complementary to the "C" SNP allele and a mismatch with the "A" SNP allele of the RS363125 SNP site (FIG. 11A) was effective in achieving discriminatory RNAi in favor of the "C" SNP allele (FIG. 11B).

Similar findings applied to the RS362331 polymorphism. The sequences of the 21-mer siRNAs targeting each SNP allele ("C" or "U") of the RS362331 polymorphism are depicted in FIG. 8A (SEQ ID NO: 34 sense; SEQ ID NO: 35 anti-sense) and FIG. 9A (SEQ ID NO: 38 sense; SEQ ID NO: 39 anti-sense). Each siRNA is perfectly complementary to the targeted SNP allele, but contains a mismatch with the non-targeted SNP allele at position 10 of the guide strand (P10).

Figure 9:
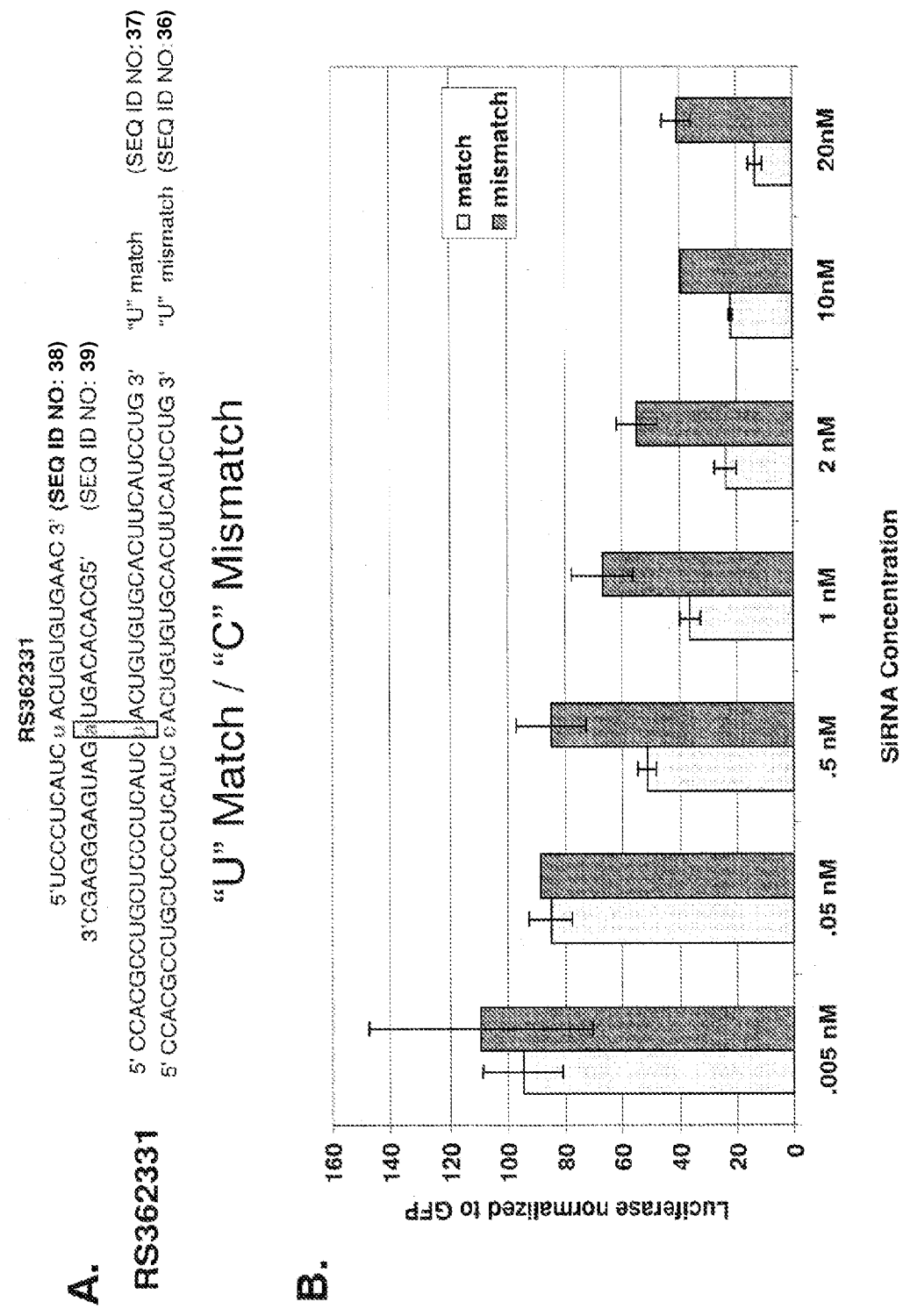
FIG. 9a-b: In vitro RNAi reactions programmed with siRNA targeting a second SNP allele (T) at heterozygous SNP site RS363331 within the human huntingtin gene. (a) Sequence of the siRNA (SEQ ID NO: 38; sense strand; SEQ ID NO: 39, guide strand) which is fully complementary to the target hht mRNA containing the "U" SNP allele (SEQ ID NO: 37) but which forms a A:C mismatch at position 10 (P10) with the non-target mRNA encoded by the corresponding "C" SNP (SEQ ID NO: 36). (b) Discriminatory RNA silencing (expressed as units of luciferase reporter gene activity relative to GFP) by the siRNA in (a) for the targeted "U" SNP allele ("match") versus the non-targeted "C" SNP allele ("mismatch").

FIG. 8B shows the efficacy of a siRNA directed against the SNP allele of RS362331 having a cytosine ("C") at the heterozygotic SNP site (SEQ ID NO:36; match). The data clearly demonstrate that the siRNA directs cleavage of the matched target SNP allele to a greater degree than observed for the mismatched target SNP allele (SEQ ID NO:37; mismatch). Similarly, FIG. 9B, shows the efficacy of siRNA against the SNP allele of RS362331 which has a uridine ("U") at the heterozygotic SNP site (SEQ ID NO: 37; match). Greater than 50% knockdown of the targeted SNP allele is achieved at 0.5 nM siRNA, while the non-targeted "C" SNP allele (SEQ ID NO:36; mismatch) is relatively unaffected.

Figure 13:
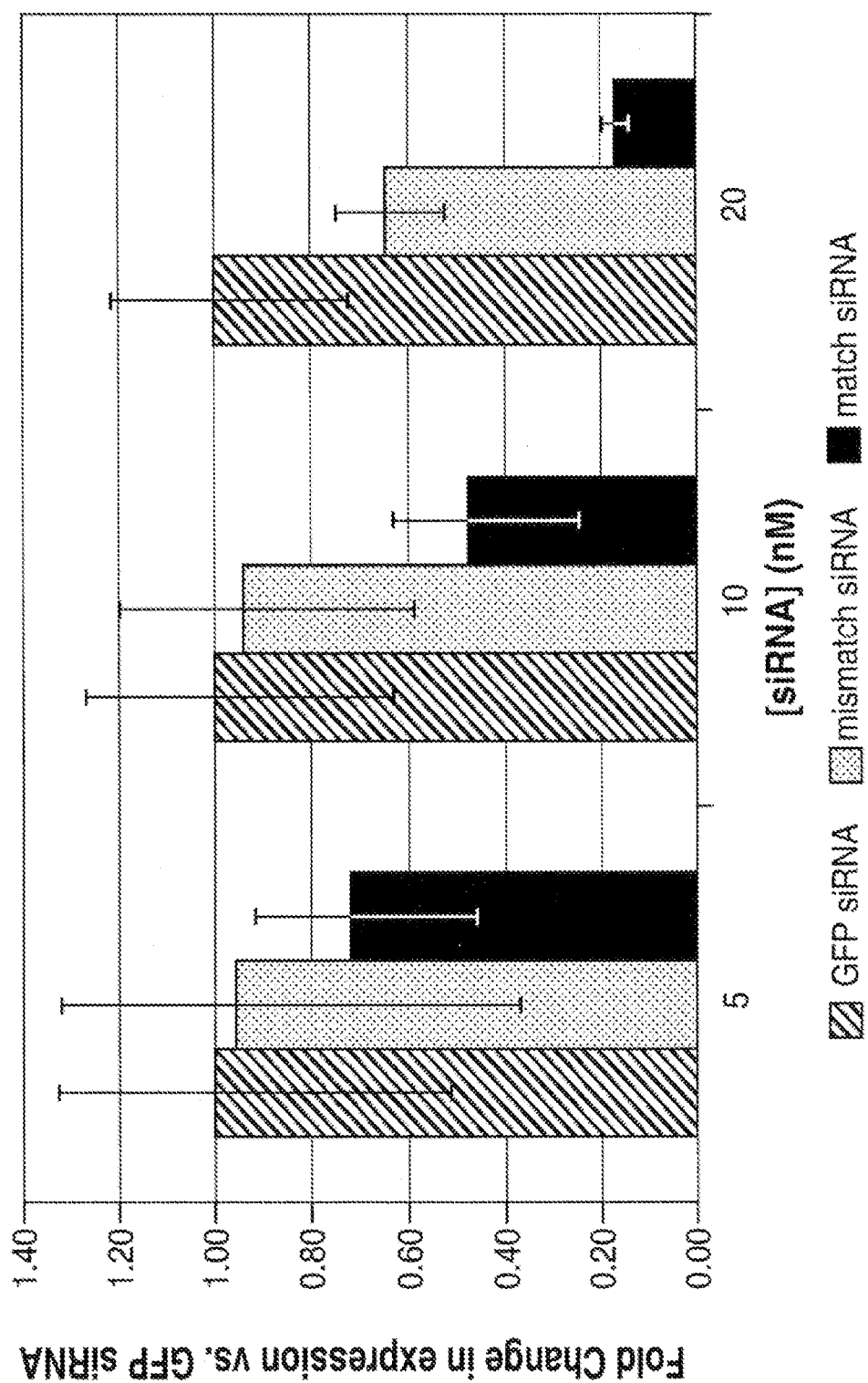
FIG. 13: Relative change in htt target mRNA levels in HEK cells transfected with 5, 10, or 20 nM of the matched and mismatched siRNAs depicted in FIGS. 12(a) and 12(b) and an unrelated GFP siRNA as measured by quantitative RT-PCR.

The efficacy of siRNA directed against the homozygous C allele (SEQ ID NO: 48) in the 3'UTR of Htt gene was also tested. siRNAs having a guide strand with perfect complementary to the C allele (FIG. 12A) or containing a single U:C mismatch with the C allele at position 10 (P10) of the guide strand (FIG. 12B) were designed. Transfection was performed at an siRNA concentration of 20 nM in HEK cells homozygous for the C allele. Transfection efficiency was approximately 70%. As depicted in FIG. 12C and FIG. 12D, matched siRNAs were much more effective than mismatched siRNAs in achieving knockdown of both Htt target mRNA and protein levels, respectively. This pattern of gene silencing was consistently observed at lower siRNA concentrations (5 nM and 10 nM) as well (see FIG. 13).

These results indicate that siRNAs can preferentially silence one of the two SNP alleles differing at the polymorphic site and that heterozygous SNP sites in huntingtin are attractive targets for therapeutic siRNAs.

Example VI

Effect of RNA Silencing Agents (e.g., siRNAs) on Mutant Htt Protein Expression Western blotting may also be employed to test the ability of siRNAs to down-regulate endogenous Htt protein in cultured cells using any of the techniques described infra.

RNA silencing activity of SNP-specific siRNAs can be tested HeLa cells. HeLa cells are maintained at 37° C. in Dulbecco's modified Eagle's medium (DMEM, Invitrogen) supplemented with 10% fetal bovine serum (FBS), 100 unit/ml penicillin and 100 µg/ml streptomycin (Invitrogen). Cells are regularly passaged at sub-confluence and plated at 70% confluency 16 hours before transfection. Lipofectamine™ (Invitrogen)-mediated transient transfection of siRNAs are performed in duplicate 6-well plates (Falcon) as described for adherent cell lines by the manufacturer. A standard transfection mixture containing 100-150 nM siRNA and 9-10 μl Lipofectamine™ in 1 ml serum-reduced OPTI-MEM® (Invitrogen) are added to each well. Cells are incubated in transfection mixture at 37 C for 6 hours and further cultured in antibiotic-free DMEM. For Western blot analysis at various time intervals, the transfected cells are harvested, washed twice with phosphate buffered saline (PBS, Invitrogen), flash frozen in liquid nitrogen, and stored at −80° C. for analysis.

Western blot analysis is performed as follows. Cells treated with siRNA are harvested as described above and lysed in ice-cold reporter lysis buffer (Promega) containing protease inhibitor (complete, EDTA-free, 1 tablet/10 ml buffer, Roche Molecular Biochemicals). After clearing the resulting lysates by centrifugation, protein in clear lysates is quantified by Dc protein assay kit (Bio-Rad). Proteins in 60 μg of total cell lysate are resolved by 10% SDS-PAGE, transferred onto a polyvinylidene difluoride membrane (PVDF, Bio-Rad), and immuno-blotted with antibodies against CD80 (Santa Cruz). Protein content is visualized with a BM Chemiluminescence Blotting Kit (Roche Molecular Biochemicals). The blots are exposed to x-ray film (Kodak MR-1) for various times (30 s to 5 min).

siRNAs against polymorphic regions in the htt mRNA can likewise be tested in cells transfected with human htt cDNA or in cells transfected with htt reporter constructs. Lipofectamine™ (Invitrogen)-mediated transient cotransfections of cDNAs or reporter plasmids and siRNAs are performed as described supra. To test the ability of siRNAs to target htt reported constructs, RNAi is used to inhibit GFP-htt expression in cultured human Hela cell lines. Briefly, HeLa cells are transfected with GFP-htt siRNA duplex, targeting the GFP-htt mRNA sequence. To analyze RNAi effects against GFP-htt, lysates are prepared from siRNA duplex-treated cells at various times after transfection. Western blot experiments are carried out as described supra.

Inhibition of htt expression can be assessed in cultured neuronal cells as well. Exemplary cells include PC12 (Scheitzer et al., Thompson et al.) and NT3293 (Tagle et al.) cell lines as previously described. Additional exemplary cells include stably-transfected cells, e.g. neuronal cells or neuronally-derived cells. PC12 cell lines expressing exon 1 of the human huntingtin gene (Htt) can be used although expression of exon 1 reduces cell survival. GFP-Htt PC12 cells having an inducible GFP-Htt gene can also be used to test or validate siRNA efficacy.

Example VII

Htt siRNA Delivery in an in vivo Setting

R6/2 mice models (expressing the R6/2 human htt cDNA product) are an accepted animal model to study the effectiveness of siRNA delivery in an in vivo setting. Genetically engineered R6/2 mice may be used to test the effectiveness of siRNA at the 5' terminus of huntingtin mRNA. Htt siRNA are injected into the striatum of R6/2 mice through an Alzet pump. Mice are treated for 14 days with the siRNA/Alzet pump delivery system.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

Aronin et al., Neuron, November; 15(5):1193-201 (1995)
Aronin et al., Phil Trans Royal Society, June 29; 354 (1386):995-1003 (1999)
Bagella et al., J. Cell. Physiol. 177:206-213 (1998)
Brummelkamp et al., Science 296:550-553 (2002)
Calegari et al., Proc. Natl. Acad. Sci. USA 99(22):14236-40 (2002)
Difiglia et al., Science, September 26; 277(5334):1990-3 (1997)
Elbashir et al., Genes Dev 15, 188-200 (2001a)
Haley et al., Methods 30, 330-336 (2003)
Hutvágner and Zamore, Science 297, 2056-2060 (2002)
Jacque et al., (2002)
Kremer et al., (1994)
Laforet et al., J. Neurosci., December 1; 21(23):9112-23 (2001)
Lee et al., EMBO J. 21: 4663-4670.(2002)
Lewis et al., Nature Genetics 32:107-108 (2002)
Lin et al., (1993)
Liu et al., (1999)
McCaffrey et al., Gene Ther. 2002 December; 9(23):1563 (2002)
McManus et al., RNA 8, 842-850 (2002)
Miyagishi et al., Nature Biotechnol. 20:497-500 (2002)
Nykänen et al., Cell 107, 309-321 (2001)
Paddison et al., Genes Dev 16, 948-958. (2002)
Paul et al., Nat Biotechnol 20, 505-508 (2002)
Scheitzer et al.
Sui et al., Proc Natl Acad Sci USA 99, 5515-5520 (2002)
Tagle et al.
Thompson et al.
Tuschl, T., Nat. Biotechnol. 2002 May; 20(5):446-8 (2002)
Tuschl et al., Genes Dev 13, 3191-3197 (1999)
Xia et al., (2002)
Yohrling G. J. et al., Mol Cell Neurosci. May; 23(1):28-38 (2003)
Yu et al., Proc Natl Acad Sci USA 99, 6047-6052 (2002)
Zamore et al., Cell 101, 25-33 (2000)
Zamore et al., Nature Medicine, volume 9 Number 3 pp 266-267 (2003)
Zeng et al., (2002)

What is claimed is:

1. A composition for treating a subject having or at risk for Huntington's disease caused by a mutation within the htt gene encoding a gain-of-function mutant huntingtin protein, comprising:
a vector that expresses an effective amount of an siRNA or an shRNA targeting a non-disease causing heterozygous single nucleotide polymorphism (SNP) within a gene encoding said mutant huntingtin protein located at a site distinct from the expanded CAG region mutation within the htt gene encoding the mutant huntingtin protein.

2. The composition of claim 1, wherein said siRNA or shRNA comprises a first strand comprising about 16-25 nucleotides homologous to a region of the gene comprising the polymorphism and a second strand comprising about 16-25 nucleotides substantially complementary to the first strand such that the first and second strands are capable of annealing together.

3. A composition for treating a subject having or at risk for Huntington's disease caused by a mutation within the htt gene encoding a gain-of-function mutant huntingtin protein, comprising a vector that expresses an effective amount of a siRNA or shRNA targeting a heterozygous SNP within a gene encoding said mutant huntingtin protein, wherein the SNP has an allelic frequency of at least 10% in a sample population and is present at a genomic site selected from the group consisting of RS362331, RS4690077, RS363125, RS363075, RS362268, RS362267, RS362307, RS362306, RS362305, RS362304, and RS362303.

4. The composition of claim 1, wherein the vector is a viral vector, retroviral vector, expression cassette, or plasmid.

5. The composition of claim 1, wherein the vector further comprises an RNA Polymerase III or RNA Polymerase II promoter.

6. The composition of claim 5, wherein the RNA Polymerase III promoter is the U6 or H1 promoter.

7. An isolated host cell comprising the vector of claim 4.

8. The isolated host cell of claim 7, which is a mammalian host cell.

9. The isolated host cell of claim 8, which is a non-human mammalian cell.

10. The isolated host cell of claim 8, which is a human cell.

11. A composition for treating a subject having or at risk for Huntington's disease characterized or caused by a mutant huntingtin (htt) protein, comprising a vector that expresses an effective amount of a siRNA targeting a heterozygous single nucleotide polymorphism (SNP) within a gene encoding the mutant htt protein, such that RNA silencing of said gene occurs, wherein the siRNA comprises
(i) an antisense strand or a variant thereof having sufficient complementarity to the SNP at genomic site RS362307 to direct target-specific RNA interference of the gene encoding the mutant htt protein; and
(ii) a sense strand or a variant thereof that is substantially complementary to the antisense strand, such that the sense and antisense strands are capable of annealing together.

12. A composition for treating a subject having or at risk for Huntington's disease characterized or caused by a mutant huntingtin (htt) protein, comprising a vector that expresses an effective amount of a siRNA targeting a heterozygous single nucleotide polymorphism (SNP) within a gene encoding the mutant htt protein, such that RNA silencing of said gene occurs, wherein the siRNA comprises
(i) an antisense strand or a variant thereof having sufficient complementarity to the SNP at genomic site RS362331 or RS363125 to direct target-specific RNA interference of the gene encoding the mutant htt protein; and
(ii) a sense strand or a variant thereof that is substantially complementary to the antisense strand, such that the sense and antisense strands are capable of annealing together.

* * * * *